US007037646B1

(12) United States Patent
Cook et al.

(10) Patent No.: US 7,037,646 B1
(45) Date of Patent: May 2, 2006

(54) AMINE-DERIVATIZED NUCLEOSIDES AND OLIGONUCLEOSIDES

(75) Inventors: Phillip Dan Cook, Vista, CA (US); Muthiah Manoharan, Carlsbad, CA (US); Charles J. Guinosso, Vista, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 08/602,862

(22) PCT Filed: Sep. 2, 1994

(86) PCT No.: PCT/US94/10131

§ 371 (c)(1),
(2), (4) Date: Feb. 28, 1996

(87) PCT Pub. No.: WO95/06659

PCT Pub. Date: Mar. 9, 1995

Related U.S. Application Data

(63) Continuation-in-part of application No. 08/117,363, filed on Sep. 3, 1994, now Pat. No. 6,783,931, and a continuation-in-part of application No. PCT/US91/00243, filed on Jan. 11, 1991, said application No. 08/117,363 is a continuation-in-part of application No. PCT/US92/09196, filed on Oct. 23, 1992, which is a continuation-in-part of application No. 07/782,374, filed on Oct. 24, 1991, said application No. 07/782,374 is a continuation-in-part of application No. 07/463,358, filed on Jan. 11, 1990, and a continuation-in-part of application No. 07/566,977, filed on Aug. 13, 1990, said application No. PCT/US91/00243 is a continuation-in-part of application No. 07/463,358, filed on Jan. 11, 1990, and a continuation-in-part of application No. 07/566,977, filed on Aug. 13, 1990.

(51) Int. Cl.
*C12Q 1/68* (2006.01)
*C07H 21/00* (2006.01)
*C07H 21/02* (2006.01)
*C07H 21/04* (2006.01)

(52) U.S. Cl. .................... 435/6; 514/44; 536/23.1; 536/24.5

(58) Field of Classification Search .............. 435/6; 514/44; 536/24.5, 23.1
See application file for complete search history.

(56) References Cited

U.S. PATENT DOCUMENTS

| 3,687,808 A | 8/1972 | Merigan et al. ............ 195/28 |
| 4,381,344 A | 4/1983 | Rideout et al. ............ 435/87 |
| 4,689,320 A | 8/1987 | Kaji ........................ 514/44 |
| 4,743,535 A * | 5/1988 | Carrico ..................... 435/6 |
| 4,910,300 A * | 3/1990 | Urdea et al. ............... 536/287 |
| 4,959,463 A | 9/1990 | Froehler et al. ........... 536/27 |
| 5,015,733 A | 5/1991 | Smith et al. ............... 536/23 |
| 5,108,921 A | 4/1992 | Low et al. ................ 435/240.1 |
| 5,138,045 A | 8/1992 | Cook et al. ................ 536/27 |
| 5,378,825 A | 1/1995 | Cook et al. ............... 536/25.34 |
| 5,451,463 A * | 9/1995 | Nelson et al. .............. 428/402 |
| 5,466,786 A | 11/1995 | Buhr et al. ............... 536/26.26 |
| 5,470,967 A | 11/1995 | Huie et al. ................ 536/24.3 |
| 5,578,718 A | 11/1996 | Cook et al. ............... 536/27.21 |

FOREIGN PATENT DOCUMENTS

| EP | 0 251 283 | 6/1987 |
| WO | WO 86/02929 | 5/1986 |
| WO | WO 89/02931 | 4/1989 |
| WO | WO 90/10448 | 9/1990 |
| WO | WO 91/00243 | 1/1991 |
| WO | WO 91/06556 | 5/1991 |
| WO | WO 91/14696 | 10/1991 |
| WO | WO 91/15500 | 10/1991 |
| WO | 92/05186 | * 4/1992 |
| WO | WO 92/05186 | * 4/1992 |

OTHER PUBLICATIONS

Goodchild, Bioconjugate Chemistry, 1(3):165-187. May 6, /Jun. 1990.*
Asseline, U. et al., "Nucleic acid-binding molecules with high affinity and base sequence specificity: Intercalating agents covalently linked to oligodeoxynucleotides", *Proc. Natl. Acad. Sci.*, 1984, 81, 3297-3301.
Atherton et al., *The Peptides*, Gross and Meienhofer, (eds.), Academic Press; New York, 1983, vol. 9, 1-38.
Beaucage, S.L. et al., "Advances in the Synthesis of Oligonucleotides by the Phosphoramidite Approach", *Tetrahedron*, 1992, 48, 2223-2311.
Betebenner, D.A. et al., "Hepatobiliary Delivery of Polyaminopolycarboxylate Chelates: Synthesis and Characterization of a Cholic Acid Conjugate of EDTA and Biodistribution and Imaging Studies with Its Indium-111 Chelate", *Bioconjugate Chem.*, 1991, 2, 117-123.
Chollet, A., "Selective Attachment of Oligonucleotides to Interleukin 1β and Targeted Delivery to Cells", *Nucleosides & Nucleotides*, 1990, 9, 957-966.
Cohen, *Oligonucleotides: Antisense Inhibitors of Gene Expression*, CRC Press, Inc., Boca Raton, Florida, 1989.
Corey, D.R. et al., "Generation of a Hybrid Sequence-Specific Single-Stranded Deoxyribonuclease", *Science*, 1987, 238, 1401-1403.

(Continued)

*Primary Examiner*—Jezia Riley
(74) *Attorney, Agent, or Firm*—Isis Patent Department

(57) ABSTRACT

Nucleosides and oligonucleosides functionalized to include alkylamino functionality, and derivatives thereof. In certain embodiments, the compounds of the invention further include steroids, reporter molecules, reporter enzymes, lipophilic molecules, peptides or proteins attached to the nucleosides through the alkylamino group.

27 Claims, No Drawings

OTHER PUBLICATIONS

Corey, D.R. et al., "Sequence-Selective Hydrolysis of Duplex DNA by and Oligonucleotide-Directed Nuclease", *J. Am. Chem. Soc.,* 1989, 111, 8523-8525.

Damha, M.J. et al., "An improved procedure for derivatization of controlled-pore glass beads for solid-phase oligonucleotides synthesis", *Nucl. Acids Res.,* 1990, 18(13), 3813-3821.

Delgado, C. et al., "The Uses and Properties of PEG-Linked Proteins", *Crit. Rev. in Therapeutic Drug Carrier Sys.,* 1992, 9, 249-304.

Dreyer, G.B. et al., "Sequence-specific cleavage of single-stranded DNA: Oligodeoxynucleotide-EDTA-Fe(II)", *Proc. Natl. Acad. Sci.,* 1985, 82, 968-972.

Englisch, U. et al., "Chemically Modified Oligonucleotides as Probes and Inihbitors", *Angew. Chem. Int. Ed. Eng.,* 1991, 30, 613-629.

Goodchild, J., "Conjugates of Oligonucleotides and Modified Oligonucleotides: A Review of Their Synthesis and Properties," *Bioconjugate Chem.,* 1990, 1(3), 165-187.

Greene et al., *Protective Groups in Organic Synthesis*, 2d edition, New York: John Wiley & Sons, 1991.

Guerra, F.I. et al., "Synthetic 6-Glucosyl Phospholipid as a Drug Transport System", *Tetrahedron Letts.,* 1987, 28, 3581-3584.

Haralambidis, J. et al., "Preparation of base-modified nucleosides suitable for non-radioactive label attachment and their incorporation into synthetic oligodeoxyribonucleotides", *Nucl. Acids. Res.,* 1987, 15, 4856-4877.

Haralambidis, J. et al., "The Solid Phase Synthesis of Oligonucleotides Containing a 3'-Peptide-Moeity", *Tetrahedron Letts.,* 1987, 28, 5199-5202.

Iyer, R.P. et al., "3H-1,2-Benzodithiole-3-one, 1,1-Dioxide as an Improved Sulfurizing Reagent in the Solid-Phase Synthesis of Oligodeoxyribonucleoside Phosphorothioates", *J. Am. Chem. Soc.,* 1990, 112, 1253-1254.

Juby, C.D. et al., "Facile Preparation of 3'Oligonucleotide-Peptide Conjugates", *Tetrahedron Letts.,* 1991, 32, 879-882.

Krieg, A.M. et al., "Uptake of Oligodeoxyribonucleotides by Lymphoid Cells Is Heterogeneous and Inducible", *Antisense Res. & Dev.,* 1991, 1, 161-171.

Lamaitre, M. et al., "Specific antiviral activity of a poly(L-lysine)-conjugated oligodeoxyribonucleotide sequence complementrary to vesicular stomatitis virus N protein mRNA initiation site", *Proc. Natl. Acad. Sci.,* 1987, 84, 648-652.

Leonetti, J.P. et al., "Biological Activity of Oligonucleotide-Poly(L-lysine) Conjugates: Mechanism of Cell Uptake", *Bioconjugate Chem.,* 1990, 1, 149-153.

Letsinger, R.L. et al., "Cholesteryl-conjugated oligonucleotides: Synthesis, properties and activity as inhibitors of replication of human immunodeficiency virus in cell culture", *Proc. Natl. Acad. Sci.,* 1989, 86, 6553-6556.

Manoharan, M. et al., "Novel Functionalization of the Sugar Moiety of Nucleic Acids for Multiple Labeling in the Minor Groove", *Tetrahedron Letts.,* 1991, 32, 7171-7174.

Manoharan, M. et al., "Chemical Modifications to Improve Uptake and Bioavailability of Antisense Oligonucleotides", *Annals NY Acad. Sciences,* 1992, 660, 306-309.

Miller, P.S. et al., "A New approach to chemotherapy based on molecular biology and nucleic acid chemistry: Matagen (masking tape for gene expression)", *Anti-Cancer Drug Des.,* 1987, 2, 117-128.

Nelson, P.S. et al., "Bifunctional oligonucleotide probes synthesized using a novel CPG: support are able to detect single base pair mutations", *Nucl. Acids. Res.,* 1989, 17, 7187-7195.

Ouchi, T. et al., "Synthesis and Antitumor Activity of Poly(Ethylene Glycol)s Linked to 5'-Fluorouracil via a Urethane or Urea Bond", *Drug Des. & Disc.,* 1992, 9, 93-105.

Ramirez, F. et al., "Nucleotidophospholipids; Oligonucleotide Derrivatives with Membrane-Recognition Groups", *J. Am. Chem. Soc.,* 1982, 104, 5483-5486.

Ravasio, N. et al., "Selective Hydrogenations Promoted by Copper Catalysts. 1. Chemoselectivity, Regioselectivity, and Stereoselectivity in the Hydrogenation of 3-Substituted Steroids", *J. Org. Chem.,* 1991, 56, 4329-4333.

Shea, R.G. et al., "Synthesis, hybridization properties and antiviral activity of lipid-oligodeoxynucletide conjugates", *Nucl. Acids Res.,* 1990, 18, 3777-3783.

Smith-Jones, P.M. et al., "Antibody Labeling with Copper-67 Using the Bifunctional Macrocycle 4-[(1,4,8,11-Tetraazacyclotetradec-1-yl)methyl] benzoic Acid", *Bioconjugate Chem.,* 1991, 2, 415-421.

Solomons, T.W.G. et al., *Organic Chemistry*, 1989, 2nd ed., John Wiley & Sons, 818-819.

Stein, C.A. et al., "Antisense Oligonucleotides as Therapeutic Agents—Is the Bullet Really Magical?", *Science*, 1993, 261, 1004-1012.

Telser, J. et al., "Synthesis and Characterization of DNA Oligomers and Duplexes Containing Covalently Attached Molecular Labels: Comparison of Biotin, Fluorescein, and Pyrene Labels by Thermodynamic and Optical Spectroscopic Measurements", *J. Am. Chem., Soc.,* 1989, 111, 6966-6976.

Veber, D.F., "Isonicotinyloxycarbonyl, a Novel Amino Protecting Group for Peptide Synthesis", *J. Org. Chem.,* 1977, 42, 3286-3288.

Wagner, D. et al., "Preparation and Synthesis Utility of Some Organotin Derivatives of Nucleotides", *J. Org. Chem.,* 1974, 39, 24-30.

Yamana, K. et al., "Synthesis of Oligonucleotide Derivatives with Pyrene Group at Sugar Fragment", *Tetrahedron Letts.,* 1991, 32, 6347-6350.

Yamana, K. et al., "Synthesis and Interactive Properties of an Oligonucleotides with Anthraquinone at the Sugar Frament", *Bioconjugate Chem*, 1990, 1, 319-324.

Zuckermann, R.N. et al., "Site-Selective Cleavage of RNA by a Hybrid Enzyme", *J. Am. Chem. Soc.,* 1988, 110, 1614-1615.

Asseline, U. et al., "Solid-Phase Preparation of 5',3'-Heterobifunctional Oligodeoxynucleotides using Modified Solid Supports", *Tetrahedron*, 1992, 48, 1233-1254.

Baker, B.F., "'Decapitation' of a 5'-Capped Oligoribonucleotide by σ-Phenanthroline: Cu(II)", *J. Am. Chem. Soc.,* 1993, 115, 3378-3379.

Bennett, C.F. et al., "Cationic Lipids Enhance Cellular Uptake and Activity of Phosphorothioate Antisense Oligonucleotides", *Mol. Pharmacol.,* 1992, 41, 1023-1033.

Bischoff, R. et al., "Introduction of 5'-Terminal Functional Groups into Synthetic Oligonucleotides for selective Immobilization", *Analyt. Biochem.,* 1987, 164, 336-344.

Blackburn, G.M. et al., "Studies in Phosphorylation. Part XXIX. The Synthesis of Dialkyil Phosphates from Monoalkyl Phosphonates: Direct Oxidative Esterification", *J. Chem. Soc.,* 1966, 239-245.

Caruthers, M.H., "Synthesis of Oligonucleotides and Oligonucleotide Analogues", *Oligonucleotides: Antisense Inhibitors of Gene Expression*, 1989, Chapter 1, Cohen, J.S. (Ed.), CRC Press, Boca Raton, FL, 7-24.

Chiang, M.Y. et al., "Antisense Oligonucleotides Inhibit Intercellular Adhesion Molecule 1 Expression by Two Distinct Mechanisms", *J. Biol. Chem.*, 1991, 266, 18162-18171.

Dingwall, C. et al., "Protein Import into the Cell Nucleus", *Ann. Rev. Cell Biol.*, 1986, 2, 367-390.

Di Zio, J.P. et al., "Progestin-Rhenium Complexes: Metal-Labeled Steroids with High Receptor Binding Affinity, Potential Receptor-Directed Agents for Diagnostic Imaging or Therapy", *Bioconjugate Chem.*, 1991, 2, 353-366.

Egholm, M. et al., "Peptide Nucleic Acids (PNA). Oligonucleotide Analogues with an Achiral Peptide Backbone", *J. Am. Chem Soc.*, 1992, 114, 1895-1897.

Ferentz, A.E. et al., "Disulfide Cross-Linked Oligonucleotides", *J. Am. Chem. Soc.*, 1991, 113, 4000-4002.

Fidanza, J.A. et al., "Site-Specific Labeling of DNA Sequences Containing Phosphorothioate Diesters", *J. Am. Chem. Soc.*, 1992, 114, 5509-5517.

Fidanza, J.A. et al., "Use of a Thiol Tether for the Site-Specifiic Attachment of Reporter Groups to DNA", *J. Org. Chem.*, 1992, 57, 2340-2346.

Froehler, B.C. et al., "Synthesis of DNA via deoxynucleoside II-phosphate intermediates", *Nucl. Acids Res.*, 1986, 14, 5397-5407.

Gaur, R.K. et al., "A simple method for the introduction of a thiol group at 5'-termini of oligodeocynucleotides", *Nucl. Acids Res.*, 1989, 17, 4404.

Greenfield, L. et al., "Thiol-Containign Cross-Linking Agent with Enhanced Steric Hinderance", *Bioconjugate Chem.*, 1990, 1, 400-410.

Harris, C.M. et al., "New Strategy for the Synthesis of Oligodeoxynucleotides Bearing Adducts as Exocyclic Amino Sites of Purine Nucleosides", *J. Am. Chem. Soc.*, 1991, 113, 4328-4329.

Jablonski, E. et al., "Preparation of oligodeoxynucleotide—alkaline phosphatase conjugates and their use as hybridization probes", *Nucl. Acids Res.*, 1986, 14, 6115-6128.

MacMillan, A.M. et al., "Synthesis of Functionally Tethered Oligodeoxynucleotides by the Convertible Nucleoside Approach", *J. Org. Chem.*, 1990, 55, 5931-5933.

Meyer, R.B. et al., "Effiicient, Specific Cross-Linking and Cleavage of DNA by Stable, Synthetic Complementary Oligodeoxynucleotides", *J. Am. Chem. Soc.*, 1989, 111, 8517-8519.

Mirabelli, C.K. et al., "In vitro and in vivo pharmacologic activities of antisense oligonucleotides", *Anti-Cancer Drug Des.*, 1991, 6, 647-661.

Mitchell, M.J. et al., "Boron trifluoride-methanol complex as a non-depurinating detritylating agent in DNA Synthesis", *Nucl. Acids Res.*, 1990, 18, 5321.

Mori, K. et al., "Synthesis and Properties of Novel 5'-Linked Oligos", *Nucleosides & Nucleotides*, 1989, 8, 649-657.

Pidgeon, C. et al., "Synthesis and Liposome Encapsulation of Antisense Oligonucleotide-Intercalator Conjugates", *Annals NY Acad. Sci.*, 593-596.

Schwartz, A. et al., "The DNA Bending by Acetylaminofluorene Residues and by Apurinic Sites", *J. Mol. Biol.*, 1989, 207, 445-450.

Sigman, D.S. et al., "Chemical Nucleases", *Biochem.*, 1990, 29, 9097-9105.

Sinha, N.D. et al., "The preparation and application of functionalised synthetic oligonucleotides: III. Use of H-phosphonate derivatives of protected amino-hexanol and mercapto-propanol or -hexanol", *Nucl. Acids Res.*, 1988, 16, 2659-2669.

Sluka, J.P. et al., "Reagents and Methods for the Solid-Phase Synthesis of Protein-EDTA for Use in Affinity Cleaving", *J. Am. Chem. Soc.*, 1990, 112, 6369-6374.

Sproat, B.S. et al., "The synthesis of protected 5'-mercapto-2',5'-dideoxyribonucleoside-3'-O-phosphoramidites; users of 5'-mercapto-oligodeoxyribonucleotides", *Nucl. Acids Res.*, 1987, 15, 4837-4849.

Tseng, B.Y. et al., "Antisense oligocucleotide technology in the development of cancer therapeutics", *Cancer Gene Therapeutics*, 1994, 1, 65-71.

Uhlmann, E. et al., "Antisense Oligonucleotides: A New Therapeutic Principle", *Chem. Reviews*, 1990, 90, 544-584.

Vasseur, J.J. et al., "Oligonucleosides: Synthesis of a Novel Methylhydroxylamine-linked Nucleoside Dimer and Its Incorporation into Antisense Sequences", *J. Am. Chem. Soc.*, 1992, 114, 4006-4007.

Wychowski, C. et al., "The Intranuclear Location of Simian Virus 40 Polypeptides VP2 and VP3 Depends on a Specific Amino Acid Sequence", *J. Virology*, 1987, 61, 3862-3869.

Yoneda, Y. et al., "Synthetic Peptides Containing a Region of SV40 Large T-Antigen Involved in Nuclear Localization Direct the Transport of Proteins into the Nucleus", *Exp.Cell Res.*, 1987, 170, 439-452.

Zhang, Z. et al., "Uptake of N-(4'-pyridoxyl)amines and release of amines by renal cells: A model for transporter-enhanced delivery of bioactive compounds", *Proc. Natl. Acad. Sci.*, 1991, 88, 10407-10410.

Zuckermann, R. et al., "Efficient methods for attachment of thiol specific probes to the 3'-ends of synthetic oligodeoxyribonucleotides", *Nucl. Acids Res.*, 1987, 15, 5305-5321.

Marcus-Sekura, C.J., "Techniques for Using Antisense Oligodeosyribonucleotides to Study Gene Expression", *Analyt. Biochem.*, 1988, 172, 289-295.

Agarwal, K.L. et al., "Synthesis and enzymatic properties of deoxyribooligonucleotides containing methyl and phenylphosphonate linkages," *Nucl Acids Res.*, 1979, 6, 3009-3023.

Agarwal, S. et al., "Oligodeoxynucleoside phosphoramidates and phosphorothioates as inhibitors of human immunodeficiency virus", *Proc. Natl. Acad Sci.*, 1988, 85, 7079-7083.

Agris, C.H. et al., "Inhibition of Vesicular Stromatitis Virus Protein Synthesis and Infection by Sequence-Specivid Oligodeoxyribonucleoside Methylphosphonates", *Biochem.*, 1986, 25, 6268-6275.

Biggadike, K. et al., "Short Convergent Route to Homochiral Carbocyclic 2'-Deoxynucleosides and Carbocyclic Ribonucleosides", *J. Chem. Soc. Chem. Commun.*, 1987, 1083-1084.

Brill, W.K. et al., "Synthesis of of oligodeoxynucleoside phosphorodithioates via thioamidites", *J. Am. Chem. Soc.*, 1989, 111, 2321-2322.

Castle, R.N. et al., "Imidazo[4,5-d] pyridazines. I. Synthesis of 4,7-Disubstituted Derivatives", *J. Org. Chem.*, 1958, 23, 1534-1538.

Cazenave, C. et al., "Enzymatic amplification of translation inhibition of rabbit β-globin mRNA mediated by antimessenger oligodeoxynucleotides covalently linked to intercalating agents", *Nucl. Acids Res.*, 1987, 15, 4717-4736.

Constant, J.F. et al., "Heterodimeric Molecules Including Nucleic Acid Bases and 9-Aminoacridine, Spectroscopic Studies, Conformations, and Interactions with DNA", *Biochem.*, 1988, 27, 3997-4003.

Guschlbauer et al., "Nucleoside conformation is determined by the electronegativity of the sugar substituent", *Nucl. Acids. Res.*, 1980, 8(6), 1421-1433.

Hobbs, J. et al., "Polynucleotides Containing 2'-Chloro-2'-deoxyribose", *Biochem.*, 1972, 11, 4336-4344.

Ikehara, M. et al., "Polynucleotides. LVI. Synthesis and properties of poly(2'-deoxy-2'fluroadenylic acid)", *Nucl. Acids Res.*, 1978, 5, 3315-3325.

Ikehara, M. et al., "Polynucleotides. L. Synthesis and properties of poly(2'-chloro-2'-deoxyadenylic acid) and poly (2'-bromo-'-deoxyadenylic acid)", *Nucl. Acids Res.*, 1977, 4, 4249-4260.

Ikehara et al., *Nucl. Acid Res.*, 1978, 5, 1877.

Ikehara, M. et al., *Eur. J. Biochem.*, 1984, 139, 447.

Inoue, H. et al., "Synthesis and hybridization studies on two complementary nona(2'-O-methyl)-ribonucleotides", *Nucl. Acids Res.*, 1987, 15, 6131-6148.

Jager, A. et al., "Oligonucleotide N-Alkylphosphoramidates: Synthesis and Binding to Polynucleotides", *Biochem.*, 1988, 27, 7237-7246.

Jayaraman, K. et al., "Selective Inhibition of *Escherichia coli* protein synthesis and growth by nonionic olignucleotides complementary to the 3' end of 16S rRNA", *Proc. Natl. Acad. Sci.*, 1981, 78, 1537-1541.

Jones, G.H. et al., "4'-Substituted Nucleosides. 5. Hydroxymethylation of Nucleoside 5'-Aldehydes", *J. Org. Chem.*, 1979, 44, 1309-1317.

Kazimierczuk, Z. et al., "Synthesis of 2'-Deoxytubercidin, 2'-Deoxyadenosine, and Related 2'-Deoxynucleosides via Novel Direct Stereospecific Sodium Salt Glycosylation Procedure", *J. Am. Chem. Soc.*, 1984, 106, 6379-6382.

Knorre, D.G. et al., "Complementary-Addressed (Sequence-Specific) Modification of Nucleic Acids", 1985, 32, 291-321.

Le Doan, T. et al., "Sequence-targeted chemical modification of nucleic acids by complementary oligonucleotides covalently linked to prophyrins", *Nucl. Acids Res.*, 1987, 15, 8643-8659.

Letsinger, R.L. et al., "Effects of pendant groups at phosphorus on binding properties of d-ApA analogues", *Nuc. Acids. Res.*, 1986, 14, 3487-3498.

Loose-Mitchell, D.S., "Antisense nucleic acids as a potential class of pharmaceutical agents", *TiPS*, 1996, 9, 45-47.

Marcus-Sekura, C.J. et al., "Comparative inhibition of chloramphenicol acetyltransferase gene expression by antisense oligonucleotide analogues having alkyl phosphotriester, methylphosphonate and phosphorothioate linkages", *Nucl. Acids Res.*, 1987, 15, 5749-5763.

Matsukura, M. et al., "Phosphorothioate analogs of oligodeoxynucleotides: Inhibitors of replication and cytopathic effects of human immunodeficiency virus", *Proc. Natl. Acad. Sci.*, 1987, 84, 7706-7710.

Miller, P.S. et al., "Synthesis and properties of Adenine and Thymine Nucleoside Alkyl Phosphotriesters, the Neutral Analogs of Dinucleoside Monophosphates", *J. Am. Chem. Soc.*, 1971, 93, 6657-6664.

Miller, P.S. et al., "Nonionic Nucleic Acid Analogues. Synthesis and Characterization of Dideoxyribonucleoside Methylphosphonates", *Biochem.*, 1979, 18, 5134-5143.

Miller, P.S. et al., "Biochemical and Biological Effects of Nonionic Nucleic Acid Methylphosphonates", *Biochem.*, 1981, 20, 1874-1880.

Outten, R.A. et al., "Synthetic 1-Methoxybenzo[d]naphtho [1,2-b]pyran-6-one C-Glycosides", *J. Org. Chem.*, 1987, 52, 5064-5066.

Revankar, G.R. et al., "Synthesis and Antiviral/Antitumor Activities of Ceertain 3-Deazaguanine Nucleosides and Nucleotides", *J. Med. Chem.*, 1984, 27, 1389-1396.

Robins, M.J. et al., "Nucleic Acid Related Compounds. 42. A General Procedure for the Efficient Deoxygenation of Secondary Alcohols. Regiospecific and Stereoselective Conversion of Ribonucleosides to 2'-Deoxynucleosides", *J. Am. Chem. Soc.*, 1983, 105, 4059-4065.

Roelen, H.C.P.F. et al., "Synthesis of nucleic acid methylphosphonthioates", *Nucl. Acids Res.*, 1988, 16(15), 7633-7645.

Ruby, S.W. et al., "An Early Hierarchic Role of U1 Small Nuclear Ribonucleoprotein in Spliceosome Assembly", *Science*, 1988, 242, 1028-1035.

Shibahara, S. et al., "Inhibition of human immunodeficiency virus (HIV-1) replication by synthetic oligo-RNA derivatives", 1989, 17(1), 239-252.

Sigman, D.S. et al., "Nuclease Activity of 1,10-Phenanthroline-Copper Ion", *Acc. Chem. Res.*, 1986, 19, 180-186.

Smith, C.C. et al., "Antiviral effect of an oligo(nucleoside methylphosphonate) complementary to the splice junction of herpes simplex virus type 1 immdiate early re-mRNAs 4 and 5", *Proc. Natl. Acad. Sci.*, 1986, 83, 2787-2791.

Stein, C.A. et al., "Oligodeoxynucleotides as Inhibitors of Gene Expression: A Review", *Cancer Res.*, 1988, 48, 2659-2668.

Stein, C.A. et al., "Physiochemical proterties of phosphorothioate oligodeoxynucleotides", *Nucl. Acids Res.*, 1988, 16, 3209-3221.

Suciu, N. et al., "Synthesis of 9-(2,5-*dideoxy*-β-D-glycero-pent-3-enofuranosyl)adenine", *Carbohydrate Res.*, 1975, 44, 112-115.

Tibanyenda, N. et al., "The effect of single base-pair mismatches on the duplex stability of d(T-A-T-T-A-A-T-A-T-C-A-A-G-T-T-G) d(C-A-A-C-T-T-G-A-T-A-T-T-A-A-T-A)", *Eur. J. Biochem.*, 1984, 139, 19-27.

Tidd, D.M. et al., "Evaluationof N-*ras* oncogene antisense, sense, and nonsense sequence methylphosphonate oligonucleotide analogues", *Anti-Cancer Drug Design*, 1988, 3, 117-127.

Uesugi, S. et al., "A Linear Relationship Between Electronegativity of 2'-Substituents and Conformation of Adenine Nucleosides", *Tetrahedron Letts.*, 1979, 42, 4073-4076.

van der Krol, A.R. et al., "Modulation of Eukaryotic Gene Expression by Complementary RNA or DNA Sequences", *BioTechniques*, 1988, 6, 958-976.

Walder, "Antisense DNA and RNA: progress and prospects", *Genes & Dev.*, 1988, 2, 502-504.

Walder, R. et al., "Role of RNase H in hybrid-arrested translation by antisense oligonucleotides", *Proc. Natl. Acad. Sci.*, 1988, 85, 5011-5015.

Yeung, A.T. et al., "Photoreactivities and Thermal Properties of Psoralen Cross-Links", *Biochemistry*, 1988, 27, 3204-3210.

Zon, G., "Synthesis of Backbone-Modified DNA analogues for Biological Applications", *J. Protein Chem.*, 1987, 6, 131-145.

Zon, G., "Oligonucleotide Analogues as Potential Chemotherapeutic Agents", *Pharm. Res.*, 1988, 5, 539-547.

Arnott, S. et al., "Optimised Parameters for A-DNA and B-DNA", *Biochem. & Biophys. Res. Comm.*, 1972, 47, 1504-1510.

Beaucage, S.L. et al., "Deoxynucleoside Phosphoramidites- A New Class of Key Intermediates of Deoxypolynucleotide Synthesis", *Tetrahedron Letts.*, 1981, 22, 1859-1862.

Butke, G. et al., "Facile Synthesis of 2'-Amino-2'-Deoxynucleoside from the Corresponding Arabino Derivative", *Nucleic Acid Chemistry*, Townsend, L.B. et al., eds., 1986, John Wiley & Sons, New York, 149-152.

Butke, G. et al., "Facile Synthesis of 2'-Amino-2'Deoxyadenosine", *J. Carbohydrates, Nucleosides, Nucleotides*, 1980, 7, 63-75.

Calvo-Mateo, A. et al., "3'-Cyano-3'-Deoxythymidine", *Tetrahedron Letts.*, 1988 23, 941-944.

Chen, Q.Y. et al., "Studies on Fluoroalkylation and Fluoroalkoxylation. Part 33. Direct Trifluoromethylation of Aryl Halides with Fluorosulphonyldiflyoromethyl Iodide in the Presence of Copper: an Electron Transfer Induced Process", *J. Chem. Soc. Perkin Trans. I*, 1989, 2385-2387.

Codington, J.F. et al., "Nucleosides. XVIII. Synthesis of 2'-Fluorothymidine, 2'-Fluorodeoxyuridine, and Other 2'-Halogeno-2'-Deoxy Nucleosides", *J. Org. Chem.*, 1964, 29, 558-564.

Damha, M.J. et al., "Solution and solid phage chemical synthesis of arabinonucleotides", *Can. J. Chem.*, 1989, 67, 831-839.

Freskos, J.N., "Synthesis of 2'-Deoxypyrimidine Nucleosides via Copper (I) Iodide Catalysis", *Nucleosides & Nucleotides*, 1989, 8, 1075-1076.

Gait, M. J. ed., "An Introduction to Modern Methods of DNA Synthesis," *Oligonucleotide Synthesis, A Practical Approach*, 1984, IRL Press, Oxford, 18-22.

Hertel, L.W. et al., "Synthesis of 2'-Deoxy-2,2-difluoro-D-ribose and 2'-Deoxy-2,2-difluoro-D-ribofuranosyl Nucleosides", *J. Org. Chem.*, 1988, 53, 2406-2409.

Ikehara, M. et al., "Studies of Nucleosides-and Nucleotides—LXXXII.Cyclonucleosides. (39). Synthesis and Properties of 2'-Halogeno-2'-deoxyadenosines", *Chem. Pharm. Bull.*, 1978, 26, 2449-2453.

Ikehara, M. et al., "Purine Cyclonucleosides-26 A Versatile Method for the Synthesis of Purine O-Cyclo—Nucleosides", *Tetrahedron*, 1975, 31, 1369-1372.

Ikehara, M., "Purine 8-Cyclonucleosides", *Accts. Chem. Res.*, 1969, 2, 47-53.

Ikehara, M. et al., "Studies of Nucleosides-and Nucleotides—LXXXIX. Purine Cyclonucleosides. (43). Synthesis and Properties of 2'-Halogeno-2'-deoxyguanosines", *Chem. Pharm. Bull.*, 1981, 29, 3281-3285.

Jarvi, E.T. et al., "Synthesis and Biological Evaluation of Dideoxynucleosides Containing a Difluoromethylene Unit", *Nucleosides & Nucleotides*, 1989, 8, 1111-1114.

Koole, L.H. et al., "Synthesis of Phosphate-Methylated DNA Fragments Using 9-Fluoroenylmethoxycarbonyl as Transient Base Protecting Group", *J. Org. Chem.*, 1989, 54, 1657-1664.

Markiewicz, W.T. et al., *Nucl. Acid Chem.*, 1986, Part 3, 222-231.

Parkes, K.E.B. et al., "A Short Synthesis of 3'-Cyano-3'-Deoxythymidine", *TetrahedronLetts.*, 1988, 29, 2995-2996.

Ranganathan, R., "Modification of the 2'-Position of Purine Nucleosides: Synthesis of 2'-α-Substituted-2'-deoxyadenosine Analogs", *Tetrahedron Letts.*, 1977, 15, 1291-1294.

Sproat, B.S. et al., "Highly efficient chemical synthesis of 2'-O-methyloligoribonucleotides and tetrabiotinylated derrivatives; novel proobes that are resistant to degradation by RNA or DNA specific nucleases", *Nucl. Acids Res.*, 1989, 17, 3373-3386.

Sproat, B.S. et al., "New synthetic routes to protected purine 2-O-methylriboside-3'-O-phosphoramidites using a novel alkylation procedure", *Nucl. Acids Res.*, 1990, 18, 41-49.

Ti, G.S. et al., "Transient Protection: Efficient One-Flask Synthesis of Protected Deoxynucleosides", *J. Am. Chem. Soc.*, 1982, 104, 1316-1319.

Uesugi, S. et al., "Improved Synthesis of 2'-Fluoro-2'-Deoxyadenosine and Synthesis and Carbon-13 NMR Spectrum of its 3',5'-Cyclic Phosphate Derivative", *Nucleosides & Nucleotides*, 1983, 2, 373-385.

Gaffney et al., "A New Strategy for the Protection of Deoxyguanosine During Oligonucleotide Synthesis", *Tetra. Lett.*, 1982, 23, 2257-2260.

Seela et al., "Palindromic Octa- and Dodecanucleotides Containing 2'-Deoxytubercidin: Synthesis, Hairpin Formation, and Recognition by the Endodeoxyribonuclease EcoRI" *Biochem.*, 1987, 26, 22333-2238.

Guesnet, J.-L., et al., "2D NMR studies and 3D structure of the parallel-stranded duplex oligonucleotide acrm$_5$-α-d (TCTAAACTC)-β-d(AGATTTGAG) via complete relaxation matrix analysis of the NOE effects and molecular mechanics calculations," *Biochemistry*, 1990, 29, 4982-4991.

Lancelot, et al. *Biochemistry*, 1988, 27, 1265-1273.

Ikehara, M., et al., "Studies on nucleosides and nucleotides. LXXXVII. Purine cyclonucleosides. XLII. Synthesis of 2'-deoxy02'fluoroguanosine," *Chem. Pharm. Bull.*, 1981, 29(4), 1034-1038.

Hansske, F., et al., "2' and 3'-ketonucleosides and their *ARABINO* and *XYLO* reduction products," *Tetrah. Letts.*, 1984, 40(1), 125-135.

Gosselin, G., et al., "Systematic synthesis and biological evaluation of α- and β-D-lyxofuranosyl nucleosides of the five naturally occurring nucleic acid bases," *J. Med. Chem.*, 1987, 30, 982-991.

\* cited by examiner

AMINE-DERIVATIZED NUCLEOSIDES AND OLIGONUCLEOSIDES

CROSS REFERENCE TO RELATED APPLICATIONS

This application is a continuation-in-part of U.S. application Ser. No. 08/117,363, filed Sep. 3, 1994 and of Application PCT/US91/00243, filed Jan. 11, 1991 (now U.S. application Ser. No. 07/854,634, filed Jul. 1, 1992). Application Ser. No. 08/117,363, in turn, is a continuation-in-part of Application PCT/US92/09196, filed Oct. 23, 1992, which is a continuation-in-part of U.S. application Ser. No. 07/782,374, filed Oct. 24, 1991. Application Ser. No. 07/782,374 and Application PCT/US91/00243 are both continuations-in-part of U.S. application Ser. No. 07/463,358, filed Jan. 11, 1990, and Ser. No. 07/566,977, filed Aug. 13, 1990. The entire disclosures of each of these applications, which are assigned to the assignee of this application, are incorporated herein by reference.

FIELD OF THE INVENTION

This application is directed to nucleosides, oligonucleotides and oligonucleosides functionalized to include alkylamino functionality, and derivatives thereof. In certain embodiments, the compounds of the invention further include steroids, reporter molecules, reporter enzymes, lipophilic molecules, peptides or proteins attached to the nucleosides through the alkylamino group.

BACKGROUND OF THE INVENTION

Messenger RNA (mRNA) directs protein synthesis. Antisense methodology is the complementary hybridization of relatively short oligonucleotides to mRNA or DNA such that the normal, essential functions of these intracellular nucleic acids are disrupted. Hybridization is the sequence-specific hydrogen bonding via Watson-Crick base pairs of oligonucleotides to RNA or single-stranded DNA. Such base pairs are said to be complementary to one another.

The naturally occurring events that provide the disruption of the nucleic acid function, discussed by Cohen in *Oligonucleotides: Antisense Inhibitors of Gene Expression*, CRC Press, Inc., Boca Raton, Fla. (1989) are thought to be of two types. The first, hybridization arrest, denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides (Miller, et al., *Anti-Cancer Drug Design* 1987, 2, 117) and α-anomer oligonucleotides are the two most extensively studied antisense agents which are thought to disrupt nucleic acid function by hybridization arrest.

The second type of terminating event for antisense oligonucleotides involves the enzymatic cleavage of the targeted RNA by intracellular RNase H. A 2'-deoxyribofuranosyl oligonucleotide or oligonucleotide analog hybridizes with the targeted RNA and this duplex activates the RNase H enzyme to cleave the RNA strand, thus destroying the normal function of the RNA. Phosphorothioate oligonucleotides are the most prominent example of an antisense agent that operates by this type of antisense terminating event.

Considerable research is being directed to the application of oligonucleotides and oligonucleotide analogs as antisense agents for diagnostics, research reagents and potential therapeutic purposes. At least for therapeutic purposes, the antisense oligonucleotides and oligonucleotide analogs must be transported across cell membranes or taken up by cells to express activity. One method for increasing membrane or cellular transport is by the attachment of a pendant lipophilic group.

Ramirez, et al., *J. Am. Chem. Soc.* 1982, 104, 5483, introduced the phospholipid group 5'-O-(1,2-di-O-myristoyl-sn-glycero-3-phosphoryl) into the dimer TpT independently at the 3' and 5' positions. Subsequently Shea, et al., *Nuc. Acids Res.* 1990, 18, 3777, disclosed oligonucleotides having a 1,2-di-O-hexyldecyl-rac-glycerol group linked to a 5'-phosphate on the 5'-terminus of the oligonucleotide. Certain of the Shea, et. al. authors also disclosed these and other compounds in patent application PCT/US90/01002. A further glucosyl phospholipid was disclosed by Guerra, et al., *Tetrahedron Letters* 1987, 28, 3581.

In other work, a cholesteryl group was attached to the inter-nucleotide linkage between the first and second nucleotides (from the 3' terminus) of an oligonucleotide. This work is disclosed in U.S. Pat. No. 4,958,013 and further by Letsinger, et al., *Proc. Natl. Acad. Sci. USA* 1989, 86, 6553. The aromatic intercalating agent anthraquinone was attached to the 2' position of a sugar fragment of an oligonucleotide as reported by Yamana, et al., *Bioconjugate Chem.* 1990, 1, 319. The same researchers placed pyrene-1-methyl at the 2' position of a sugar (Yamana et. al., *Tetrahedron Lett.* 1991, 32, 6347).

Lemairte, et al., *Proc. Natl. Acad. Sci. USA* 1986, 84, 648; and Leonetti, et al., *Bioconjugate Chem.* 1990, 1, 149. The 3' terminus of the oligonucleotides each include a 3'-terminal ribose sugar moiety. The poly(L-lysine) was linked to the oligonucleotide via periodate oxidation of this terminal ribose followed by reduction and coupling through a N-morpholine ring. Oligonucleotide-poly(L-lysine) conjugates are described in European Patent application 87109348.0. In this instance the lysine residue was coupled to a 5' or 3' phosphate of the 5' or 3' terminal nucleotide of the oligonucleotide. A disulfide linkage has also been utilized at the 3' terminus of an oligonucleotide to link a peptide to the oligonucleotide as is described by Corey, et al., *Science* 1987, 238, 1401; Zuckermann, et al., *J. Am. Chem. Soc.* 1988, 110, 1614; and Corey, et al., *J. Am. Chem. Soc.* 1989, 111, 8524.

Nelson, et al., *Nuc. Acids Res.* 1989, 17, 7187 describe a linking reagent for attaching biotin to the 3'-terminus of an oligonucleotide. This reagent, N-Fmoc-O-DMT-3-amino-1, 2-propanediol is now commercially available from Clontech Laboratories (Palo Alto, Calif.) under the name 3'-Amine on. It is also commercially available under the name 3'-Amino-Modifier reagent from Glen Research Corporation (Sterling, Va.). This reagent was also utilized to link a peptide to an oligonucleotide as reported by Judy, et al., *Tetrahedron Letters* 1991, 32, 879. A similar commercial reagent (actually a series of such linkers having various lengths of polymethylene connectors) for linking to the 5'-terminus of an oligonucleotide is 5'-Amino-Modifier C6. These reagents are available from Glen Research Corporation (Sterling, Va.). These compounds or similar ones were utilized by Krieg, et al., *Antisense Research and Development* 1991, 1, 161 to link fluorescein to the 5'-terminus of an oligonucleotide. Other compounds of interest have also been linked to the 3'-terminus of an oligonucleotide. Asseline, et al., *Proc. Natl. Acad. Sci. USA* 1984, 81, 3297 described linking acridine on the 3'-terminal phosphate group of an poly (Tp) oligonucleotide via a polymethylene linkage. Haralambidis, et al., *Tetrahedron Letters* 1987, 28, 5199 report building a peptide on a solid state support and then linking an oligonucleotide to that peptide via the 3' hydroxyl group of the 3' terminal nucleotide of the oligonucleotide. Chollet, *Nucleosides & Nucleotides* 1990, 9, 957 attached an Aminolink 2 (Applied Biosystems, Foster City, Calif.) to the 5' terminal phosphate of an oligonucleotide. They then used the bifunctional linking group SMPB (Pierce Chemical Co., Rockford, Ill.) to link an interleukin protein to the oligonucleotide.

An EDTA iron complex has been linked to the 5 position of a pyrimidine nucleoside as reported by Dreyer, et al., *Proc. Natl. Acad. Sci. USA* 1985, 82, 968. Fluorescein has been linked to an oligonucleotide in the same manner as reported by Haralambidis, et al., *Nucleic Acid Research* 1987, 15, 4857 and biotin in the same manner as described in PCT application PCT/US/02198. Fluorescein, biotin and pyrene were also linked in the same manner as reported by Telser, et al., *J. Am. Chem. Soc.* 1989, 111, 6966. A commercial reagent, Amino-Modifier-dT, from Glen Research Corporation (Sterling, Va.) can be utilized to introduce pyrimidine nucleotides bearing similar linking groups into oligonucleotides.

Cholic acid linked to EDTA for use in radioscintigraphic imaging studies was reported by Betebenner, et. al., *Bioconjugate Chem.* 1991, 2, 117; however, it is not known to link cholic acid to nucleosides, nucleotides or oligonucleotides.

OBJECTS OF THE INVENTION

It is one object of this invention to provide nucleosides, oligonucleotides and oligonucleosides that include alkylamino chemical functionality.

It is a further object of the invention to provide compounds having improved transfer across cellular membranes.

It is another object to provide compounds that include intercalators, nucleic acid cleaving agents, cell surface phospholipids, and/or diagnostic agents.

It is yet another object to provide improvements in research and diagnostic methods and materials for assaying bodily states in animals, especially disease states.

It is an additional object of this invention to provide therapeutic and research materials having improved transfer and uptake properties for the treatment of diseases through modulation of the activity of DNA or RNA.

BRIEF DESCRIPTION OF THE INVENTION

These and other objects are satisfied by the present invention, which provides compounds containing alkylamino chemical functionality. In one aspect, the invention provides nucleosides having base portions and ribofuranosyl sugar portions. Such nucleosides bear at a 2'-O-position, a 3'-O-position, or a 5'-O-position a substituent having formula:

—$R_A$—$N(R_{1a})(R_{1b})$ where:
$R_A$ is alkyl having from 1 to about 10 carbon atoms or $R_A$ is $(CH_2-CH_2-Q-)_x$;

$R_{1a}$ and $R_{1b}$, independently, are H, $R_2$, or an amine protecting group, have formula $C(X)-R_2$, $C(X)-R_A-R_2$, $C(X)-Q-R_A-R_2$, $C(X)-Q-R_2$, or, together, complete a cycloalkyl or cycloaryl moiety having two to six carbon atoms and one or two nitrogen atoms;

$R_2$ includes a steroid molecule, a reporter molecule, a lipophilic molecule, a reporter enzyme, a peptide, a protein, or has formula —Q—$(CH_2CH_2-Q-)_x$—$R_3$;

X is O or S;
each Q is, independently, is NH, O, or S;
x is 1 to about 200;
$R_3$ is H, $R_4$, C(O)OH, C(O)O$R_4$, C(O)$R_4$, $R_4$—$N_3$, $R_4$—$NH_2$, or $R_4$—SH; and
$R_4$ is Cl, Br, I, $SO_2R_5$ or has structure:

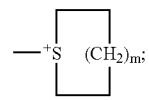

m is 2 to 7; and
$R_5$ is alkyl having 1 to about 10 carbon atoms.

In another aspect, the invention provides oligonucleotides and oligonucleosides comprising a plurality of linked nucleosides, wherein each nucleoside includes a ribofuranosyl sugar portion and a base portion and at least one (preferably more than one) of the nucleosides bears at a 2'-O-position, a 3'-O-position, or a 5'-O-position a substituent having formula —$R_A$—$N(R_{1a})(R_{1b})$.

In another aspect the invention provides methods for preparing oligonucleotides and oligonucleosides comprising the steps of contacting nucleosides according to the invention for a time and under reaction conditions effective to form a covalent bond therebetween. In preferred embodiments, at least one of the nucleosides bears a phosphoramidate group at its 2'-O-position or at its 3'-O-position.

In other embodiments, compounds according to the invention are prepared by contacting a nucleoside, oligonucleotide or oligonucleoside with derivatizing reagents. For example, a nucleoside, oligonucleotide or oligonucleoside bearing a 2'-hydroxy group, a 3'-hydroxy group, or a 5'-hydroxy group under basic conditions with a compound having formula $L_1$—$R_A$—$N(R_{1a})(R_{1b})$ wherein $L_1$ is a leaving group such as a halogen and at least one of $R_{1a}$ and $R_{1b}$ is an amine protecting group.

The present invention also provides methods for inhibiting the expression of particular genes in the cells of an organism, comprising administering to said organism a compound according to the invention. Also provided are methods for inhibiting transcription and/or replication of particular genes or for inducing degradation of particular regions of double stranded DNA in cells of an organism by administering to said organism a compound of the invention. Further provided are methods for killing cells or virus by contacting said cells or virus with a compound of the invention. The compound can be included in a composition that further includes an inert carrier for the compound.

DETAILED DESCRIPTION OF THE INVENTION

This invention provides nucleosides, oligonucleotides and oligonucleosides containing alkylamino chemical functionality. The nucleoside subunits can be "natural" or "synthetic" moieties. Each nucleoside is formed from a naturally occurring or synthetic base and a naturally occurring or synthetic pentofuranosyl sugar group.

The term "oligonucleotide" refers to a polynucleotide formed from a plurality of linked nucleotide units. The nucleotides units each include a nucleoside unit. In the context of this invention, the term "oligonucleoside" refers to a plurality of nucleoside units that are linked together. In a generic sense, since each nucleotide unit of an oligonucleotide includes a nucleoside therein, the term "oligonucleoside" can be considered to be inclusive of oligonucleotides (i.e., nucleosides linked together via phosphate linking groups). In a further sense, the term "oligonucleoside" also refers to a plurality of nucleosides that are linked together via linkages other than phosphate linkages. The term "oligonucleoside" thus effectively includes naturally occurring species or synthetic species formed from naturally occurring subunits. For brevity, the term "oligonucleoside" will be used as encompassing both phosphate linked (oligonucleotides) and non-phosphate linked polynucleoside species.

Oligonucleosides according to the invention also can include modified subunits. Representative modifications include modification of a heterocyclic base portion of a nucleoside or a sugar portion of a nucleoside. Exemplary modifications are disclosed in the following United States Patent Applications: Ser. No. 463,358, filed Jan. 11, 1990, entitled Compositions And Methods For Detecting And Modulating RNA Activity; Ser. No. 566,977, filed Aug. 13, 1990, entitled Sugar Modified Oligonucleotides That Detect And Modulate Gene Expression; Ser. No. 558,663, filed Jul. 27, 1990, entitled Novel Polyamine Conjugated Oligonucleotides; Ser. No. 558,806, filed Jul. 27, 1991, entitled Nuclease Resistant Pyrimidine Modified Oligonucleotides That Detect And Modulate Gene Expression and Serial No. PCT/US91/00243, filed Jan. 11, 1991, entitled Compositions and Methods For Detecting And Modulating RNA Activity. Each of these patent applications are assigned to the assignee of this invention. The disclosure of each is incorporated herein by reference.

The term oligonucleoside thus refers to structures that include modified portions, be they modified sugar moieties or modified base moieties, that function similarly to natural bases and natural sugars. Representative modified bases include deaza or aza purines and pyrimidines used in place of natural purine and pyrimidine bases; pyrimidines having substituent groups at the 5 or 6 position; and purines having altered or replacement substituent groups at the 2, 6 or 8 positions. Representative modified sugars include carbocyclic or acyclic sugars, sugars having substituent groups at their 2' position, and sugars having substituents in place of one or more hydrogen atoms of the sugar. Other altered base moieties and altered sugar moieties are disclosed in U.S. Pat. No. 3,687,808 and PCT application PCT/US89/02323.

Altered base moieties or altered sugar moieties also include other modifications consistent with the spirit of this invention. Such oligonucleosides are best described as being structurally distinguishable from yet functionally interchangeable with naturally occurring or synthetic wild type oligonucleotides. All such oligonucleosides are comprehended by this invention so long as they function effectively to mimic the structure of a desired RNA or DNA strand.

For use in antisense methodology, the oligonucleosides of the invention preferably comprise from about 10 to about 30 subunits. It is more preferred that such oligonucleosides comprise from about 15 to about 25 subunits. As will be appreciated, a subunit is a base and sugar combination suitably bound to adjacent subunits through, for example, a phosphorous-containing (e.g., phosphodiester) linkage or some other linking moiety. The nucleosides need not be linked in any particular manner, so long as they are covalently bound. Exemplary linkages are those between the 3'- and 5'-positions or 2'- and 5'-positions of adjacent nucleosides. Exemplary linking moieties are disclosed in the following references: Beaucage, et al., *Tetrahedron* 1992, 48, 2223 and references cited therein; and United States Patent Applications: Ser. No. 703,619, filed May 21, 1991; Ser. No. 903,160, filed Jun. 24, 1992; Ser. No. 039,979, filed Mar. 20, 1993; Ser. No. 039,846, filed Mar. 30, 1993; and Ser. No. 040,933, filed Mar. 31, 1993. Each of the foregoing patent applications are assigned to the assignee of this invention. The disclosure of each is incorporated herein by reference.

It is preferred that the RNA or DNA portion which is to be modulated using oligonucleosides of the invention be preselected to comprise that portion of DNA or RNA which codes for the protein whose formation or activity is to be modulated. The targeting portion of the composition to be employed is, thus, selected to be complementary to the preselected portion of DNA or RNA, that is, to be an antisense oligonucleoside for that portion.

In accordance with one preferred embodiment of this invention, the compounds of the invention hybridize to HIV mRNA encoding the tat protein, or to the TAR region of HIV mRNA. In another preferred embodiment, the compounds mimic the secondary structure of the TAR region of HIV mRNA, and by doing so bind the tat protein. Other preferred compounds are complementary to sequences for herpes, papilloma and other viruses.

The nucleosides and oligonucleosides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides. As used herein, therapeutics is meant to include the eradication of a disease state, by killing an organism or by control of erratic or harmful cellular growth or expression.

In one aspect, the present invention is directed to nucleosides and oligonucleosides that bear at least one amine-containing substituent at a position. Such substituents preferably have formula —$R_A$—$N(R_{1a})(R_{1b})$ and are appended at 2'-O—, 3'-O—, and/or 5'-O-positions.

Each $R_A$ according to the invention is an alkyl moiety independently selected to having 1 to about 10 carbon atoms or $R_A$ is a polyether, a polythioether or polyalkylamine. The term "alkyl" is intended to include straight chain and branched hydrocarbons. The preferred length of these hydrocarbons is 1 to about 7 carbon atoms, more preferably 3 or 4 carbon atoms.

$R_{1a}$ and $R_{1b}$ according to the invention are H, $R_2$, an amine protecting group, have formula $C(X)—R_2$, $C(X)—R_A—R_2$, $C(X)—Q—R_A—R_2$, $C(X)—Q—R_2$, or, together, complete a cycloalkyl or cycloaryl moiety having two to six carbon atoms and one or two nitrogen atoms such as an imidazole moiety. $R_{1a}$ and $R_{1b}$ according to the invention are H, $R_A$, $R_2$, an amine protecting group, or have formula $C(X)—R_2$, $C(X)—R_A—R_2$, $C(X)—Q—R_A—R_2$, $C(X)—Q—R_2$. Protecting groups are known per se as chemical functional groups that can be selectively appended to and removed from functionalities, such as amine groups. These groups are present in a chemical compound to render such functionality inert to chemical reaction conditions to which the compound is exposed. See, e.g., Greene and Wuts, Protective Groups in Organic Synthesis, 2d edition, John Wiley & Sons, New York, 1991. Numerous amine protecting groups are known in the art, including, but not limited to: phthalimide (PHTH), trifluoroacetate (triflate), allyloxycarbonyl (Alloc), benzyloxycarbonyl (CBz), chlorobenzyloxycarbonyl, t-butyloxycarbonyl (Boc), fluorenylmethoxycarbonyl (Fmoc), and isonicotinyloxycarbonyl (i-Noc) groups. (see, e.g., Veber and Hirschmann, et al., *J. Org. Chem.* 1977, 42, 3286 and Atherton, et al., The Peptides, Gross and Meienhofer, Eds, Academic Press; New York, 1983; Vol. 9 pp. 1–38).

$R_2$ can include a steroid molecule, a reporter molecule, a lipophilic molecule, a reporter enzyme, a peptide, a protein (i.e., a substituent consisting essentially of same), or a molecule having formula $—Q—(CH_2CH_2—Q—)_x—R_3$. For the purposes of this invention the terms "reporter molecule" and "reporter enzyme" are inclusive of those molecules or enzymes that have physical or chemical properties that allow them to be identified in gels, fluids, whole cellular systems, broken cellular systems and the like utilizing physical properties such as spectroscopy, radioactivity, calorimetric assays, fluorescence, and specific binding. Steroids include those chemical compounds that contain a perhydro-1,2-cyclopentanophenanthrene ring system. Proteins and peptides are utilized in their usual sense as polymers of amino acids. Normally peptides comprise such polymers that contain a smaller number of amino acids per unit molecule than do the proteins. Lipophilic molecules include naturally-occurring and synthetic aromatic and non-aromatic moieties such as fatty acids, esters, alcohols and other lipid molecules, substituted aromatic groups such as dinitrophenyl groups, cage structures such as adamantane and buckminsterfullerenes, and aromatic hydrocarbons such as benzene, perylene, phenanthrene, anthracene, naphthalene, pyrene, chrysene, and naphthacene.

Particularly useful as steroid molecules are the bile acids including cholic acid, deoxycholic acid and dehydrocholic acid; steroids including cortisone, digoxigenin, testosterone and cholesterol and even cationic steroids such as cortisone having a trimethylaminomethyl hydrazide group attached via a double bond at the 3 position of the cortisone rings. Particularly useful as reporter molecules are biotin, dinitrophenyl, and fluorescein dyes. Particularly useful as lipophilic molecules are alicyclic hydrocarbons, saturated and unsaturated fatty acids, waxes, terpenes and polyalicyclic hydrocarbons including adamantane and buckminsterfullerenes. Particularly useful as reporter enzymes are alkaline phosphatase and horseradish peroxidase. Particularly useful as peptides and proteins are sequence-specific peptides and proteins including phosphodiesterase, peroxidase, phosphatase and nuclease proteins. Such peptides and proteins include SV40 peptide, RNaseA, RNase H and Staphylococcal nuclease. Particularly useful as terpenoids are vitamin A, retinoic acid, retinal and dehydroretinol.

$R_2$ also can have formula $—Q—(CH_2CH_2—Q—)_x—R_3$, where Q is O, S, or NH. Subscript x can be 1 to about 200, preferably about 20 to about 150, more preferably about 10 to about 50. Preferably, Q are selected to be 0, such that $R_2$ constitutes a poly(ethyleneglycol) (PEG) group (i.e., $R_3$=H) or a functionalized derivative thereof (e.g., $R_3$=C(O)Cl). $R_3$ can be H, $R_A$, C(O)OH, C(O)OR$_A$, C(O)R$_4$, $R_A—N_3$, $R_A—NH_2$ or $R_A—SH$ where $R_4$ is F, Cl, Br, I, $SO_2R_5$ or a small thio-containing heterocycle having structure:

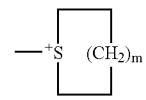

where m is 2 to 7. Representative PEG-containing $R_2$ groups are disclosed by Ouchi, et al., *Drug Design and Discovery* 1992, 9, 93, Ravasio, et al., *J. Org. Chem.* 1991, 56, 4329, and Delgardo et. al., *Critical Reviews in Therapeutic Drug Carrier Systems* 1992, 9, 249.

Oligonucleosides according to the invention can be assembled in solution or through solid-phase reactions, for example, on a suitable DNA synthesizer utilizing nucleosides according to the invention and/or standard nucleotide precursors. The nucleosides and nucleotide precursors can already bear alkylamino groups or can be later modified to bear such groups.

In the former case, compounds according to the invention are prepared by, for example, reacting nucleosides bearing at least one free 2'-, 3'-, or 5'-hydroxyl group under basic conditions with a compound having formula $L_1—(CH_2)_n—N(R_{1a})(R_{1b})$ where $L_1$ is a leaving group and at least one of $R_{1a}$ and $R_{1b}$ is an amine protecting group. Displacement of the leaving group through nucleophilic attack of an oxygen anion produces the desired amine derivative. Leaving groups according to the invention include but are not limited to halogen, alkylsulfonyl, substituted alkylsulfonyl, arylsulfonyl, substituted arylsulfonyl, hetercyclcosulfonyl or trichloroacetimidate. A more preferred group includes chloro, fluoro, bromo, iodo, p-(2,4-dinitroanilino)benzenesulfonyl, benzenesulfonyl, methylsulfonyl (mesylate), p-methylbenzenesulfonyl (tosylate), p-bromobenzenesulfonyl, trifluoromethylsulfonyl (triflate), trichloroacetimidate, acyloxy, 2,2,2-trifluoroethanesulfonyl, imidazoleysulfonyl, and 2,4,6-trichlorophenyl, with bromo being preferred.

Suitably protected nucleosides can be assembled into an oligonucleosides according to known techniques. See, e.g., Beaucage, et al., *Tetrahedron* 1992, 48, 2223.

Oligonucleosides according to the invention also can be prepared by assembling an oligonucleoside and appending alkylamino functionality thereto. For example, oligonucleosides having free hydroxyl groups can be assembled according to known techniques and then reacted with a reagent having formula $L_1—(CH_2)_n—N(R_{1a})(R_{1b})$. As will be recognized, however, greater selectivity can be achieved in terms of placement of alkylamino functionality within an oligonucleoside by introducing such functionality, as discussed above, on selected nucleosides and then using both the selected nucleosides and other nucleosides to construct an oligonucleoside.

Once assembled, an oligonucleoside bearing one or more groups having formula $—R_A—N(R_{1a})(R_{1b})$ wherein at least one of $R_{1a}$ and $R_{1b}$ is a protecting group is treated with reagents effective to remove the protecting group. Once deprotected, the oligonucleoside can be contacted with electrophillic moieties such as, for example, succinimidyl esters and other activated carboxylic acids including C(=O)—O-succinimide and C(=O)—O-pentafluorophenyl, isothiocyanates, sulfonyl chlorides, halacetamides, phospholipid carbocyclic acid active esters, o-phenanthroline-5-iodoacetamide, fluorescein isothiocyanate, 1-pyrene butyric acid-N-hydroxy succinimide ester and carboxylic acid derivatives of PNA (carboxylic acid derivatives of peptide nucleic acids). Preferred electrophillic moieties include cholesteryl-3-hemisuccinate-N-hydroxy succinimide ester, pyrene-1-butyric acid-N-hydroxy succinimide ester and polyethylene glycol-propionic acid-N-hydroxy succimide ester.

Thus, the invention first builds the desired linked nucleoside sequence in the normal manner on the DNA synthesizer. One or more (preferably two or more) of the linked nucleosides are then functionalized or derivatized with the lipophilic steroid, reporter molecule, lipophilic molecule, reporter enzyme, peptide or protein.

Additional objects, advantages, and novel features of this invention will become apparent to those skilled in the art upon examination of the following examples, which are not intended to be limiting. All oligonucleotide sequences are listed in a standard 5' to 3' order from left to right.

EXAMPLE 1

Oligonucleotides Having 2'-Protected-Amine Terminating Linking Group

A. Preparation of 5'-Dimethoxytrityl-2'-(O-Pentyl-N-phthalimido)-2'-Deoxyadenosine Phosphoramidite.

To introduce a functionalization at the 2' position of nucleotides within desired oligonucleotide sequences, 5'-dimethoxytrityl-2'-(O-pentyl-N-phthalimido)-2'-deoxyadenosine phosphoramidite was utilized to provide a linking group attached to the 2' position of nucleotide components of an oligonucleotide. This compound was synthesized generally in accordance with the procedures of patent application Ser. No. US91/00243 and 463,358, identified above, starting from adenosine. Briefly, this procedure treats adenosine with NaH in dimethylformamide (DMF) followed by treatment with N-(5-bromopentyl)phthalimide. Further treatment with $(CH_3)_3SiCl$, Ph—C(O)—Cl and $NH_4OH$ yields N6-benzyl protected 2'-pentyl-N-phthalimido functionalized adenosine. Treatment with DIPA and $CH_2Cl_2$ adds a DMT blocking group at the 5' position. Finally phosphitylation gives the desired phosphoramidite compound. This compound was utilized in the DNA synthesizer as a 0.09M solution in anhydrous $CH_3CN$. Oligonucleotide synthesis was carried out in either an ABI 390B or an ABI 394 synthesizer employing the standard synthesis cycles with an extended coupling time of 10 minutes during coupling of Compound 2 into the oligonucleotide sequence. Coupling efficiency of greater than 98% was observed.

B. 2'-Protected-Amine Linking Group Containing Phosphodiester Oligonucleotides

The following oligonucleotides having phosphodiester inter-nucleotide linkages were synthesized:

Oligomer 9: 5' TA*G 3';
Oligomer 10: 5' CCA* G 3';
Oligomer 11 (SEQ ID NO:1): 5' GGC TGA* CTG CG 3';
Oligomer 12 (SEQ ID NO:2): CTG TCT CCA* TCC TCA CT;
Oligomer 13 (SEQ ID NO:42): CTG TCT CCA* TCC TCT TCA* CT wherein A* represents a nucleotide functionalized to incorporate a pentyl-N-phthalimido functionality. Oligomers 12 and 13 are antisense compounds to the E2 region of the bovine papilloma virus-1 (BPV-1). Oligomers 12 and 13 have the same sequence as Oligomer 3 in application Ser. No. 782,374, except for the 2' modification. The oligonucleotides were synthesized in either a 10 μmol scale or a 3×1 μmol scale in the "Trityl-On" mode. Standard deprotection conditions (30% $NH_4OH$, 55° C., 24 hours) were employed. The oligonucleotides were purified by reverse phase HPLC (Waters Delta-Pak $C_4$ 15 μm, 300A, 25×100 mm column equipped with a guard column of the same material). They were detritylated and further purified by size exclusion using a Sephadex G-25 column. NMR analyses by both proton and phosphorus NMR confirmed the expected structure for the Oligomers 9 and 10.

C. 2'-Protected-Amine Linking Group Containing Phosphorothioate Oligonucleotides The following oligonucleotides having phosphorothioate inter-nucleotide linkages were synthesized:

Oligomer 14 (SEQ ID NO:3):
$T_sT_sG_s\ C_sT_sT_s\ C_sC_sA^*_s\ T_sC_sT_s\ T_sC_sC_s\ T_sC_sG_s\ T_sC$;
Oligomer 15 (SEQ ID NO:4):
$T_sG_sG_s\ G_sA_sG_s\ C_sC_sA_s\ T_sA_sG_s\ C_sG_sA^*_s\ G_sG_sC_s$; and
Oligomer 16 (SEQ ID NO:43:
$T_sG_sG_s\ G_sA^*_sG_s\ C_sC_sA^*_s\ T_sA^*_sG_s\ C_sG_sA^*_s\ G_sG_sC_s$ wherein A* represents a nucleotide functionalized to incorporate a pentyl-N-phthalimido functionality and the subscript "s" represents a phosphorothioate inter-nucleotide backbone linkage. Oligomer 14 is an antisense compound directed to the E2 region of the bovine papilloma virus-1 (BPV-1). Oligomers 15 and 16 are antisense compounds to ICAM. Oligomer 14 has the same sequence as Oligomer 3 in application Ser. No. 782,374, except for the 2' modification whereas Oligomers 15 and 16 have the same sequence as Oligomer 4 in application Ser. No. 782,374 except for the 2' modification. These oligonucleotides were synthesized as per the method of Example 1(B) except during the synthesis, for oxidation of the phosphite moieties, the Beaucage reagent (i.e., 3H-1,2-benzodithioate-3-one 1,1-dioxide, see, Radhakrishnan, et al., *J. Am. Chem. Soc.* 1990, 112, 1253) was used as a 0.24 M solution in anhydrous $CH_3CN$ solvent. The oligonucleotides were synthesized in the "Trityl-On" mode and purified by reverse phase HPLC utilizing the purification procedure of Example 1(B).

D. 2'-O-Methyl Derivatized, 2'-Protected-Amine Linking Group Containing RNA Oligonucleotides The following oligonucleotides having 2'-O-methyl groups on each nucleotide not functionalized with a 2'-protected amine functionalization were synthesized:

Oligomer 17 (SEQ ID NO:24): CCA A*GC CUC AGA; and
Oligomer 18 (SEQ ID NO:25): CCA GGC UCA GA*T wherein A* represents a nucleotide functionalized to incorporate a pentyl-N-phthalimido functionality and where the remaining nucleotides except the 3'-terminus nucleotide are each 2'-O-methyl derivatized nucleotides. The 3'-terminus nucleotide in both Oligomers 17 and 18 is a 2'-deoxy nucleotide. Both Oligomers 17 and 18 are antisense compounds to the HIV-1 TAR region. The oligonucleotides were synthesized as per the method of Example 6 in application Ser. No. 782,374 (utilizing Compound 2 thereof) for introduction of the nucleotides containing the pentyl-N-phthalimido functionality and appropriate 2-O-methyl phosphoramidite nucleotides from Chemgenes Inc. (Needham, Mass.) for the remaining RNA nucleotides. The 3'-terminus terminal 2'-deoxy nucleotides were standard phosphoamidites utilized for the DNA synthesizer. The oligonucleotides were deprotected and purified as per the method of Example 1(B).

EXAMPLE 2

Functionalization Of Oligonucleotides at the 2' Position

A. Functionalization with Biotin
1. Single Site Modification

About 10 O.D. units ($A_{260}$) of oligomer 12 (see, Example 1) (approximately 60 nmols based on the calculated extinction coefficient of $1.6756 \times 10^5$) was dried in a microfuge tube. The oligonucleotide was dissolved in 200 µl of 0.2 M NaHCO$_3$ buffer and D-biotin-N-hydroxysuccinimide ester (2.5 mg, 7.3 µmols) (Sigma, St. Louis, Mo.) was added followed by 40 µl DMF. The solution was let stand overnight. The solution was applied to a Sephadex G-25 column (0.7×15 cm) and the oligonucleotide fractions were combined. Analytical HPLC showed nearly 85% conversion to the product. The product was purified by HPLC (Waters 600E with 991 detector, Hamilton PRP-1 column 0.7×15 cm; solvent A: 50 mM TEAA pH 7.0; B: 45 mM TEAA with 80% acetonitrile: 1.5 ml flow rate: Gradient: 5% B for first 5 minutes, linear (1%) increase in B every minute thereafter) and further desalted on Sephadex G-25 to give the oligonucleotide:

Oligomer 19 (SEQ ID NO:5): CTG TCT CCA* TCC TCT TCA CT wherein A* represents a nucleotide functionalized to incorporate a biotin functionality linked via a 2'-O-pentyl-amino linking group to the 2' position of the designated nucleotide. HPLC retention times are shown in Table 1 below.

2. Multiple Site Modification

About 10 O.D. units ($A_{260}$) of Oligomer 13 (see, Example 1, approximately 60 nmols) was treated utilizing the method of Example 8(A)(1) in application Ser. No. 782,374 with D-biotin-N-hydroxysuccinimide ester (5 mg) in 300 µl of 0.2 M NaHCO$_3$ buffer/50 µl DMF. Analytical HPLC showed 65% of double labeled oligonucleotide product and 30% of single labeled products (from the two available reactive sites). HPLC and Sephadex G-25 purification gave the oligonucleotide:

Oligomer 20 (SEQ ID NO:44): CTG TCT CCA* TCC TCT TCA*CT wherein A* represents nucleotides functionalized to incorporate a biotin functionality linked via a 2'-O-pentyl-amino linking group to the 2' position of the designated nucleotide. HPLC retention times for this product (and its accompanying singly labeled products) are shown in Table 1 below.

B. Functionalization with Fluorescein
1. Single Site Modification

A 1M Na$_2$CO$_3$/1M NaHCO$_3$ buffer (pH 9.0) was prepared by adding 1M NaHCO$_3$ to 1 M Na$_2$CO$_3$. A 200 µl portion of this buffer was added to 10 O.D. units of Oligomer 12 (see, Example 1) in a microfuge tube. A 10 mg portion of fluorescein-isocyanate in 500 µl DMF was added to give a 0.05 M solution. A 100 µl portion of the fluorescein solution was added to the oligonucleotide solution in the microfuge tube. The tube was covered with aluminum foil and let stand overnight. The reaction mixture was applied to a Sephadex G-25 column (0.7×20 cm) that had been equilibrated with 25% (v/v) ethyl alcohol in water. The column was eluted with the same solvent. Product migration could be seen as a yellow band well separated from dark yellow band of the excess fluorescein reagent. The fractions showing absorption at 260 nm and 485 nm were combined and purified by HPLC as per the purification procedure of Example 2(A)(1). Analytical HPLC indicated 81% of the desired doubly functionalized oligonucleotide. The product was lyophilized and desalted on Sephadex to give the oligonucleotide:

Oligomer 21 [(SEQ ID NO: 45)]: CTG TCT CCA* TCC TCT TCA CT wherein A* represents a nucleotide functionalized to incorporate a fluorescein functionality linked via a 2'-O-pentyl-amino linking group to the 2' position of the designated nucleotide. HPLC retention times are shown in Table 1 below.

2. Multiple Site Modification

A 10 O.D. unit ($A_{260}$) portion of Oligomer 13 (from Example 1) was dissolved in 300 µl of the 1M Na$_2$HCO$_3$/1M Na$_2$CO$_2$ buffer of Example 2(B)(1) and 2001 µl of the fluorescein-isothiocyanate stock solution of Example 2(B)(1) was added. The resulting solution was treated as per Example 2(B)(1). Analytical HPLC indicated 61% of doubly labeled product and 38% of singly labeled products. Work up of the reaction gave the oligonucleotide:

Oligomer 22 (SEQ ID NO:46: CTG TCT CCA* TCC TCT TCA* CT wherein A* represents nucleotides functionalized to incorporate a fluorescein functionality linked via a 2'-O-pentyl-amino linking group to the 2' position of the designated nucleotide. HPLC retention times are shown in Table 1 below.

C. Functionalization with Cholic Acid
1. Single Site Modification

A 10 O.D. unit ($A_{260}$) portion of Oligomer 12 (see, Example 1) was treated with cholic acid-NHS ester (Compound 1 in application Ser. No. 782,374, 5 mg, 9.9 µmols) in 200 µl of 0.2 M NaHCO$_3$ buffer/40 µl DMF. The reaction mixture was heated for 16 hours at 45° C. The product was isolated as per the method of Example 2(B)(1). Analytical HPLC indicated greater than 85% product formation. Work up of the reaction gave the oligonucleotide:

Oligomer 23 (SEQ ID NO:47: CTG TCT CCA* TCC TCT TCA CT wherein A* represents a nucleotide functionalized to incorporate a cholic acid functionality linked via a 2'-O-pentyl-amino linking group to the 2' position of the designated nucleotide. HPLC retention times are shown in Table 1 below.

2. Multiple Site Modification

A 10 O.D. unit ($A_{260}$) portion of Oligomer 13 (see, Example 1) was treated with cholic acid-NHS ester (Compound 1 in application Ser. No. 782,374, 10 mg, 19.8 µmols) in 300 µl of 0.2 M NaHCO$_3$ buffer/50 µl DMF. The reaction mixture was heated for 16 hours at 45° C. The product was isolated as per the method of Example 2(A)(1). Analytical HPLC revealed 58% doubly labeled product, 17% of a first singly labeled product and 24% of a second singly labeled product. Work up as per Example 2(A)(1) gave the oligonucleotide:

Oligomer 24 (SEQ ID NO:48: CTG TCT CCA* TCC TCT TCA* CT wherein A* represents nucleotides functionalized to incorporate a cholic acid functionality linked via a 2'-O-pentyl-amino linking group to the 2' position of the designated nucleotide. HPLC retention times are shown in Table 1 below.

D. Functionalization with Digoxigenin

1. Single Site Modification

A 10 O.D. unit ($A_{260}$) portion of Oligomer 12 (see, Example 1) was treated with digoxigenin-3-O-methylcarbonyl-ε-aminocaproic N-hydroxy succinimide ester (Boehringer Mannheim Corporation, Indianapolis, Ind.) in 200 µl of 0.1 M borate pH 8.3 buffer/40 µl DMF. The reaction mixture was let stand overnight. The product was isolated as per the method of Example 2(A)(1). Work up of the reaction gave the oligonucleotide:

Oligomer 25 (SEQ ID NO:49): CTG TCT CCA* TCC TCT TCA CT wherein A* represents a nucleotide functionalized to incorporate a digoxigenin functionality linked via a 2'-O-pentyl-amino linking group to the 2' position of the designated nucleotide. HPLC retention times are shown in Table 1 below.

2. Multiple Site Modification

A 10 O.D. units ($A_{260}$) portion of Oligomer 13 (see, Example 1) was treated with digoxigenin-3-O-methylcarbonyl-ε-aminocaproic N-hydroxy succinimide ester (Boehringer Mannheim Corporation, Indianapolis, Ind.) in 300 µl of 0.1 M borate pH 8.3 buffer/50 µl DMF. The reaction mixture was let stand overnight. The product was isolated as per the method of Example 2(A)(1). Work up as per Example 2(A)(1) gave the oligonucleotide:

Oligomer 26 (SEQ ID NO:48: CTG TCT CCA* TCC TCT TCA* CT wherein A* represents nucleotides functionalized to incorporate a cholic acid functionality linked via a 2'-O-pentyl-amino linking group to the 2' position of the designated nucleotide. HPLC retention times are shown in Table 1 below.

TABLE 1

HPLC Retention Times Of Oligonucleotides Functionalized At 2' Position

| | Retention Time Minutes | |
|---|---|---|
| Oligomer | Mono Substitution | Multiple Substitution |
| Oligomer 12[1] | 21.78 | |
| Oligomer 13[1] | | 22.50 |
| Oligomer 19[2] | 23.58 | |
| Oligomer 20[2] | | 24.16[a] 25.19[b] |
| Oligomer 21[3] | 26.65 | |
| Oligomer 22[3] | | 26.99[a] 29.33[b] |
| | | 27.55[a] |
| Oligomer 23[4] | 30.10 | |
| Oligomer 24[4] | | 30.38[a] 37.00[b] |
| | | 32.22[a] |
| Oligomer 25[5] | 28.06 | |
| Oligomer 26[5] | | 28.14[a] 33.32[b] |
| | | 29.24[a] |

[a] Mono conjugated minor product;
[b] Doubly conjugated major product;
[1] Parent Oligonucleotide - no 2' functionalization;
[2] 2' Biotin functionalization;
[3] 2' Fluorescein functionalization;
[4] 2' Cholic Acid functionalization; and
[5] 2' Digoxigenin functionalization.

The conditions employed were as follows: Waters 600E with 991 detector, Hamilton PRP-1 column 0.7×15 cm; solvent A: 50 mM TEAA pH 7.0; B: 45 mM TEAA with 80% acetonitrile: 1.5 ml flow rate: Gradient: 5% B for first 5 minutes, linear (1%) increase in B every minute thereafter.

Procedure A

Confirmation of Structure of Functionalized Oligonucleotides Containing A Tethered 2'-Amino Moiety Oligonucleotides of the invention were digested with snake venom phosphodiesterase and calf-intestine alkaline phosphatase to their individual nucleosides. After digestion, the nucleoside composition was analyzed by HPLC. The HPLC analysis established that functionalized nucleotide compounds having the tethered 2'-amino moiety thereon were correctly incorporated into the oligonucleotide.

Snake venom phosphodiesterase [Boehringer-Mannheim cat. #108260, 1 mg (1.5 units)/0.5 ml] and alkaline phosphatase from calf intestine (1 unit/microliter, Boehringer-Mannheim cat. # 713023) in Tris-HCl buffer (pH 7.2, 50 mM) were used to digest the oligonucleotides to their component nucleosides. To 0.5 O.D. units of oligonucleotide in 50 µl buffer (nearly 40 µM final concentration for a 20 mer) was added 5 µl of snake venom phosphodiesterase (nearly 0.3 units/mL, final concentration) and 10 µl of alkaline phosphatase (app. 150 units/mL, final concentration). The reaction mixture was incubated at 37° C. for 3 hours. Following incubation, the reaction mixture was analyzed by HPLC using a reverse phase analytical column (app. 30×2.5 cm); solvent A: 50 mM TEAA pH 7; solvent B: acetonitrile; gradient 100% for 10 minutes, then 5% B for 15 minutes, then 10% B and then wash. The results of these digestion are shown in Table 2 for representative oligonucleotides.

TABLE 2

OLIGONUCLEOTIDE ANALYSIS VIA ENZYMATIC DIGESTION

| | Observed Ratios** | | | | |
|---|---|---|---|---|---|
| Oligomer | Abs. max. | 267 C | 252 G | 267 T | 260 A* | A |
| Oligomer 10 | 2 | 1 | | 1 | |
| Oligomer 11 | 3 | 5 | 2 | 1 | |
| Oligomer 12 | 9 | 1 | 8 | 1 | 1 |
| Oligomer 13 | 9 | 1 | 8 | 2 | |

*Nucleoside having 2'-O-linker attached thereto; and
**Corrected to whole numbers.

As is evident from Table 2, the correct nucleoside ratios are observed for the component nucleotides of the test oligonucleotides.

Procedure B

Determination of Melting Temperatures (Tm's) of Cholic Acid Oligonucleotide Conjugates The relative ability of oligonucleotides to bind to their complementary strand is compared by determining the melting temperature of the hybridization complex of the oligonucleotide and its complementary strand. The melting temperature (Tm), a characteristic physical property of double helices, denotes the temperature in degrees centigrade at which 50% helical versus coil (un-hybridized) forms are present. Tm is measured by using the UV spectrum to determine the formation and breakdown (melting) of hybridization. Base stacking, which occurs during hybridization, is accompanied by a reduction in UV absorption (hypochromicity). Consequently a reduction in UV absorption indicates a higher $T_m$. The higher the Tm, the greater the strength of the binding of the strands. Non-Watson-Crick base pairing has a strong destabilizing effect on the Tm. Consequently, absolute fidelity of base pairing is necessary to have optimal binding of an antisense oligonucleotide to its targeted RNA.

1. Terminal End Conjugates a. Synthesis

A series of oligonucleotides were synthesized utilizing standard synthetic procedures (for un-functionalized oligonucleotides) or the procedure of Example 3(A) in application Ser. No. 782,374 for oligonucleotides having a 5'-terminus amino linker bearing oligonucleotide or the procedure of Example 3 (B) in application Ser. No. 782,374 for 5'-terminus cholic acid-bearing oligonucleotides. Each of the oligonucleotides had the following 5-LO antisense sequence: 5' TCC AGG TGT CCG CAT C 3' (SEQ ID NO:6). The nucleotides were synthesized on a 1.0 µmol scale. Oligomer 32 was the parent compound having normal phosphodiester inter-nucleotide linkages. Oligomer 33 incorporated phosphorothioate inter-nucleotide linkages in the basic oligonucleotide sequence. Oligomer 34 is a an intermediate oligonucleotide having a 5'-aminolink at the 5'-terminus of the basic oligonucleotide sequence and Oligomer 35 was a similar 5'-aminolink compound incorporating phosphorothioate inter-nucleotide linkages. Oligomer 36 is a 5'-terminus cholic acid conjugate of the basic phosphodiester oligonucleotide sequence while Oligomer 37 is a similar 5'-cholic acid conjugate incorporating phosphorothioate inter-nucleotide linkages. Oligomers 32 and 33 were synthesized in a "Trityl-On" mode and were purified by HPLC. Oligomers 34 and 35 were synthesized as per Example 30(A) in application Ser. No. 782,374 without or with Beaucage reagent treatment, to yield phosphodiester or phosphorothioate inter-nucleotide linkages, respectively. Oligomers 36 and 37 were prepared from samples of Oligomers 34 and 35, respectively, utilizing a solution of cholic acid N-hydroxysuccinimide ester (Compound 1) 1 dissolved in DMF as per Example 3(B) in application Ser. No. 782,374. Oligomers 36 and 37 were purified by HPLC. The products were concentrated and desalted in a Sephadex G-25 column. Gel electrophoresis analyses also confirmed a pure product with the pure conjugate moving slower than the parent oligonucleotide or 5'-amino functionalized oligonucleotide.

b. Melting Analysis

The test oligonucleotides [either the phosphodiester, phosphorothioate, cholic acid conjugated phosphodiester, cholic acid conjugated phosphorothioate or 5'-aminolink intermediate phosphodiester or phosphorothioate oligonucleotides of the invention or otherwise] and either the complementary DNA or RNA oligonucleotides were incubated at a standard concentration of 4 µM for each oligonucleotide in buffer (100 mM NaCl, 10 mM Na-phosphate, pH 7.0, 0.1 mM EDTA). Samples were heated to 90 degrees C. and the initial absorbance taken using a Guilford Response II spectrophotometer (Corning). Samples were then slowly cooled to 15 degrees C. and then the change in absorbance at 260 nm was monitored during the heat denaturation procedure. The temperature was elevated 1 degree/absorbance reading and the denaturation profile analyzed by taking the 1st derivative of the melting curve. Data was also analyzed using a two-state linear regression analysis to determine the Tm's. The results of these tests are shown in Table 3 as are the HPLC retention times of certain of the test compounds.

TABLE 3

Melting Temperature Of The Hybridization Complex Of The Oligonucleotide And Its Complementary Strand

| Oligomer | Tm** DNA | Tm** RNA | HPLC Ret. Time* minutes |
|---|---|---|---|
| 32 | 62.6 | 62.0 | — |
| 33 | 55.4 | 54.9 | — |
| 34 | ND | ND | 13.6 |
| 35 | ND | ND | 17.0 |
| 36 | 63.4 | 62.4 | 22.0 |
| 37 | 56.3 | 55.8 | 22.5 |

*HPLC conditions: Walters Delta Pak C-18 RP 2.5 u column; at 0 min 100% 0.1 TEAA; at 30 min 50% TEAA and 50% Acetonitrile: Flow rate 1.0 ml/min.
**Tm at 4 µM each strand from fit of duplicate melting curves to 2-state model with linear sloping base line. Conditions: 100 mM NaCl, 10 mM Phosphate, 0.1 mM EDTA, pH 7.0.
ND = not determined As is evident from Table 2, conjugates of cholic acid at the end of the oligonucleotide do not affect the Tm of the oligonucleotides.

2. Strands Incorporating 2'-O-Pentylamino Linker a. Synthesis

An oligonucleotide of the sequence:

Oligomer 38 (SEQ ID NO:7): GGA* CCG GA*A* GGT A*CG A*G wherein A* represents a nucleotide functionalized to incorporate a pentylamino functionality at its 2'-position was synthesized in a one micromole scale utilizing the method of Example 1(B). The oligonucleotide was purified by reverse phase HPLC, detritylated and desalted on Sephadex G-25. PAGE gel analysis showed a single band. A further oligonucleotide, Oligomer 39, having the same sequence but without any 2'-O-amino linker was synthesis in a standard manner. A complementary DNA oligonucleotide of the sequence:

Oligomer 40 (SEQ ID NO:8): CCT GGC CTT CCA TGC TC was also synthesized in a standard manner as was a complementary RNA oligonucleotide of the sequence:

Oligomer 41 (SEQ ID NO:9): CCU GGC CTT CCA TGC TC.

b. Melting Analysis

Melting analysis was conducted as per the method of Procedure B(1)(b). The results are shown in Table 4.

TABLE 4

Melting Temperature Of The Hybridization Complex Of The Oligonucleotide And Its Complementary Strand

| Oligomer | Tm* DNA[1] | Tm* RNA[2] |
|---|---|---|
| 38 | 54.5 | 58.0 |
| 39 | 60.6 | 56.9 |

*Tm at 4 µM each strand from fit of duplicate melting curves to 2-state model with linear sloping base line. Conditions: 100 mM NaCl, 10 mM Phosphate, 0.1 mM EDTA, pH 7.0.
[1]Against DNA complementary strand, Oligomer 40.
[2]Against RNA complementary strand, Oligomer 41

As is evident from Table 4 against the RNA complementary strand the change in Tm's between the strand having 2'-amino linkers thereon and the unmodified strand is 1.1 degrees (0.22 change per modification). Against the DNA strand, the change is −6.1 degrees (−1.2 change per modification). When compared to the parent unmodified oligonucleotide the 2'-amino linker-containing strand has a stabilizing effect upon hybridization with RNA and a destabilizing effect upon hybridization with DNA.

Compounds of the invention were tested for their ability to increase cellular uptake. This was determined by judging either their ability to inhibit the expression of bovine papilloma virus-1 (BPV-1) or an assay involving luciferase production (for HIV-1).

Procedure C

Determination of Cellular Uptake Judged By The Inhibition Of Expression of Bovine Papilloma Virus-1 (bpv-1) As Measured By an E2 Transactivation Assay For this test, a phosphorothioate oligonucleotide analog of the sequence:

Oligomer 42 (SEQ ID NO:50: CTG TCT CCA TCC TCT TCA CT was used as the basic sequence. This sequence is designed to be complementary to the translation initiation region of the E2 gene of bovine papilloma virus type 1 (BPV-1). Oligomer 42 served as the positive control and standard for the assay. Oligomer 3 (from Example 4 in application Ser. No. 782,374) served as a second test compound. It has the same basic sequence except it is a phosphorothioate oligonucleotide and further it has a cholic acid moiety conjugated at the 3'-end of the oligonucleotide. Oligomer 2 (from Example 2 in application Ser. No. 782,374) served as a third test compound. Again it is of the same sequence, it is a phosphorothioate oligonucleotide and it has a cholic acid moiety conjugated at the 5'-end. Oligomer 5 (from Example 5 in application Ser. No. 782,374) served as a fourth test compound. Once again it has the same sequence, is a phosphorothioate oligonucleotide and it has a cholic acid moiety conjugated at both the 3'-end and 5'-end. A fifth test compound was a phosphorothioate oligonucleotide with no significant sequence homology with BPV-1. A sixth test compound was a further phosphorothioate oligonucleotide with no significant sequence homology with BPV-1. The last test compound, the seventh test compound, was a phosphorothioate oligonucleotide with cholic acid conjugated to the 3'-end but having no significant sequence homology with BPV-1. Compounds five, six and seven served as negative controls for the assay.

For each test I-38 cells were plated at $5 \times 10^4$ cells per cm$^2$ in 60 mm petri dishes. Eight hours after plating, medium was aspirated and replaced with medium containing the test oligonucleotide and incubated overnight. Following incubation, medium was aspirated and replaced with fresh medium without oligonucleotide and incubated for one hour. Cells were then transfected by the CaPO$_4$ method with 2 μg of pE2RE-1-CAT. After a four hour incubation period cells were glycerol shocked (15% glycerol) for 1 minute followed by washing 2 times with PBS. Medium was replaced with DMEM containing oligonucleotide at the original concentration. Cells were incubated for 48 hours and harvested. Cell lysates were analyzed for chloramphenicol acetyl transferase by standard procedures. Acetylated and nonacetylated $^{14}$C-chloramphenicol were separated by thin layer chromatography and quantitated by liquid scintillation. The results are expressed as percent acetylation.

Two lots of the positive control compound were found to acetylate at a level of 29% and 30%. The negative controls, test compounds five, six and seven, were found to acetylate at 59%, 58% and 47%, respectively. The 3'-cholic acid conjugate test compound, Oligomer 3, was found to acetylate to 23%, the 5'-cholic acid conjugate test compound, Oligomer 2, was found to acetylate to 36% and the test compound conjugated at both the 3'-end and the 5'-end, Oligomer 5, was found to acetylate to 27%.

The results of this test suggests that placement of a cholic acid moiety at the 3'-terminus of an oligonucleotide increase the activity. This in turn suggests that the increased activity was the result of increased cellular membrane transport.

Procedure D

Determination of Cellular Uptake Judged By Inhibition of pHIVluc With Cholic Acid Linked 2'-O-Methyl Substituted Oligonucleotides For this test the absence of an oligonucleotide in a test well served as the control. All oligonucleotides were tested as 2'-O-methyl analogs. For this test an oligonucleotide of the sequence:

Oligomer 43 (SEQ ID NO:10): CCC AGG CUC AGA where each of the nucleotides of the oligonucleotide includes a 2'-O-methyl substituent group served as the basic test compound. The second test compound of the sequence:

Oligomer 44 (SEQ ID NO:51): 5'-CHA CCC AGG CUC AGA wherein CHA represents cholic acid and where each of the nucleotides of the oligonucleotide includes a 2'-O-methyl substituent group, was also of the same sequence as the first test compound. This second test compound included cholic acid conjugated to its 5'-end and was prepared as per the method of Example 3 in application Ser. No. 782,374 utilizing 2'-O-methyl phosphoramidite intermediates as identified in Example 1(C). The third test compound of the sequence:

Oligomer 45 (SEQ ID NO:52): CCC AGG CUC AGA 3'-CHA wherein CHA represents cholic acid and where each of the nucleotides of the oligonucleotide includes a 2'-O-methyl substituent group was also of the same sequence as the first test compound. The third test compound included cholic acid conjugated to its 3'-end and was prepared as per the method of Example 4 in application Ser. No. 782,374 utilizing 2'-O-methyl phosphoramidite intermediates as identified in Example 1(C). The fourth test compound was a 2'-O-Me oligonucleotide of a second sequence:

Oligomer 46 (SEQ ID NO: 11): GAG CUC CCA GGC where each of the nucleotides of the oligonucleotide includes a 2'-O-methyl substituent group. The fifth test compound was of sequence:

Oligomer 47 (SEQ ID NO:53): 5'-CHA GAG CUC CCA GGC wherein CHA represents cholic acid and where each of the nucleotides of the oligonucleotide includes a 2'-O-methyl substituent group. It was of the same sequence as the fifth test compound. This test compound included cholic acid conjugated to its 5'-end and was prepared as per the method of Example 3 in application Ser. No. 782,374 utilizing 2'-O-methyl phosphoramidite intermediates as identified in Example 1(C).

A sixth test compound was a randomized oligonucleotide of the sequence:

Oligomer 48 (SEQ ID NO:12): CAU GCU GCA GCC.

HeLa cells were seeded at $4 \times 10^5$ cells per well in 6-well culture dishes. Test oligonucleotides were added to triplicate wells at 1 μM and allowed to incubate at 37°

C. for 20 hours. Medium and oligonucleotide were then removed, cells washed with PBS and the cells were CaPO$_4$ transfected. Briefly, 5 µg of pHIVluc, a plasmid expressing the luciferase cDNA under the transcriptional control of the HIV LTR constructed by ligating the KpnI/HindIII restriction fragments of the plasmids pT3/T7luc and pHIVpap (NAR 19(12)) containing the luciferase cDNA and the HIV LTR respectively, and 6 µg of pcDEBtat, a plasmid expressing the HIV tat protein under the control of the SV40 promoter, were added to 500 µl of 250 mM CaCl$_2$, then 500 µl of 2×HBS was added followed by vortexing. After 30 minutes, the CaPO$_4$ precipitate was divided evenly between the six wells of the plate, which was then incubated for 4 hours. The media and precipitate were then removed, the cells washed with PBS, and fresh oligonucleotide and media were added. Incubation was continued overnight. Luciferase activity was determined for each well the following morning. Media was removed, then the cells washed 2× with PBS. The cells were then lysed on the plate with 200 µl of LB (1% Trit X-100, 25 mM Glycylglycine pH 7.8, 15 mM MgSO$_4$, 4 mM EGTA, 1 mM DTT). A 75 µl aliquot from each well was then added to a well of a 96 well plate along with 75 µl of assay buffer (25 mM Glycylglycine pH 7.8, 15 mM MgSO$_4$, 4 mM EGTA, 15 mM KPO$_4$, 1 mM DTT, 2.5 mM ATP). The plate was then read in a Dynatec multiwell luminometer that injected 75 µl of Luciferin buffer (25 mM Glycylglycine pH 7.8, 15 mM MgSO$_4$, 4 mM EGTA, 4 mM DTT, 1 mM luciferin) into each well, immediately reading the light emitted (light units).

The random sequence compound (Oligomer 48) and the other non-cholic acid-conjugated test compounds (Oligomers 43 and 46) had comparable activity. The 5'-conjugate of the first sequence (oligomer 44) also had activity comparable to the non-conjugated compounds. The 5'-conjugate of the second sequence (Oligomer 47) showed a three-fold increase in activity compared to the non-conjugated compounds and the 3'-conjugate of the first sequence (oligomer 45) showed a further 3-fold increase in activity compared to Oligomer 47.

All the test cholic acid-bearing oligonucleotides showed significant inhibition of luciferase production compared to non-cholic acid-bearing oligonucleotides. This suggests that the increased activity was the result of increased cellular membrane transport of the cholic acid-bearing test oligonucleotides.

EXAMPLE 3

Preparation of 5'-O-[Dimethoxytrityl]-2'-O-[hexyl-(Ω-N-phthalimido)amino]uridine and 5'-O-[dimethoxytrityl]-3'-O-[hexyl(Ω-N-phthalimidoamino)uridine 2',3'-O-Dibutyl stannylene-uridine was synthesized according to the procedure of Wagner et. al., *J. Org. Chem.*, 1974, 39, 24. This compound was dried over P$_2$O$_5$ under vacuum for 12 hours. To a solution of this compound (29 g, 42.1 mmols) in 200 ml of anhydrous DMF were added (16.8 g, 55 mmols) of 6-bromohexyl phthalimide and 4.5 g of sodium iodide and the mixture was heated at 130° C. for 16 hours under argon. The reaction mixture was evaporated, co-evaporated once with toluene and the gummy tar residue was applied on a silica column (500 g). The column was washed with 2L of ethyl acetate (EtOAc) followed by eluting with 10% methanol (MeOH):90% EtOAc. The product, 2'- and 3'-isomers of O-hexyl-Ω-N-phthalimido uridine, eluted as an inseparable mixture ($R_f$=0.64 in 10% MeOH in EtOAc). By $^{13}$C NMR, the isomeric ration was about 55% of the 2' isomer and about 45% of the 3' isomer. The combined yield was 9.2 g (46.2%). This mixture was dried under vacuum and re-evaporated twice with pyridine. It was dissolved in 150 mL anhydrous pyridine and treated with 7.5 g of dimethyocytrityl chloride (22.13 mmols) and 500 mg of dimethylaminopyridine (DMAP). After 2 hour, thin layer chromatography (TLC; 6:4 EtOAc:Hexane) indicated complete disappearance of the starting material and a good separation between 2' and 3' isomers ($R_f$=0.29 for the 2' isomer and 0.12 for the 3' isomer). The reaction mixture was quenched by the addition of 5 mL of CH$_3$OH and evaporated under reduced pressure. The residue was dissolved in 300 mL CH$_2$Cl$_2$, washed successively with saturated NaHCO$_3$ followed by saturated NaCl solution. It was dried over Mg$_2$SO$_4$ and evaporated to give 15 g of a brown foam which was purified on a silica gel (500 g) to give 6.5 g of the 2'-isomer and 3.5 g of the 3' isomer.

EXAMPLE 4

Preparation of 5'-O-Dimethoxytrityl-2'-O-[hexyl-(Ω-N-phthalimido)amino]uridine-3'-O-(2-cyanoethyl-N,N-diisopropyl)-phosphoramidite The 5'-dimethoxytrityl-2'-[O-hexyl-(Ω-N-phthalimido)-amino]uridine (4 g, 5.2 mmole) was dissolved in 40 mL of anhydrous CH$_2$Cl$_2$. To this solution diisopropylaminetetrazolide (0.5 g, 2.9 mmol) was added and stirred overnight. TLC (1:1 EtoAC/hexane) showed complete disappearance of starting material. The reaction mixture was transferred with CH$_2$Cl$_2$ and washed with saturated NaHCO$_3$ (100 mL) followed by saturated NaCl solution. The organic layer was dried over anhydrous Na$_2$SO$_4$ and evaporated to yield 6.4 g of a crude product which was purified in a silica column (200 g) using 1:1 hexane/EtOAc to give 4.6 g (4.7 mmol, 90%) of the desired phosphoramidite.

EXAMPLE 5

Preparation of 5'-O-(Dimethoxytrityl)-3'-O-[hexyl-(Ω-N-phthalimido)amino]uridine-2'-O-succinyl-aminopropyl controlled pore glass Succinylated and capped aminopropyl controlled pore glass (CPG; 500 Å pore diameter, aminopropyl CPG, 1.0 grams prepared according to Damha et. al., *Nucl. Acids Res.* 1990, 18, 3813.) was added to 12 ml anhydrous pyridine in a 100 ml round-bottom flask. 1-(3-Dimethylaminopropyl)-3-ethyl-carbodiimide (DEC; 0.38 grams, 2.0 mmol)], triethylamine (TEA; 100 µl, distilled over CaH$_2$), dimethylaminopyridine (DMAP; 0.012 grams, 0.1 mmol) and nucleoside 5'-O-dimethoxytrityl-3'-O-[ hexyl-(Ω-N-phthalimidoamino)]uridine (0.6 grams, 0.77 mmol) were added under argon and the mixture shaken mechanically for 2 hours. More nucleoside (0.20 grams) was added and the mixture shaken an additional 24 hours. CPG was filtered off and washed successively with dichloromethane, triethylamine, and dichloromethane. The CPG was then dried under vacuum, suspended in 10 ml piperidine and shaken 15 minutes. The CPG was filtered off, washed thoroughly with dichloromethane and again dried under vacuum. The extent of loading (determined by spectrophotometric assay of dimethoxytrityl cation in 0.3 M p-toluenesulfonic acid at 498 nm) was approximately 28 μmol/g. The 5'-O-(dimethoxytrityl)-3'-O-[hexyl-(Ω-N-phthalimidoamino]uridine-2'-O-succinyl-aminopropyl controlled pore glass was used to synthesize the oligomers 5'-GACU*-3' and 5'-GCC TTT CGC GAC CCA ACA CU*-3' (SEQ ID NO:13) (where the * indicated the derivatized nucleotide) in an ABI 380B DNA synthesizer using phosphoramidite chemistry standard conditions. 45 and 200 O.D.'s of the 4-mer and 20-mer, respectively, were obtained from two and three 1 μmol syntheses after purification by RP-HPLC and desalting.

The oligomer 5'-GACU*-3' was used to confirm the structure of 3'-O-hexylamine tether introduced into the oligonucleotide by NMR. As expected a multiple signal was observed between 1.0–1.8 ppm in $^1$H NMR. The oligomer 5'-GCC TTT CGC GAC CCA ACA CU*-3' (SEQ ID NO:13) belongs to a HCV sequence and it was used to show the nuclease resistance properties of the 3'-O-amino tether [see example 38].

EXAMPLE 6

Preparation of 5'-O-(Dimethoxytrityl)-2'-O-[hexyl-(Ω-N-phthalimido)amino]3'-O-succinyl-aminopropyl controlled pore glass The procedure of Example 5 was repeated, except that 5'-O-(Dimethoxytrityl)-2'-O-[hexyl-(Ω-N-phthalimidoamido)amino]uridine was used in the loading process.

EXAMPLE 7

Preparation of 5'-O-(Dimethoxytrityl)-2'-O-(hexylamino)-uridine

5'-O-(dimethoxytrityl)-2'-O-[hexyl-(Ω-N-phthalimido amino)]uridine (4.5 grams, 5.8 mmol) was dissolved in 200 ml methanol in a 500 ml flask. Hydrazine (1 ml, 31 mmol) was added to the stirring reaction mixture. The mixture was heated to 60–65° in an oil bath and refluxed 14 hours. Solvent was evaporated in vacuo. The residue was dissolved in dichloromethane (250 ml) and extracted twice with an equal volume NH$_4$OH. The organic layer was evaporated to yield 4.36 grams of crude product, and NMR indicated that the product was not completely pure. R$_f$=0 in 100% ethyl acetate. The product was used in subsequent reactions without further purification.

EXAMPLE 8

Preparation of 5'-O-(dimethoxytrityl)-3'-O-[hexylaminol]uridine

The procedure of Example 7 was repeated, except that 5'-O-(dimethoxytrityl)-3'-O-[hexyl-(Ω-N-phthalimidoamino)]uridine was used as the starting material.

EXAMPLE 9

Preparation of 5'-O-(dimethoxytrityl)-2'-O-[hexyl-N-(1-pyrene propyl carbonyl)amino]uridine 5'-O-Dimethoxytrityl-2'-O-(hexylamino)uridine (0.5 g, 0.78 mmol) was dissolved in anhydrous DMF (15 mL). 1-Hydroxybenzotriazole (0.16 grams, 1.17 mmol) and 1-pyrene-butyric acid pentafluorophenyl ester (0.53 grams, 1.17 mmol) were added to the reaction mixture. The mixture was stirred under argon at room temperature for 2 hours, after which it was concentrated in vacuo. Residual DMF was coevaporated with toluene. The residue was dissolved in dichloromethane (50 mL) and washed with an equal volume saturated NaHCO$_3$. The aqueous layer was washed with dichloromethane and the combined organic extracts washed with an equal volume saturated NaCl. The aqueous layer was washed with dichloromethane and the combined organic layers dried over MgSO$_4$ and concentrated. The residue was chromatographed on a silica gel column, eluting with a gradient of 50% ethyl acetate in hexanes to 100% ethyl acetate. The desired product (0.83 grams, 58%) eluted with 100% ethyl acetate (R$_f$ 0.46 by thin-layer chromatography (TLC)).

EXAMPLE 10

Preparation of 5'-O-[Dimethoxytrityl]-2'-O-[hexyl-N-(1-pyrene propyl carbonyl)amino]uridine-3'-O-(2-cyanoethyl-N, N-diisopropyl)phosphoramidite 5'-O-[Dimethoxytrityl]-2'-O-[hexyl-N-(1-pyrene propyl carbonyl)amino] uridine (0.80 grams, 0.87 mmol) was dissolved in 20 mL dry dichloromethane. 2-Cyanoethyl N,N,N',N'-traisopropylphosphorodiamidite (purchased from Sigma Chemical Co; 800 μL, 2.4 mmol) and diisopropylamine tetrazolide (0.090 grams, 0.52 mmol) were added to the mixture, which was stirred under argon for 20 hours The reaction mixture was then concentrated in vacuo and the residue dissolved in dichloromethane (75 mL). The solution was washed with an equal volume of saturated NaHCO$_3$. The aqueous layer was washed with dichloromethane (20 mL) and the combined organic layers washed with an equal volume of saturated NaCl. The aqueous layer was washed with dichloromethane (20 mL) and the combined organic layers dried over MgSO$_4$ and concentrated. The residue was chromatographed on a silica gel column, eluting with a gradient of 50% ethyl acetate in hexanes to 100% ethyl acetate. The desired product (750 mg, 78% yield, R$_f$ 0.54 by TLC in 100% ethyl acetate) eluted with 100% ethyl acetate.

EXAMPLE 11

Preparation of 2'-O-[hexyl-N-(1-pyrene-propyl-carbonyl) amino]uridine

5'-O-dimethoxytrityl-2'-O-[hexyl-N-(1-pyrene-propylcarbonyl)amino]uridine (1.0 g) was dissolved in 20 mL CH$_2$Cl$_2$ and kept in ice-bath for 10 minutes. To the cold solution, 5 mL of 80% acetic acid in water was added and the solution was left to stand for 30 minutes. It was then evaporated to dryness and loaded into a silica column and eluted with 10% methanol in methylene chloride to give 2'-O-[hexyl-N-(1-pyrene-propyl-carbonyl)amino]uridine.

EXAMPLE 12

Preparation of 5'-O-(dimethoxytrityl)-2'-O-[hexyl-N-(1-pyrene propylcarbonyl) amino]uridine-3'-O-[succinylaminopropyl]-controlled pore glass Succinylated/capped aminopropyl controlled pore glass was dried under vacuum for 3 hours immediately before use. A portion (0.3 g) was added to 3 ml anhydrous pyridine in a 50 ml round-bottom flask. DEC (0.12 grams, 0.63 mmol), TEA (25 μl, distilled over CaH$_2$), DMAP (0.005 grams, mmol) and 5'-O-(dimethoxytrityl)-3'-O-[hexyl-N-(1-pyrene propyl carbonyl]amino-]uridine (0.21 grams, 0.22 mmol) were added under argon and the mixture shaken mechanically for 19 hours. More nucleoside (0.025 grams) was added and the mixture shaken an additional 5.5 hours. Pentachlorophenol (0.045 grams, mmol) was added and the mixture shaken 18 hours. CPG was filtered off and washed successively with dichloromethane, triethylamine, and dichloromethane. The resulting CPG was then dried under vacuum, suspended in 15 ml piperidine and shaken 30 minutes. CPG was filtered off, washed thoroughly with dichloromethane and again dried under vacuum. The extent of loading (determined by spectrophotometric assay of dimethoxytrityl cation in 0.3 M p-toluenesulfonic acid at 498 nm) was approximately 27 µmol/g. The product solid support was subsequently used to synthesize the oligomers.

EXAMPLE 13

Preparation of 5'-O-dimethoxytrityl-3'-O-[hexyl-N-(1-pyrene propyl carbonyl] amino] uridine-2'-O-(succinyl amino propyl) controlled pore glass The procedure of Example 12 is repeated, except that 5'-O-dimethoxytrityl-3'-O-[hexyl-N-(1-pyrene propyl carbonyl] amino] uridine is used.

EXAMPLE 14

Preparation of 5'-O-(dimethoxytrityl)-2'-O-[hexyl-N-(5-thio carbonyl-3,6-dipivolyl-fluorescein)amino] uridine Fluorescein isothiocyanate (Isomer I, available from Cal Biochem, La Jolla, Calif.) was treated with 12 equivalents of pivaloyl chloride in $Et_3N$/THF to give di-O-pivaloyl fluorescein isothiocyanate. This compound was purified in silica gel column using 3:1 hexane:ethyl acetate. Nucleoside 5'-O-(dimethoxytrityl)-2'-O-(hexylamino)uridine was then condensed with dipivolyl fluorescein isothiocyanate in $CH_2Cl_2$/pyrimidine. The resultant compound 5'-O-(dimethoxytrityl)-2'-O-[hexyl-N-(5-thiocarbonyl-3,6-dipivolyl-fluorescein) amino]uridine is then purified by using 100% ethyl acetate, in a silica column.

EXAMPLE 15

Preparation of 5'-O-dimethoxytrityl-2'-O-[hexyl-N-(5-thiocarbonyl-3,6-di-pivaloyl fluorescein) amino] uridine-3'-O-(2-cyanoethyl, N-N-diisopropyl phosphoramidite 5'-O-(dimethoxytrityl)-2'-O-[hexyl-N-(5-thiocarbonyl-3,6-dipivolyl fluorescein)amino]uridine (0.75 grams, 0.672 mmol) was dissolved in dry dichloromethane (20 mL). 2-Cyanoethyl N,N,N',N'-tetraisopropylphosphorodiamidite (700 µL, 2.2 mmol) and diisopropylamine tetrazolide were added to the mixture, which was stirred under argon for 16 hours. The reaction mixture was then concentrated in vacuo and the residue dissolved in dichloromethane (75 mL) followed by washing with an equal volume of saturated $NaHCO_3$. The aqueous layer was washed with dichloromethane (50 mL) and the combined organic layers washed with an equal volume of saturated NaCl. The aqueous layer was washed with dichloromethane (50 mL) and the combined organic layers dried over $MgSO_4$ and concentrated. The residue was chromatographed on a silica gel column, eluting with a gradient of 25% ethyl acetate in hexanes to 100% ethyl acetate. The desired product (670 mg, 77% yield, $R_f$ 0.79 by TLC) eluted with 100% ethyl acetate.

EXAMPLE 16

Preparation of 5'-O-(dimethoxytrityl)-2'-O-[hexyl-N-(5-thiocarbonyl-3,6-di-pivaloyl fluorescein) amino]uridine-3'-O-(succinylaminopropyl) controlled pore glass Succinylated and capped aminopropyl controlled pore glass (CPG) is dried under vacuum for 3 hours immediately before use. CPG (0.3 grams) is added to 3 ml anhydrous pyridine in a 50 ml round-bottom flask. DEC (0.12 grams, 0.63 mmol), TEA (25 µl, distilled over $CaH_2$, DMAP (dimethyl amino pyridine) (0.005 grams, 0.04 mmol) and 5'-O-dimethoxytrityl-2'-O-[hexyl-N-(5-thiocarbonyl-3,6-dipivaloyl fluorescein) amino] uridine (0.21 grams, 0.19 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 mL piperidine and shaken 30 minutes. CPG is filtered off, washed thoroughly with dichloromethane, and again dried under vacuum. The extent of loading is then determined by spectrophotometric assay of dimethoxytrityl cation in 0.3 M p-toluenesulfonic acid at 498 nm.

EXAMPLE 17

Preparation of 5'-O-(dimethoxytrityl)-2'-O-[hexyl-N-(3-oxycarbonyl-cholesteryl)amino]uridine Nucleoside 5'-O-(dimethoxytrityl)-2'-O-[hexylamino]-uridine (3.85 g, 6.0 mmol) was dissolved in anhydrous pyridine/dichloromethane 50/50 (v/v) (20 mL). Cholesteryl chloroformate (Fluka, 3.0 g, 6.68 mmol) was dissolved in anhydrous dichloromethane (20 ml) and added slowly under argon with a syringe to the stirring reaction mixture. The mixture was stirred under argon at room temperature for 2 h after which it was concentrated in vacuo. Residual DMF was coevaporated with toluene. The residue was dissolved in dichloromethane (50 mL) and washed with an equal volume saturated $NaHCO_3$. The aqueous layer was washed with dichloromethane and the combined organic extracts washed with an equal volume saturated NaCl. The aqueous layer was washed with dichloromethane and the combined organic layers dried over $MgSO_4$ and concentrated. The residue was chromatographed on a silica gel column with a gradient of 25% ethyl acetate in hexanes to 100% ethyl acetate. The desired product (3.78 g, 60%) eluted with 100% ethyl acetate ($R_f$ 0.41 by TLC).

EXAMPLE 18

Preparation of 5'-O-(dimethoxytrityl)-2'-O-[hexyl-N-(3-oxycarbonyl-cholesteryl)amino]uridine-3'-O-[2-cyanoethyl-N,N-diisopropyl]phosphoramidite Nucleoside 5'-O-(dimethoxytrityl)-2'-O-[hexyl-N-(3-oxy-carbonyl-cholesteryl)amino]uridine (3.44 g, 3.3 mmol) was dissolved in dry dichloromethane (75 mL). 2-cyanoethyl N,N,N'N'-tetraisopropylphosphorodiamidite (Sigma, 2.1 ml, 6.6 mmol) and diisopropylamine tetrazolide (0.29 g, 1.7 mmol) were added to the mixture, which was stirred under argon for 16 H. Dichloromethane (75 mL) was added to the solution, which was washed with an equal volume of saturated NaHCO$_3$. The aqueous layer was washed with an equal volume of dichloromethane. The aqueous layer was washed with dichloromethane (30 ml) and the combined organic layers washed with an equal volume of saturated NaCl. The aqueous layer was washed with dichloromethane (30 mL) and the combined organic layers dried over Mg$_2$SO$_4$ and concentrated in vacuo. The residue was chromatographed on a silica gel column with a gradient of 25% ethyl acetate in hexanes to 70% ethyl acetate. The desired product (3.35 g, 82% yield, R$_f$=0.71 by TLC in 50% ethyl acetate in hexanes) eluted with 50% ethyl acetate.

EXAMPLE 19

Preparation of 5'-O-(dimethoxytrityl)-2'-O-[hexyl-N-(3-oxycarbonyl-cholesteryl)amino]uridine-3'-O-(succinyl aminopropyl)-controlled pore glass Succinylated and capped controlled pore glass (0.3 grams) is added to 2.5 ml anhydrous pyridine in a 15 ml pear-shaped flask. DEC (0.07 grams, 0.36 mmol), TEA (100 µl, distilled over CaH$_2$), DMAP (0.002 grams, 0.016 mmol) and 5'-O-(dimethoxytrityl)-2'-O-[hexyl-N-(3-oxycarbonyl-cholesteryl)-amino]uridine (0.25 grams, 0.23 mmol) are added under argon and the mixture shaken mechanically for 16 hours. More nucleoside (0.20 grams) is added and the mixture shaken an additional 18 hours. Pentachlorophenol (0.03 grams, 0.11 mmol) is added and the mixture shaken 9 hours. CPG is filtered off and washed successively with dichloromethane, triethylamine, and dichloromethane. CPG is then dried under vacuum, suspended in 10 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm as approximately 39 µmol/g.

EXAMPLE 20

Preparation of 5'-O-(dimethoxytrityl)-2'-O-[hexyl-N-(2,4-dinitrophenyl)amino]uridine 5'-O-(dimethoxytrityl)-2'-O-(hexylamino)uridine (0.88 grams, 1.37 mmol) was dissolved in methanol (20 mL). 2,4-Dinitrofluorobenzene (DNFB, 0.25 grams, 1.37 mmol) was added and the mixture shaken on a mechanical shaker. The reaction was monitored by TLC. After 90 min, another 0.25 grams of DNFB was added and the reaction mixture shaken an additional 30 min, followed by addition of another 0.25 grams of DNFB. After shaking 2.5 hours, the mixture was concentrated in vacuo and chromatographed on a silica gel column, eluting with a gradient of 25% ethyl acetate in hexanes to 100% ethyl acetate. The desired product (0.51 grams, 46%) eluted with 100% ethyl acetate (R$_f$ 0.85 by TLC).

EXAMPLE 21

Preparation of 5'-O-(dimethoxytrityl)-2'-O-[hexyl-N-(2,4-dinitrophenyl)amino]uridine-3'-O-(2-cyanoethyl-N,N-diisopropyl)phosphoramidite 5'-O-(dimethoxytrityl)-2'-O-[hexyl-N-(2,4-dinitrophenyl) amino]uridine (0.45 grams, 0.55 mmol) was dissolved in dry dichloromethane (12 mL). 2-Cyanoethyl N,N,N',N'-tetraisopropylphosphorodiamidite (380 µL, 1.2 mmol) and diisopropylamine tetrazolide (0.041 grams, 0.024 mmol) were added to the mixture, which was stirred under argon for 16 hours. The reaction mixture was then concentrated in vacuo and the residue dissolved in dichloromethane (75 mL) followed by washing with an equal volume of saturated NaHCO$_3$. The aqueous layer was washed with dichloromethane (25 mL) and the combined organic layers washed with an equal volume of saturated NaCl. The aqueous layer was washed with dichloromethane (25 mL) and the combined organic layers dried over MgSO$_4$ and concentrated. The residue was chromatographed on a silica gel column, eluting with a gradient of 20% ethyl acetate in hexanes to 100% ethyl acetate. The desired product (510 mg foam, 93% yield, R$_f$ 0.70 by TLC) eluted with 100% ethyl acetate. $^{31}$PNMR (CDCl$_3$): 150.56 and 150.82 ppm.

EXAMPLE 22

Preparation of 5'-O-(dimethoxytrityl)-2'-O-[hexyl-N-(2,4-dinitrophenyl)amino]uridine-3'-O-(succinyl aminopropyl) controlled pore glass Succinylated and capped controlled pore glass (0.3 grams) is added to 3 ml anhydrous pyridine in a 50 ml round-bottom flask. DEC (0.12 grams, mmol), TEA (25 µl, distilled over CaH$_2$), DMAP (0.005 grams, 0.041 mmol) and 5'-O-(di-methoxytrityl)-2'-O-[hexyl-N-(2,4-dinitrophenyl) amino]uridine (0.21 grams, 0.26 mmol) are added under argon and the mixture shaken mechanically for 19 hours. More nucleoside (0.025 grams) is added and the mixture shaken an additional 5.5 hours. Pentachlorophenol (0.045 grams, 0.16 mmol) is added and the mixture shaken 18 hours. CPG is filtered off and washed successively with dichloromethane, triethylamine, and dichloromethane. CPG then is dried under vacuum, suspended in 15 ml piperidine and shaken for 15 minutes. CPG is filtered off, washed thoroughly with dichloromethane, and again dried under vacuum. The extent of loading is determined by spectrophotometric assay of dimethoxytrityl cation in 0.3 M p-toluenesulfonic acid at 498 nm, as approximately 29 µmol/gm.

EXAMPLE 23

Preparation of 5'-O-(dimethoxytrityl)-2'-O-[hexyl-N-(Nα-Nimid-Di-FMOC-L-Histidyl)amino]uridine Nucleoside 5'-O-(dimethoxytrityl)-2'-O-(hexylamino)-uridine (0.97 g, 1.51 mmol) was dissolved in dichloromethane (25 mL) and cooled to 0° C. in an ice bath. Nα,Nimid-Di-FMOC-L-histine pentafluorophenyl ester (2.4 g, 3.1 mmol, purchased from Sigma) and 1-hydroxybenzotriazole (0.32 g, 0.24 mmol, purchased from Fluka) were added to the stirred reaction mixture stirred under argon. After 15 minutes, the ice bath was removed and the mixture stirred under argon at room temperature for 72 h. The mixture was concentrated in vacuo and chromatographed on a silica gel column, eluting with a gradient of 50% ethyl acetate in hexanes to 70% ethyl acetate in hexanes. The desired product (0.53 g, 28%) eluted with 70% ethyl acetate (R$_f$ 0.53 by TLC in 100% ethyl acetate).

EXAMPLE 24

Preparation of 5'-O-(dimethoxytrityl)-2'-O-[hexyl-N-(Nα-Nimid-FMOC-L-histidyl)-amino]-uridine-3'-O-[2-cyanoethyl-N,N-diisopropyl]phosphoramidite 5'-O-Dimethoxytrityl-2'-O-[hexyl-N-(Nα-Nimid-Di-FMOC-L-histidyl)amino]uridine (1.9 g, 1.6 mmol) is dissolved in dry dichloromethane (20 mL). 2-Cyanoethyl N,N,N',N'-tetraisopropylphosphorodiamidite (800 μL, 2.4 mmol) and diisopropylamine tetrazolide (0.090 grams, 0.52 mmol) are added to the mixture, which is stirred under argon for 20 hours. The reaction mixture then is concentrated in vacuo and the residue dissolved in dichloromethane (75 mL). The solution is washed with an equal volume of saturated NaHCO$_3$. The aqueous layer is washed with dichloromethane (20 mL) and the combined organic layers washed with an equal volume of saturated NaCl. The aqueous layer is washed with dichloromethane (20 mL) and the combined organic layers dried over MgSO$_4$ and concentrated. The residue is chromatographed on a silica gel column, eluting with a gradient of 50% ethyl acetate in hexanes to 100% ethyl acetate. The desired product elutes with 100% ethyl acetate.

EXAMPLE 25

Preparation of 5'-O-(dimethoxytrityl)-2'-O-[hexyl-N-(Nα-Nimid-Di-FMOC)-L-histidyl)amino]uridine-3'-O-[succinylaminopropyl] controlled pore glass Succinylated and capped controlled pore glass (dried under vacuum for 3 hours immediately before use; 0.3 grams) is added to 3 ml anhydrous pyridine in a 50 ml round-bottom flask. DEC (0.12 grams, 0.63 mmol), TEA (25 μl, distilled over CaH$_2$), DMAP (0.005 grams, 0.04 mmol) and 5'-O-(dimethoxytrityl)-2'-O-[hexyl-N-(Nα-Nimid-Di-FMOC)-L-histidyl) amino]-uridine (0.21 grams, 0.17 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm. to be approximately 27 μmol/g.

EXAMPLE 26

Preparation of 5'-O-(dimethoxytrityl)-2'-O-[hexyl-N-(Ω-methyl-polyethylene glycol-propionoyl) amino]uridine Nucleoside 5'-O-(dimethoxytrityl)-2'-O-[hexylamino]-uridine, (1 g, 1.55 mmol) is dissolved in anhydrous DMF (15 mL). 1-Hydroxybenzotriazole (0.24 g, 1.75 mmol) and polyethylene glycol-propionic acid-NHS-ester (1.23 g, 1.75 mmol) are added to the reaction mixture. The mixture is stirred under argon at room temperature for 2 hours after which it is concentrated in vacuo. Residual DMF is coevaporated with toluene. The residue is dissolved in dichloromethane (50 mL) and then washed with an equal volume of saturated NaHCO$_3$. The aqueous layer is washed with dichloromethane and the combined organic extracts washed with an equal volume saturated NaCl. The aqueous layer is washed with dichloromethane and the combined organic layers dried over MgSO$_4$ and concentrated. The residue is chromatographed on a silica gel column, eluting with a gradient of 50% ethyl acetate in hexanes to 100% ethyl acetate. The desired product (1.08 g, 58%) eluted with 100% ethyl acetate.

EXAMPLE 27

Preparation of 5'-O-(dimethoxytrityl)-2'-O-[hexyl-N-(Ω-methyl-polyethylene glycol-propionoyl) amino]uridine-3'-O-(2-cyanoethoxy-N,N-diisopropyl)phosphoramidite 5'-O-(Dimethoxytrityl)-2'-O-[hexyl-N-(Ω-methyl-polyethylene glycol-propionoyl)amino]uridine (1.04 grams, 0.87 mmol) is dissolved in dry dichloromethane (20 mL). 2-Cyano-ethyl N,N,N',N'-tetraisopropylphosphorodiamidite (800 μL, 2.4 mmol) and diisopropylamine tetrazolide (0.090 grams, 0.52 mmol) are added to the mixture, which is stirred under argon for 20 hours. The reaction mixture then is concentrated in vacuo and the residue dissolved in dichloromethane (75 mL). The solution is washed with an equal volume of saturated NaHCO$_3$. The aqueous layer is washed with dichloromethane (20 mL) and the combined organic layers washed with an equal volume of saturated NaCl. The aqueous layer is washed with dichloromethane (20 mL) and the combined organic layers dried over MgSO$_4$ and concentrated. The residue is chromatographed on a silica gel column, eluting with a gradient of 50% ethyl acetate in hexanes to 100% ethyl acetate. The desired product elutes with 100% ethyl acetate.

EXAMPLE 28

Preparation of 5'-O-(dimethoxytrityl)-2'-O-[hexyl-N-(Ω-methyl-polyethylene glycol-propionoyl) amino]uridine-3'-O-(succinylaminopropyl) controlled pore glass Succinylated and capped controlled pore glass (CPG) is dried under vacuum for 3 hours immediately before use. Controlled pore glass (0.3 grams) is added to 3 ml anhydrous pyridine in a 50 ml round-bottom flask. DEC (0.12 grams, 0.67 mmol), TEA (25 μl, distilled over CaH$_2$), DMAP (0.005 grams, mmol) and 5'-O-(dimethoxytrityl)-2'-O-[hexyl-N-(w-methyl-polyethylene glycol-propionoyl)amino]uridine (0.21 grams, 0.175 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG then is dried under vacuum, suspended in 15 ml piperidine, and shaken 15 minutes. CPG is filtered off, washed thoroughly with dichloromethane, and again dried under vacuum. The extent of loading is determined by spectrophotometric assay of dimethoxytrityl cation in 0.3 M p-toluenesulfonic acid at 498 nm. to be approximately 18 μmol/g.

EXAMPLE 29

Preparation of Macrocycle Derivatized Nucleoside

5'-O-(dimethoxytrityl)-2'-O-(hexylamine)uridine is treated as per the procedure of Example 3 with the macrocycle 4-{1,4,8,11-tetraza-[tri-(trifluoroacetyl)cyclotetradec-1-yl]}methyl benzoic acid-N-hydroxy succinimide ester (prepared according to Simon Jones, et. al., *Bioconjugate Chem.* 1991, 2, 416) to yield the product.

EXAMPLE 30

Preparation of Macrocycle Derivatized Uridine Phosphoramidite

The nucleoside product of Example 29 is treated as per the procedure of Example 4 to yield the product.

EXAMPLE 31

Preparation of CPG Derivatized with Macrocycle Derivatized Nucleoside

The nucleoside product of Example 29 is treated as per the procedure of Example 5 to yield the product.

EXAMPLE 32

Preparation of 5'-O-(dimethoxyltrityl)-2'-O-(hexyl-N-(folate)-amino)uridine

5'-O-(Dimethoxytrityl)-2'-O-(hexylamine)uridine is treated as per the procedure of Example 3 with folic acid pentafluorophenyl ester (protected with an isobutyryl protecting group) to yield the product.

EXAMPLE 33

Preparation of 5'-O-(dimethoxyltrityl)-2'-O-[hexyl-N-(folate)-amino]uridine-3'-O-(2-cyanoethoxy-N,N-diisopropyl)phosphoramidite The nucleoside product of Example 29 is treated as per the procedure of Example 4 to yield the product.

EXAMPLE 34

Preparation of CPG derivatized with 5'-O-(dimethoxyltrityl)-2'-O-(hexyl-N-(folate)amino)uridine nucleoside The nucleoside product of Example 32 is treated as per the procedure of Example 5 to yield the product.

EXAMPLE 35

Preparation of 5'-O-(dimethoxytrityl)-2'-O-{hexyl-N-[2-methoxy-6-chloro-9(Ω-amino-caproyl)acridine]amino}uridine 6,9-Dichloro-2-methoxyacridine (Aldrich, 10 g, 36 mmol) and phenol (2.5 g) were placed together on a round-bottom flask with a stirring bar and to this 6-amino-hexanoic acid (9.3 g, 71 mmol) was added and the flask was heated to 100° (oil bath) for 2 hours. TLC (10% methanol in methylene chloride) showed complete disappearance of starting material. The reaction mixture was cooled and poured into 200 mL of methanol. The product isolates out as a yellow solid (about 10 g). This compound was then converted into its pentafluorophenyl ester.

5'-O-(Dimethoxytrityl)-2'-(hexylamino)uridine (0.5 g, 0.78 mmol) is dissolved in anhydrous DMF (15 mL). 1-Hydroxybenzotriazole (0.16 grams, 1.17 mmol) and 2-methoxy-6-chloro-9-(Ω-caproyl-amino) acridine pentafluorophenyl ester (0.53 grams, 1.17 mmol) are added to the reaction mixture. The mixture is stirred under argon at room temperature for 2 h, after which it is concentrated in vacuo. Residual DMF is coevaporated with toluene. The residue is dissolved in dichloromethane (50 mL) and washed with an equal volume saturated NaHCO₃. The aqueous layer is washed with dichloromethane and the combined organic extracts washed with an equal volume saturated NaCl. The aqueous layer is washed with dichloromethane and the combined organic layers dried over MgSO₄ and concentrated. The residue is chromatographed on a silica gel column, eluting with a gradient of 50% ethyl acetate in hexanes to 100% ethyl acetate. The desired product elutes with 100% ethyl acetate.

EXAMPLE 36

Preparation of 5'-O-(dimethoxytrityl)-2'-O-{hexyl-N-[2-methoxy-6-chloro-9-(Ω-amino-caproyl) acridine]amino}uridine-3'-O-(2-cyanoethyl-N-N-diisopropyl) phosphoramidite 5'-O-Dimethoxytrityl-2'-O-{hexyl-N-[2-methoxy-6-chloro-9-(w-amino-caproyl)acridine]amino}uridine (0.80 grams, 0.77 mmol) is dissolved in dry dichloromethane (20 mL). 2-Cyanoethyl N,N,N',N'-tetraisopropylphosphorodiamidite (800 µL, 2.4 mmol) and diisopropylamine tetrazolide (0.090 grams, 0.52 mmol) are added to the mixture, which is stirred under argon for 20 hours. The reaction mixture is then concentrated in vacuo and the residue dissolved in dichloromethane (75 mL). The solution is washed with an equal volume of saturated NaHCO₃. The aqueous layer is washed with dichloromethane (20 mL) and the combined organic layers washed with an equal volume of saturated NaCl. The aqueous layer is washed with dichloromethane (20 mL) and the combined organic layers dried over MgSO₄ and concentrated. The residue is chromatographed on a silica gel column, eluting with a gradient of 50% ethyl acetate in hexanes to 92% ethyl acetate. The desired product elutes with 100% ethyl acetate.

EXAMPLE 37

Preparation of 5'-O-(dimethoxytrityl)-2'-O-{hexyl-N-[2-methoxy-6-chloro-9-(Ω-aminocaproyl)acridine]amino}uridine-3'-O-(succinyl aminopropyl) controlled pore glass Succinylated and capped controlled pore glass (0.3 grams) is added to 3 ml anhydrous pyridine in a 50 ml round-bottom flask. DEC (0.12 grams, 0.67 mmol), TEA (25 µl, distilled over CaH₂), DMAP (0.005 grams, 0.04 mmol) and 5'-O-dimethoxytrityl-2'-O-{hexyl-N-[2-methoxy-6-chloro-9-(Ω-aminocaproyl)acridine]amino}uridine (0.21 grams, 0.17 mmol) are added under argon and the mixture shaken mechanically for 19 hours. More nucleoside (0.025 grams) is added and the mixture shaken an additional 5.5 hours. Pentachlorophenol (0.045 grams, 0.17 mmol) is added and the mixture shaken 18 hours. CPG is filtered off and washed successively with dichloromethane, triethylamine, and dichloromethane. CPG is then dried under vacuum, suspended in 15 ml piperidine and shaken 15 minutes. CPG is filtered off, washed thoroughly with dichloromethane and again dried under vacuum. The extent of loading is determined by spectrophotometric assay of dimethoxytrityl cation in 0.3 M p-toluenesulfonic acid at 498 nm. to be approximately 27 μmol/g.

EXAMPLE 38

Preparation of 5'-O-(dimethoxytrityl)-2'-O-[(hexyl-N,N-dimethyl)amino]uridine

5'-O-(dimethoxytrityl)-2'-O-(hexylamino)uridine (0.19 grams, 0.29 mmol) is dissolved in 4 ml methanol. Sodium acetate pH 4.0 (2 ml), sodium cyanoborohydride (0.02 grams, 0.3 mmol) and 37% formaldehyde in water (300 μl) are added to the reaction mixture, which is stirred 2 hours, after which it is concentrated in vacuo. The residue is dissolved in dichloromethane (50 mL) and washed with an equal volume saturated $NaHCO_3$. The aqueous layer is washed with dichloromethane and the combined organic extracts washed with an equal volume saturated NaCl. The aqueous layer is washed with dichloromethane and the combined organic layers dried over $MgSO_4$ and concentrated. The residue is chromatographed on a silica gel column, eluting with a gradient of 50% ethyl acetate in hexanes to 100% ethyl acetate. The desired product (0.15 grams, 80%) elutes with 10% Methanol-90% ethyl acetate.

EXAMPLE 39

Oligonucleotides Having 3'-Alkylamino Group

3'-O-Hexyl-(N-phthalimido)-aminouridine-CPG, i.e. the 5'-O-dimethoxytrityl-3'-O[hexyl-(Ω-N-phthalimido amino)]-uridine-2'-O-(succinyl-aminopropyl) controlled pore glass from Example 5, was used to synthesize the following oligonucleotides:

Oligomer 49: GAC U*

Oligomer 50 (SEQ ID NO:54): GCC TTT CGC GAC CCA ACA CU

Oligomer 51 (SEQ ID NO:55: GCC TTT CGC GAC CCA ACA CU* wherein "*" denotes the 3'-O hexylamino-modified nucleoside.

Standard commercial phosphoramidites were used with the synthesis cycle times specified by the manufacturer in a 380B ABI instrument (Applied Biosystems).

Oligomer 49 was used for structural proof of 3'-O-alkylamine-bearing oligonucleotides at the 3'-terminal end. It showed the expected three $^{31}$P NMR signals (−0.5 ppm, −0.25 ppm, −0,2 ppm) and seven lines in the trace aromatic base region in $^1$H NMR its spectrum.

Oligomer 51 was used to demonstrate the nuclease resistance offered by this the alkylamino group and also for further conjugation. The oligomer was treated with pyrene-butyric acid-N-hydroxy succinimide ester in 0.2 M $NaHCO_3$ buffer/DMF. The product, Conjugate 1, was purified by HPLC and size exclusion methods. HPLC retention times (eluting with a gradient of 5% $CH_3CN$ for 10 minutes then 5%–40% $CH_3CN$ for 50 minutes) were as follows:

| | Retention Time (min.) |
|---|---|
| Oligomer 50 | 25.99 |
| Oligomer 51 | 25.91 |
| Conjugate 1 | 49.35 |

The nuclease stability of oligomer 51 and the conjugate were tested against Oligomer 50 in HeLa cytoplasmic/nuclear extracts. The cell extract was diluted 1.4 times. The final concentration of oligonucleotide was 20 μM. The half lives of the oligonucleotides were as follows:

| | $t_{1/2}$ (hours) |
|---|---|
| Oligomer 50 | 1.0 |
| Oligomer 51 | 3.5 |
| Conjugate 1 | 3.6 |

The half life of phosphodiester Oligomer 50 increased 3–4 times by simple modification at the 3'-end with the hexylamino group, by itself, or by further conjugation.

EXAMPLE 40

Oligonucleotides Having 2'-O-Alkylamino Group

A. The phosphoramidite from Example 4,5'-O-(dimethoxytrityl)-2'-O-[hexyl-(Ω-N-phthalimido)amino]-uridine-3'-O-[(2-cyanoethyl)-N,N-diisopropyl]phosphoramidite was made as a 0.2 M solution in anhydrous $CH_3CN$ and used to synthesize the following oligonucleotides in an ABI DNA synthesizer, model 380 B. During the modified amidite coupling, the reaction time was increased to 10 minutes. A coupling efficiency of approximately 90% was observed. After deprotection with concentrated ammonium hydroxide (55° C., 16 hours) the oligonucleotides were purified by reverse phase HPLC and desalting column (Sephadex G-25).

Oligomer 52 (SEQ ID NO:14): GCGTGU*CTGCG

Oligomer 53: GAU*CT

B. GCGTGTU'CTGCG (SEQ ID NO:56) where U' is 2'-O-[hexyl-N-(1-pyrene-propyl-carbonyl)amino uridine, Conjugate 2 (Oligomer 52—pyrene butyrate conjugate).

To 20 O.D. of Oligomer 52 in 200 μL of 0.2 M $NaHCO_3$ buffer, 5 ml of pyrene-butyric acid-N-hydroxy succinimide ester in an Eppendorf tube was added followed by 200 μL of DMF. The tube was shaken overnight. The reaction was purified by size exclusion and HPLC to yield 18 O.D. of product.

C. GCGTGTU"CTGCG (SEQ ID NO:57) where U" is 2'-O-[6-bromoacetymido-hex-1yl]-uridine, Conjugate 3 (Oligomer 52—bromoacetate conjugate).

To 12 O.D. of Oligomer 52 in 100 μL of 0.2 M $NaHCO_3$ buffer, 2 mg bromoacetic acid-NHS ester (N-hydroxy succinimidyl bromoacetate) was added. After leaving the reaction to stand overnight, it was purified by size exclusion and HPLC to yield 7.5 O.D. of product.

D. GCGTGTUˆCTGCG (SEQ ID NO:58) where Uˆ is 2'-O-[hexyl-N-(polyethylene glycol)-propionoyl]amino uridine, Conjugate 4 (Oligomer 52—PEG conjugate).

To 24 O.D. of Oligomer 52 in 200 μL of 0.2 M $NaHCO_3$ buffer, 20 mg of Polyethylene glycol propionic acid-N- hydroxy succinimide ester was added. The reaction was mechanically shaken overnight and purified by Sephadex G-25 size exclusion and chromatography to yield 22 O.D. of product.

HPLC retention times (eluting with a gradient of 5% $CH_3CN$ for 10 minutes then 5%–40% $CH_3CN$ for 50 minutes in a C-18 Delta-Pak reverse phase column) were as follows:

|  | Retention Time (min.) |
|---|---|
| Oligomer 52 | 24.05 |
| Conjugate 2 | 40.80 |
| Conjugate 3 | 26.04 |
| Conjugate 4 | 55.58 |

Changes in $T_m$ due to pyrene conjugation were evaluated against both DNA and RNA. $T_m$ was measured in 100 mM $Na^+$, 10 nM phosphate, 0.1 mM EDTA, pH 7 at 4 µM strand concentration. The results were as follows:

|  | $T_m$ v. DNA (° C.) | $T_m$ v. RNA (° C.) |
|---|---|---|
| Oligomer 52 | 50.9 | 55.5 |
| Conjugate 2 | 55.3 | 55.5 |
|  | (4.4) | (0.0) |

The values in parentheses are changes in $T_m$ compared to amino linker in oligomer 52 as a control.

EXAMPLE 41

Oligonucleotide synthesis using
2'-O-hexylamino(pyrene-butyrate)uridine
phosphoramidite The amidite 5'-O-(dimethoxytrityl)-2'-O-[hexyl-N-(1-pyrene propyl carbonyl)amino]uridine-3'-O-(2-cyanoethyl-N,N-diisopropyl) phosphoramidite (0.2M in anhydrous acetonitrile) was used to synthesize the following oligomers, both for NMR studies:

Oligomer 54: GAU*CT
Oligomer 55: GCC GU*G TCG
(U*=2'-O-modified phosphoramidite)

These oligomers were purified trityl-on reverse-phase HPLC, detritylated in 80% acetic acid for one hour and then repurified by RP-HPLC and desalted by size-exclusion chromatography. NMR analysis showed the presence of pyrene peaks.

EXAMPLE 42

Oligonucleotide synthesis using
2'-O-hexylamino(dinitrophenyl)uridine
phosphoramidite The amidite 5'-O-(dimethoxytrityl)-2'-O-[hexyl-N-(2,4-dinitrophenyl)amino]uridine-3'-O-(2-cyanoethyl-N,N,-diisopropyl)phosphoramidite (0.18 M in anhydrous acetonitrile) was used to synthesize oligonucleotides, Oligomers 56 to 63. All are analogues of an ICAM antisense sequence. These oligomers purified trityl-on by RP-HPLC (Waters Delta-Pak $C_{18}$ column, 300 Å, 7.8 mm×30 cm, linear 50-min gradient of 5–60% acetonitrile in 0.05 M TEAA pH 7.3), detritylated in 80% acetic acid for one hour and then purified by RP-HPLC and desalted by size-exclusion chromatography. Data are summarized below:

|  | Backbone | Total (O.D.) | Retention Time (min) |
|---|---|---|---|
| Oligomer 56: GAU*CT | P = O | 40 | 39.16 |
| Oligomer 57: (SEQ ID NO:15) U*GG GAG CCA TAG CGA GGC# | P = S | 64 | 39.19 |
| Oligomer 58: (SEQIDNO:59) U*GG GAG CCA TAG CGA GGC | P = S | 45 | 39.21 |
| Oligomer 59: (SEQIDNO:60) U*GG GAG CCA TAG CGA GGC | P = O | 60 | 37.68 |
| Oligomer 60: (SEQIDNO:61) U*GG GAG CCA U*AG CGA GGC | P = O | 69 | 38.58 |
| Oligomer 61: TGG GAG CCA U*AG CGA GGC (SEQ ID NO:16) | P = O | 86 | 32.38 |
| Oligomer 62: U*CT GAG TAG CAG AGG AGC TC# (SEQ ID NO:17) | P = O | 34 | 35.76 |
| Oligomer 63: (SEQIDNO:62) U*GG GAG CCA U*AG CGA GGC# | P = S | 72 | 43.37 |

= Non-nucleoside 6-carbon amino linker (Glen Research) and Bold indicates nucleotides having 2'-O-methyl substitutions

EXAMPLE 43

Oligonucleotide synthesis using
2'-O-[hexylamino-(cholesterol)]uridine
phosphoramidite The amidite 5'-O-dimethoxytrityl-2'-O-[hexyl-N-(3-oxycarbonyl-cholesteryl)amino]uridine-3'-O-[2-cyanoethyl-N, N,-diisopropyl]-phosphoramidite (0.2M in anhydrous acetonitrile/dichloromethane 2:1 v/v) was used to synthesize Oligomers 67–74. These oligomers are purified trityl-on by reverse-phase HPLC (Waters Delta-Pak $C_{18}$, 300 Å, 7.8 mm×30 cm, linear 55-min gradient of 5–80% acetonitrile in 0.05 M TEAA pH 7.3), detritylated in 80% acetic acid for one hour and then repurified by RP-HPLC and desalted by size-exclusion chromatography. Data are summarized below:

|  | Backbone | Target | Retention Time (min) |
|---|---|---|---|
| Oligomer 67: GAU*CT | P = O | NMR | 52.73 |
| Oligomer 68: U*GG GAG CCA TAG CGA GGC (SEQIDNO:63) | P = O | ICAM | 49.64 |
| Oligomer 69: U*GC CCA AGC TGG CAT CCG TCA (SEQ ID NO:18) | P = S | ICAM | 51.98 |
| Oligomer 70: U*GC GTT TGC TCT TCT TCT TGC G (SEQ ID NO:19) | P = S | CMV | 52.57 |
| Oligomer 71: U*GC ATC CCC CAG GCC ACC AT (SEQ ID NO:20) | P = S | mseI-CAM | 53.24 |

-continued

| | Backbone | Target | Retention Time (min) |
|---|---|---|---|
| Oligomer 72:<br>U*CC CGC CTG TGA CAT GCA TT<br>(SEQ ID NO:21) | P = S | Raf | 53.95 |
| Oligomer 73:<br>GU*T CTC GCT GGT GAG TTT CA<br>(SEQ ID NO:22) | P = S | PKCa | 51.04 |
| Oligomer 74:<br>Fl-UU*GG GAG CCA TAG CGA GGC<br>(SEQ ID NO:23) | P = S | ICAM | 52.75 |

Fl-U = U 2'-modified with fluorescein (see Example 42).

EXAMPLE 44

Synthesis of oligonucleotides using
2'-O-[hexylamino-(fluorescein)]amidite

The amidite 5'-O-dimethoxytrityl-2'-O-[hexyl-N-(5-thiocarbonyl-3,6-dipivolyl fluorescein)amino]uridine-3'-O-(cyanoethyl-N,N-diisopropyl phosphoramidite) (0.2 M in anhydrous acetonitrile) was used to synthesize Oligomer 74 (above) and Oligomers 75–82 on a 1×10$^5$ (Oligomer 75) or 1×10$^2$ (remaining Oligomers) μmol scale. These oligomers are purified trityl-on by reverse phase HPLC (Waters Delta-Pak C$_{18}$, 300 Å, 7.8 mm×30 cm, linear gradient of acetonitrile in 0.05 M TEAA pH 7.3), detritylated in 80% acetic acid for one hour and then repurified by RP-HPLC and desalted by size-exclusion chromatography.

| | Backbone | Target |
|---|---|---|
| Oligomer 75:<br>GAU*CT | P = O | NMR |
| Oligomer 76:<br>U*GG GAG CCA TAG CGA GGC<br>(SEQIDNO:64) | P = O | ICAM |
| Oligomer 77:<br>U*GC CCA AGC TGG CAT CCG TCA<br>(SEQIDNO:65) | P = S | CAM |
| Oligomer 78:<br>U*GC CCA AGC TGG CAT CCG TCA#<br>(SEQIDNO:66) | P = S | ICAM |
| Oligomer 79:<br>U*GC GTT TGC TCT TCT TCT TGC G<br>(SEQIDNO:67) | P = S | CMV |
| Oligomer 80:<br>U*GC ATC CCC CAG GCC ACC AT<br>(SEQIDNO:68) | P = S | mseICAM |
| Oligomer 81: (SEQ ID NO:26)<br>U*GC ATC CCC CAG GCC ACC A<br>(U-CPG)<br>(U-CPG) = 2'-O-hexylphthalimido U 6 | P = S | mseICAM |
| Oligomer 82:<br>GU*T CTC GCT GGT GAG TTT CA<br>(SEQIDNO:69) | P = S | PKC |

Where U* is U modified with fluorescein.

EXAMPLE 45

1-Adamantane Acetic Acid Pentafluorophenyl Ester

1-Adamantane acetic acid (5 g, 25.77 mmol) was dissolved in 50 mL of CH$_2$Cl$_2$ and to this suspension pentafluorophenyl (5 g, 27.16 mmol) was added. Dicylohexylcarbodiimide (DCC) was then added (6 g, 29.12 mmol), at which point a highly exothermic reaction set in. The reaction flask was saturated with argon, sealed and then shaken in a wrist action shaker. After 5 hours the solution was filtered in a sintered glass funnel to filter off the dicylohexylurea formed during the reaction. The methylene chloride solution was evaporated and the pale yellow solid product (9 g, 97% crude product yield) obtained was used in the next condensation step.

EXAMPLE 46

5'-O-Dimethoxytrityl-2'-O-[hexyl-N-(1-adamantane acetamido)-amino]uridine

5'-O-Dimethoxytrityl-2'-O-(hexylamino)uridine (2 g, 3.15 mmol) was dissolved in 20 mL of methylene chloride. Adamantane acetic acid pentafluorophenyl ester (1.8 g from the previous step, 5 mmol crude product) was added followed by 3 mL of triethylamine. The reaction mixture was shaken for 4 hours in a wrist action shaker. TLC analysis (5% CH$_3$OH in CH$_2$Cl$_2$) showed the product formation as revealed by a moving trityl positive spot. When the amine at the origin was completely consumed (5 hours) the reaction mixture was evaporated and applied to a silica column loaded with chloroform solvent (20 cm×5 cm diameter). The column was eluted with chloroform (1 liter) followed by 5% CHCl$_3$ in CH$_3$OH. The material which showed trityl positive spots in TLC was pooled together and evaporated to give 2.5 g of the nucleoside-adamantane conjugate (98% yield). $^{13}$C analysis showed the presence of both uridine and adamantane residues. R$_f$=0.21 in 5% CH$_3$OH in CH$_2$Cl$_2$.

EXAMPLE 47

5'-O-Dimethoxytrityl-2'-O-[hexyl-N-(1-adamantane acetamido)-amino]uridine-3'-O-(2-cyanoethyl-N,N'-diisopropyl) Phosphoramidite 5'-O-Dimethoxytrityl-2'-O-[hexyl-N-(1-adamantane acetamido)amino]uridine (2.4 g, 2.96 mmol) was dissolved in 20 mL of CH$_2$Cl$_2$. To this solution 200 mg of diisopropylamino-tetrazolide (1.16 mmol) was added followed by 3.1 mL of 2-cyanoethyl-N,N,N',N'-tetraisopropyl phosphoramidite (9.45 mmol) was added under argon atmosphere. The mixture was stirred under argon overnight after which time TLC (5% CH$_3$OH/CH$_2$Cl$_2$) indicated almost complete conversion of nucleoside to its phosphoramidite. The reaction mixture was washed with saturated NaHCO$_3$ followed by saturated NaCl solution and then dried over anhydrous MgSO$_4$. The solution was evaporated and the foamy residue was purified in a silica column using 5% CH$_3$OH/CHCl$_3$ elution system to give the purified phosphoramidite (2 g, 67% yield). $^{31}$P NMR: 150.741, 150.49 ppm.

EXAMPLE 48

Oligonucleotide Synthesis with Adamantane Modified Amidite

5'-O-Dimethoxytrityl-2'-O-[hexyl-N-(1-adamantane acetamido)amino]uridine phosphoramidite was dissolved in anhydrous CH$_3$CN (100 mg of amidite for each 1 mL of solvent to give 0.1 M solution of the amidite). For the novel amidite the coupling time was extended by increasing the amidite and delivery time to 7.5 minutes and the waiting time to 6.0, thus a total of 13.5 minutes were used.

The oligonucleotides were deprotected and purified using the procedure described in Example 2. Table I summarizes the different oligonucleotides along with their HPLC retention times.

EXAMPLE 49

Table of Oligonucleotides Synthesized with their HPLC Retention Times-Incorporation of 2'-O-(CH$_2$)$_6$-NCHO-O-adamantylmethyl Uridine using amidite:

| SEQUENCE | BB | RT (min) | TARGET |
|---|---|---|---|
| U*T | P = O | a | NMR |
| GAU* CT | P = O | 29.3 | NMR |
| U*GG GAG CCA TAG CGA GGC (SEQIDNO:70) | P = O | a | ICAM |
| TGG GAG CCA U*AG CGA GGC (SEQIDNO:71) | P = O | 26.8 | ICAM |
| U*GC ATC CCC CAG GCC ACC (SEQIDNO:72) | P = S | 31.3/32.0 | mICAM |
| U*GC ATC CCC CAG GCC ACC AT-Fl (SEQIDNO:73) | P = S | 31.9 | mICAM |
| U* CAG TGC CTG CGC CGC GCT CG (SEQ ID NO:27) | P = S | 31.5/32.0 | Ki-ras |
| U* CC GTC ATC GCT CCT CAG GG (SEQ ID NO:28) | P = S | 31.6/32.1 | H-ras |
| U*CC CGC CTG TGA CAT GCA TT (SEQIDNO:74) | P = S | 31.8/32.3 | Raf | a not determined

HPLC conditions: Waters DeltaPak C-18 Delta Pak reverse-phase 15m 300 Å column, 3.9×300 mm size equipped with C-18 guard column; Solvent A: 50 mM TEAA, pH 7.0.; Solvent B: acetonitrile; Gradient: 0–10 min., 5% acetonitrile; 10–60 min., 5% to 60% acetonitrile linear increase.

EXAMPLE 50 cis-11-Eicosenoic Acid Pentafluorophenyl Ester cis-11-Eicosenoic acid (Aldrich, 2 g, 6.44 mmol) was dissolved in 50 mL of THF and to this suspension 1.2 g of pentafluorophenyl (6.5 mmol) was added followed by 1.33 g of DCC. The suspension was saturated with argon, sealed with a rubber septum and then shaken in a wrist action shaker. After 4 hours a clear pale yellow solution results with creamy white precipitate. The precipitated dicyclohexylurea was filtered off, washed with methylene chloride and the combined organic solution was evaporated to give the desired product as a waxy solid (3.25 g, crude product yield). This solid was used in the next condensation step without any further purification.

EXAMPLE 51

5'-O-Dimethoxytrityl-2'-O-[hexyl-N-(cis-11-eicosenoicamido)-amino]uridine

5'-O-Dimethoxytrityl-2'-O-(hexylamino)uridine (2 g, 3.15 mmol) was dissolved in 20 mL of methylene chloride. cis-11-Eicosenoic acid pentafluorophenyl ester (2.5 g from the previous step, 5 mmol crude product) was added followed by 3 mL of pyridine. The reaction mixture was shaken for 4 hours in a wrist action shaker. TLC analysis (5% CH$_3$OH in CH$_2$Cl$_2$) showed the product formation as revealed by a trityl positive spot above the origin. When the amine at the origin was completely consumed (5 hours) the reaction mixture was evaporated and applied to a silica column loaded with chloroform solvent (20 cm×5 cm diameter). The column was eluted with chloroform (1 liter) followed by 5% CHCl$_3$ in CH$_3$OH. The material which showed trityl positive spots in TLC was pooled together and evaporated to give 2.72 g of the nucleoside-eicosenoic acid conjugate (93% yield). $^{13}$C analysis showed the presence of both uridine and cis-11-eicosenoic acid residues. R$_f$=0.29 in 5% CH$_3$OH in CH$_2$Cl$_2$.

EXAMPLE 52

5'-O-Dimethoxtrityl-2'-O-[hexyl-N-(cis-11-eicosenoic amido) amino]uridine-3'-O-(2-cyanoethyl-N, N'-diisopropyl) Phosphoramidite The eicosenoic acid-uridine nucleoside from the previous step (2.5 g, 2.7 mmol) was dissolved in 20 mL of CH$_2$Cl$_2$. To this solution 200 mg of diisopropylaminotetrazolide (1.16 mmol) was added followed by 2.0 mL of 2-cyanoethyl-N,N,N',N'-tetraisopropyl phosphoramidite (6.1 mmol) was added under argon atmosphere. The mixture was stirred under argon overnight after which time TLC (5% CH$_3$OH/ CH$_2$Cl$_2$) indicated almost complete conversion of nucleoside to its phosphoramidite. The reaction mixture was washed with saturated NaHCO$_3$ followed by saturated NaCl solution and then dried over anhydrous MgSO$_4$. The solution was evaporated and the foamy residue was purified in a silica column using 5% CH$_3$OH/CHCl$_3$ elution system to give the purified phosphoramidite (2 g, 67% yield). As the phosphoramidite was contaminated with the H-phosphorate from the phosphitylating reagent, it was repurified in a silica column, by eluting with 8:2 EtOAc:Hexane to give 1.8 g (60% yield) of the phosphoramidite. $^{31}$P NMR: 150.74 and 150.56 ppm.

EXAMPLE 53

Oligonucleotide Synthesis with cis-11-eicosenoic acid modified amidite

5'-O-Dimethoxytrityl-2'-O-[hexyl-N-(cis-11-eicosenoic amido) amino] uridine phosphoramidite was dissolved in anhydrous CH$_3$CN (100 mg of amidite for each 1 mL of solvent to give 0.09 M solution of the amidite). For the novel amidite the coupling time was extended by increasing the amidite and delivery time to 7.5 minutes and the waiting time to 6.0, thus a total of 13.5 minutes were used.

The oligonucleotides were deprotected and purified using the procedure described in Example 2. Table II summarizes the different oligonucleotides along with their HPLC retention times.

EXAMPLE 54

Table of Incorporation of 2'-O-(CH$_2$)$_6$-NHCO-Cis-11-Eicosenoic U using amidite:

| SEQUENCE | BB | RT (min) | TARGET |
|---|---|---|---|
| U*T | P = O | a | NMR |
| GAU*CT | P = O | a | NMR |
| U*GG GAG CCA TAG CGA GGC (SEQIDNO:75) | P = O | a | ICAM |

-continued

Table of Incorporation of 2'-O-(CH$_2$)$_6$-NHCO-Cis-11-Eicosenoic U using amidite:

| SEQUENCE | BB | RT (min) | TARGET |
|---|---|---|---|
| TGG GAG CCA U*AG CGA GGC (SEQIDNO:76) | P = O | 17.8 | ICAM |
| U*GC ATC CCC CAG GCC ACC AT (SEQIDNO:77) | P = S | 55.5/56.4 | mICAM |
| U*GC ATC CCC CAG GCC ACC AT-Fl (SEQIDNO:78) | P = S | 56.3/57.3 | mICAM |
| U* CAG TGC CTG CGC CGC GCT CG (SEQIDNO:79) | P = S | a | Ki-ras |
| U* CC GTC ATC GCT CCT CAG GG (SEQIDNO:80) | P = S | 57.0/57.8 | H-ras |
| U*CC CGC CTG TGA CAT GCA TT (SEQIDNO:81) | P = S | 57.1/57.9 | Raf | a not determined

HPLC conditions: Waters DeltaPak C-18 Delta Pak reverse-phase15m 300 A column, 3.9×300 mm size equipped with C-18 guard column; Solvent A: 50 mM TEAA, pH 7.0.; Solvent B: acetonitrile; Gradient: 0–10 min., 5% acetonitrile; 10–60 min., 5% to 60% acetonitrile linear increase.

EXAMPLE 55

5'-O-Dimethoxytrityl-2'-O-(hexyl-N-(N-biotinyl-6-aminocaproyl)amino]uridine

5'-O-Dimethoxytrityl-2'-O-(hexylamino)uridine (1.05 g, 1.66 mmol) was dissolved in 20 mL of methylene chloride. N-Biotinyl-6-amino caproic acid (0.75 g, Fluka, 1.65 mmol) was added followed by 1 mL of pyridine. The reaction mixture was shaken for 4 hours in a wrist action shaker. The white suspension of the biotin reagent completely dissolved into solution by this time, TLC analysis (5% CH$_3$OH in CH$_2$CO$_2$) showed the product formation as revealed by an upper trityl positive spot above the origin. When the amine at the origin was completely consumed (5 hours) the reaction mixture was evaporated and applied to a silica column loaded with chloroform solvent (20 cm×5 cm diameter). The column was eluted with chloroform (1 liter) followed by 5% CHCl$_3$ in CH$_3$OH (1 liter), then followed by 10% CH$_3$OH in CHCl$_3$. The material, which elutes out with 10% CH$_3$OH, showed trityl positive spots in TLC was pooled together and evaporated to give 1.53 g of the nucleoside-biotin conjugate (98% yield). $^{13}$C analysis showed the presence of both uridine and biotin residues. R$_f$=0.214 in 10% CH$_3$OH in CH$_2$Cl$_2$.

EXAMPLE 56

5'-O-Dimethoxytrityl-2'-O-[hexyl-N-(N-biotinyl-6-aminocaproyl)amino]uridine 3'-O-(2-cyanoethyl-N,N'-diisopropyl) Phosphoramidite The biotin-uridine nucleoside from the previous step was dissolved in 20 mL of CH$_2$Cl$_2$. To this solution 100 mg of diisopropylaminotetrazolide (0.58 mmol) was added followed by 1.0 mL of 2-cyanoethyl-N,N,N',N'-tetraisopropyl phosphoramidite (3.05 mmol) was added under argon atmosphere. The mixture was stirred under argon overnight after which time TLC (5% CH$_3$OH/CH$_2$Cl$_2$) indicates almost complete conversion of nucleoside to its phosphoramidite. The reaction mixture was washed with saturated NaHCO$_3$ followed by saturated NaCl solution and then dried over anhydrous MgSO$_4$. The solution was evaporated and the foamy residue was purified in a silica column using 100% ethyl acetate elution system to give the purified phosphoramidite.

EXAMPLE 57

5-O-Dimethoxytrityl-3'-O-[hexyl-N-(N-biotinyl-6-aminocaproyl)-amino]uridine

5'-O-Dimethoxytrityl-3'-O-(hexylamino)uridine (0.53 g, 0.83 mmol) was dissolved in 10 mL of methylene chloride. N-Biotinyl-6-aminocaproic acid (0.75 g, Fluka, 1.65 mmol) was added followed by 0.5 mL of pyridine. The reaction mixture was shaken for 4 hours in a wrist action shaker. The white suspension of the biotin reagent was completely dissolved into solution by this time. TLC analysis (10% CH$_3$OH in CH$_2$Cl$_2$) showed the product formation as revealed by an upper trityl positive spot above the origin. When the amine at the origin was completely consumed (5 hours) the reaction mixture was evaporated and applied to a silica column loaded with chloroform solvent (20 cm×5 cm diameter). The column was eluted with chloroform (1 liter) followed by 5% CHCl$_3$ in CH$_3$OH (1 liter). The material, which elutes out with 10% CH$_3$OH, showed trityl positive spots in TLC was pooled together and evaporated to give 0.6 g of the nucleoside-biotin conjugate and biotin residues. R$_f$=0.21 in 10% CH$_3$OH in CH$_2$Cl$_2$.

EXAMPLE 58

5'-O-Dimethoxytrityl-3'-O-[hexyl-N-(N-biotinyl-6-aminocaproyl)amino]uridine-2'-O-(succinylaminopropyl) Controlled Pore Glass Succinylated/capped aminopropyl controlled pore glass was dries under vacuum for 3 hours immediately before use. A portion (0.3 g, 24 µmol) was added to 3 mL anhydrous pyridine in a 50 mL round-bottom flask. DEC (0.12 g, 0.63 mmol), TEA (25 µL, distilled over CaH$_2$). DMAP (0.005 g, 40 µmol) and 5'-O-(dimethoxytrityl)-3'-O-[hexyl-N-(N-biotinyl-6-aminocaproyl) amino]uridine (0.22 g, 0.22 mmol) were added under argon and the mixture shaken mechanically for 19 hours. More nucleoside (0.025 g) was added and the mixture shaken for an additional 5.5 hours. Pentachlorophenol (0.045 g, 0.168 mmol) was add and the mixture shaken for 18 hours. CPG was filtered off and washed successively with dichloromethane, triethylamine, and dichloromethane. The resulting CPG was then dried under vacuum, suspended in 15 mL piperidine and shaken 30 minutes. CPG was filtered off, washed thoroughly with dichloromethane and again dried under vacuum. The extent of loading (determined by spectrophotometric assay of dimethoxytrityl cation in 0.3 M p-toluenesulfonic acid at 498 nm) was approximately 36 µmol/g. The product solid support was subsequently used to synthesize the oligomers, containing biotin at the 3' nucleotide unit.

EXAMPLE 59

Oligonucleotide Synthesis with Biotin Modified Amidite and Control Pore Glass

5'-O-Dimethoxytrityl-3'-O-[hexyl-N-(N-biotinyl-6-aminocaproyl)amino]uridine nucleoside phosphoramidite was dissolved in anhydrous CH$_3$CN (100 mg of amidite for each 1 mL of solvent to give 0.08–0.09 M solution of the amidite). For the novel amidite the coupling time was extended by increasing the amidite and delivery time to 7.5 minutes and the waiting time to 6.0, thus a total of 13.5 minutes were used.

The oligonucleotides were deprotected and purified using the procedure described in Example 2. The controlled pore glass containing biotin was used to synthesize 3'-biotin containing oligonucleotides.

EXAMPLE 60

1-2-Di-O-hexadecyl-rac-glycerol-succinimidyl-carbonate 1,2-Di-O-hexadecyl-rac-glycerol (2 g, 3.69 mmol) was dissolved in 3 mL of CH$_2$Cl$_2$ and to this solution disuccinimidyl carbonate (DSC) (1.42 g, 5.54 mmol) was added. Triethylamine was then added (2 mL, 14.3 mmol), followed by 20 mL of anhydrous acetonitrile. The reaction flask was saturated with argon, sealed and then shaken in a wrist action shaker. After 8 hours the reaction mixture was evaporated. The residue was dissolved in CH$_2$Cl$_2$ (100 mL), washed with saturated NaHCO$_3$ solution followed by saturated NaCl solution and the organic layer was dried over anhydrous MgSO$_4$. The solid residue (3.5 g) was used in the next step to condense with the amine. $^{13}$C NMR confirms the complete conversion of 1,2-di-O-hexadecyl-rac-glycerol to the corresponding succinimidyl carbonate.

EXAMPLE 61

5'-O-Dimethoxytrityl-2'-O-[hexyl-N-(carbonoyl 1,2-di-O-hexadecyl-rac-glycerol)amino]uridine 5'-O-Dimethoxytrityl-2'-O-(hexylamino)uridine (2 g, 3.15 mmol) was dissolved in 20 mL of methylene chloride. 1,2-Di-O-hexadecyl-rac-glycerol succinimidyl carbonate (3.0 g from the previous step, 5 mmol crude product) was added followed by 3 mL of pyridine. The reaction mixture was shaken for 4 hours in a wrist action shaker. TLC analysis (5% CH$_3$OH in CH$_2$Cl$_2$) showed the product formation as revealed by a moving trityl positive spot. When the amine at the origin was completely consumed (5 hours) the reaction mixture was evaporated and applied to a silica column loaded with chloroform solvent (20 cm×5 cm diameter). The column was eluted with chloroform (1 liter) followed by 5% CHCl$_3$ in CH$_3$OH. The material which showed trityl positive spots in TLC was pooled together and evaporated to give 3.0 g of the nucleoside-lipid conjugate (98% yield). $^{13}$C analysis showed the presence of both uridine and lipid residues.

EXAMPLE 62

5'-O-Dimethoxytrityl-2'-O-[hexyl-N-(carbonoyl 1,2-di-O-hexadecyl-rac-glycerol-succinimidyl-carbonate]-3'-O-(2-cyanoethyl-N,N'-diisopropyl) Phosphoramidite The lipid-uridine nucleoside from the previous step was dissolved in 20 mL of CH$_2$Cl$_2$. To this solution 200 mg of diisopropylaminotetrazolide (1.16 mmol) was added followed by 1.55 mL of 2-cyanoethyl-N,N,N',N'-tetraisopropyl phosphoramidite (4.75 mmol) was added under argon atmosphere. The mixture was stirred under argon overnight after which time TLC (5% CH$_3$OH/CH$_2$Cl$_2$) indicated almost complete conversion of nucleoside to its phosphoramidite. The reaction mixture was washed with saturated NaHCO$_3$ followed by saturated NaCl solution and then dried over anhydrous MgSO$_4$. The solution was evaporated and the foamy residue was purified in a silica column using 5% CH$_3$OH/CHCl$_3$ elution system to give the purified phosphoramidite.

EXAMPLE 63

Oligonucleotide Synthesis with Lipid Modified Amidite

5'-O-Dimethoxytrityl-2'-O-[hexyl-N-(carbonoyl-1,2-di-O-hexadecyl-rac-glycerol)amino]uridine phosphoramidite was dissolved in anhydrous CH$_3$CN (100 mg of amidite for each 1 mL of solvent to give 0.08–0.09 M solution of the amidite). For the novel amidite the coupling time was extended by increasing the amidite and delivery time to 7.5 minutes and the waiting time to 6.0, thus a total of 13.5 minutes were used. The oligonucleotides were deprotected and purified using the procedure described in Example 2.

EXAMPLE 64

Oligonucleotide Synthesis

5'-O-Dimethoxytrityl-2'-O-[hexyl-N-(1-pyrene butyroyl) amino]uridine phosphoramidite was dissolved in anhydrous CH$_3$CN (100 mg of amidite for each 1 mL of solvent to give 0.08–0.09 M solution of the amidite). For the novel amidite the coupling time was extended by increasing the amidite and delivery time to 7.5 minutes and the waiting time to 6.0 minutes, hence using a total of 13.5 minutes.

The oligonucleotides were deprotected and purified using the procedure described in Example 2. The Table below summarizes the different oligonucleotides (ICAM, ras, raf and PKC-a oligonucleotides).

| Table of Incorporation of 2'-O-(CH$_2$)$_6$-NHCO-butyryl pyrene U using amidite | | | |
|---|---|---|---|
| SEQUENCE | BB | RT (min) | TARGET |
| U*T | P = O | 40.66 | NMR |
| U*GG GAG CCA TAG CGA GGC (SEQIDNO:82) | P = O | a | ICAM |
| TGG GAG CCA U*AG CGA GGC (SEQIDNO:83) | P = O | a | ICAM |
| U*GC ATC CCC CAG GCC ACC AT (SEQIDNO:84) | P = S | 30.00, 30.05 | mICAM |
| U*GC ATC CCC CAG GCC ACC AT-3'-aminolink (SEQIDNO:85) | P = S | 30.29, 31.25 | mICAM |
| U* CAG TGC CTG CGC CGC GCT CG (SEQIDNO:86) | P = S | 30.47, 31.32 | Ki-ras |
| U* CC GTC ATC GCT CCT CAG GG (SEQIDNO:87) | P = S | 30.90, 31.66 | H-ras |
| U*CC CGC CTG TGA CAT GCA TT (SEQIDNO:88) | P = S | 31.54/ 32.19 | Raf |
| U*GT TCT CGC TGG TGA GTT TCA (SEQIDNO:89) | P = S | 30.96/ 31.86 | PKC-a | a not determined

HPLC conditions: Waters DeltaPak C-4 Delta Pak reverse-phase15m 300 A column, 3.9×300 mm size equipped with C-18 guard column; Solvent A: 50 mM TEAA, pH 7.0.; Solvent B: acetonitrile; Gradient: 0–10 min., 5% acetonitrile; 10–60 min., 5% to 60% acetonitrile linear increase.

HPLC conditions: Waters DeltaPak C-4 Delta Pak reverse-phase15m 300 Å column, 3.9×300 mm size equipped with C-18 guard column; Solvent A: 50 mM TEAA, pH 7.0.; Solvent B: acetonitrile; Gradient: 0–10 min., 5% acetonitrile; 10–60 min., 5% to 60% acetonitrile linear increase.

EXAMPLE 65

Incorporation of 2'-O-$(CH_2)_6$—NHCO-cholesterol Uridine at 5'-End of Oligonucleotides Using Amidites Synthesis:

Oligonucleotides were synthesized on an Expedite Nucleic Acid Synthesis System (Millipore Corp., Bedford, Mass.). Two 1-µmol syntheses or a single 15 µmol synthesis was performed for each oligonucleotide. Standard DNA synthesis conditions were used except during coupling of the modified amidite which was accomplished as follows: The novel amidite was dissolved in $CH_2Cl_2/CH_3CN$ 50/50 (0.08–0.1M). For 10 µmol syntheses, a 6-min wait step was added to the coupling cycle, which was repeated once. For 1 µmol phosphodiester syntheses, the coupling step was also extended for 6 min, with periodic addition of fresh amidite. For 1 µmol phosphorothioate syntheses, the coupling step was extended for 13 min, with periodic addition of fresh amidite.

Purification:

After standard cleavage from CPG and deprotection (ammonium hydroxide at 55° C. for 16–24 hours), oligonucleotides were trityl-on purified by preparative HPLC to remove failure sequences. HPLC conditions: Waters Delta-Pak $C_4$ column, 7.8 mm×30 cm, 300 A, 15 u; 2.5 ml/min flow rate using a gradient of 5–80% AcCN in 50 mM triethylammonium acetate pH 7.0 over 50 min. Following lyophilization, oligonucleotides were detritylated for 45 min in 80% acetic acid and lyophilized again. Oligonucleotides were then further purified by size exclusion on G-25 columns to remove salts and the trityl group.

Analysis:

Except for 8002, oligonucleotides were analyzed by HPLC using a gradient analogous to the one above and a Waters Delta-Pak $C_4$ column (3.9 mm×30 cm) with a flow rate of 1.5 ml/min over 50 min. 8002 was analyzed using a gradient of 5–60% AcCN. Purified phosphorothioate oligonucleotides appeared as two peaks by HPLC, phosphodiesters as one peak. Oligonucleotides were further analyzed by electrophoresis on 20% polyacrylamide denaturing (7M urea) gels. All were predominantly single bands of the appropriate size compared to standards. Gel analysis of 8012 (loaded without any pretreatment) shows a very high band, presumably the tetrameric form of this oligonucleotide, plus a faint band where one would expect a monomeric 8mer+ cholesterol to run. (The parent compound, 5320, is known to form a G-quartet structure.) Some oligonucleotides were also analyzed by capillary electrophoresis. Selected oligonucleotides have been analyzed by electrospray mass spectrometry.

Results are shown in the following Table were * indicated site of selected modification.

| SEQUENCE | TYPE | HPLC RETENTION TIME (min) | TARGET |
|---|---|---|---|
| U*GGGAGCCATAGCGAGGC (SEQIDNO:90) | P = O | 54.65 | ICAM |
| U*GCCCAAGCTGGCATCCGTCA (SEQIDNO:91) | P = S | 45.77, 46.44 | ICAM |
| U*GCGTTTGCTCTTCTTCTTGCG (SEQIDNO:92) | P = S | 45.35, 46.03 | CMV |
| U*GCATCCCCCAGGCCACCAT (SEQIDNO:93) | P = S | 56.74, 57.65 | mICAM |
| U*CCCGCCTGTGACATGCATT (SEQIDNO:94) | P = S | 46.69, 47.25 | RAF |
| U*TTAGGATTCGTGCTCATGG (SEQ ID NO:29) | P = S | 47.71, 48,32 | HCV |
| U*GTTCTCGCTGGTGAGTTTCA (SEQ ID NO:30) | P = S | 46.78, 47.58 | $PKC_a$ |
| U*GGGAGCCATAGCGAGGC (SEQIDNO:95) | P = S | not det'd | HIV |
| U*TGGGGTT | P = S | 48.46, 49.04 | HIV |

EXAMPLE 66

Incorporation of 2'-O-$(CH_2)_6$—NHCO-cholesterol Uridine at nonterminal positions of oligonucleotides using amidite Oligonucleotides incorporating 2'-O-$(CH_2)_6$—NHCO-cholesterol at nonterminal (not at either the 5' or the 3' terminus of the oligonucleotide) were synthesized at a 1 µmol syntheses scale, analyzed and purified as per the procedures of Example 65.

Results are shown in the following Table were * indicated site of selected modification.

| SEQUENCE | TYPE | HPLC RETENTION TIME (min) | TARGET |
|---|---|---|---|
| TGGGAGCCAU*AGCGAGGC (SEQIDNO:96) | P = O | 42.21 | ICAM |
| GU*TCTCGCTGGTGAGTTTCA (SEQIDNO:97) | P = S | not det'd | $PKC_a$ |

EXAMPLE 67

Incorporation of 3'-O-$(CH_2)_6$—NHCO-cholesterol Uridine at 3' end of oligonucleotides using modified CPG Cholesterol-modified CPG was packed into screw-top CPG columns (Glen Research). Oligonucleotides were synthesized on a 1-µmol syntheses scale, analyzed and purified as in Example 65 except that standard DNA synthesis conditions were used for all couplings.

Results are shown in the following Table were * indicated site of selected modification.

| SEQUENCE | TYPE | HPLC RETENTION TIME (min) | TARGET |
|---|---|---|---|
| GCCTTTCGCGACCCAACACU* (SEQIDNO:98) | P = S | 48.37 | HCV |
| GCCTTTCGCGACCCAACACU* (SEQIDNO:99) | P = O | 50.18 | HCV |
| TGCATCCCCCAGGCCACCAU* (SEQ ID NO:31) | P = O | 47.01 | mICAM |
| GTGCTCATGGTGCACGGTCU* (SEQ ID NO:32) | P = S | 49.97 | HCV |
| TGCATCCCCCAGGCCACCAU* (SEQIDNO:100) | P = S | ~59.5 | mICAM |

EXAMPLE 68

Incorporation of 2'-O-$(CH_2)_6$—NHCO-cholesterol Uridine at 3' end of oligonucleotides using modified CPG Cholesterol-modified CPG was packed into screw-top CPG columns (Glen Research). Oligonucleotides were synthesized on a 1-µmol syntheses scale, analyzed and purified as in Example 65 except that standard DNA synthesis conditions were used for all couplings.

Results are shown in the following Table were * indicated site of selected modification.

| SEQUENCE | TYPE | HPLC RETENTION TIME (min) | TARGET |
|---|---|---|---|
| TGCATCCCCCAGGCCACCAU* (SEQIDNO:101) | P = O | 47.03 | ICAM |

EXAMPLE 69

Double Incorporation of Cholesterol by placement of(2'-O-$(CH_2)_6$—NHCO-cholesterol Uridine on 5' end and 3'-O-$(CH_2)_6$—NHCO-cholesterol Uridine on 3' end Cholesterol-modified CPG was packed into screw-top CPG columns (Glen Research). Oligonucleotides were synthesized on a 1-µmol syntheses scale, analyzed and purified as in Example 65 except that the extended coupling step for the cholesterol amidite (see Example 65) was repeated once.

Results are shown in the following Table were * indicated site of selected modification.

| SEQUENCE | TYPE | HPLC RETENTION TIME (min) | TARGET |
|---|---|---|---|
| U*GCATCCCCCAGGCCACCAU* (SEQ ID NO:33) | P = S | 54.31 | ICAM |
| U*GCATCCCCCAGGCCACCAU* (SEQIDNO:102) | P = O | 52.54 | ICAM |

EXAMPLE 70

Incorporation of Cholesterol and Aminohexyl Modifications into 2'F Chimeric Oligonucleotides The parent oligonucleotide, complementary to messenger RNA of PKCα, is a chimeric phosphorothioate oligonucleotide having a central deoxyribonucleotide region that is "flanked" on both the 5' and the 3' sides with region that have 2'-deoxy-2'-fluoro nucleotides. These compound are alternately referenced as "gapped" oligonucleotides. The central "gapped" regions are shown in underlines in the Table below with the "flanks" (or alternatively the "wings") shown in unmodified type.

The oligonucleotides were synthesized, analyzed and purified as in Example 65, except for the following: Concentration of all amidites was 0.1 M. Two 1-µmol syntheses were performed for each oligonucleotide. The coupling step was extended 6 min, with periodic addition of fresh amidite; this extended coupling step was repeated once for the cholesterol amidite coupling. Trityl-on HPLC purification of Compound ID #9532 was accomplished using a linear gradient of 5–40% AcCN over 50 min. After detritylation and purification by size-exclusion, it was analyzed using a similar analytical-scale HPLC procedure gel and capillary electrophoresis. Purified compound ID #9535 appears as two peaks by HPLC, others as one peak. Compound ID#s 9532 and 9534 contained undeprotected 3'-hexylamine; probably about 20% according to previous results (phthalimide is the protecting group).

$U_1$*=3'-O—$(CH_2)_6$—$NH_2$U
$U_2$*=3'-O—$(CH_2)_6$—NHCO-cholesterol U
$U_3$*=2'-O—$(CH_2)_6$—NHCO-cholesterol U Results are shown in the following Table were * indicated site of selected modification.

| SEQUENCE | HPLC RETENTION TIME (min) |
|---|---|
| UGUUCUCGCTGGTGAGUUUCAU (SEQ ID NO:34) | 34.5 |
| UGUUCUCGCTGGTGAGUUUCAU$_1$* (SEQIDNO:103) | not determined |
| UGUUCUCGCTGGTGAGUUUCAU$_2$* (SEQIDNO:104) | 48 |
| U$_3$*GUUCUCGCTGGTGAGUUUCAU$_2$* (SEQIDNO:105) | 46.5, 47.5 |
| U$_3$*GUUCUCGCTGGTGAGUUUCAU (SEQIDNO:106) | 46.5, 47.5 |

EXAMPLE 71

5'-O-Dimethoxytrityl-3'-O-[hexyl-(omega-N-phtalimido) amino] uridine-2'-O-(2-cyanoethyl-N,N-diisopropyl) Phosphoramidite The 5'-dimethoxytrityl-3'-O-[hexyl-(omega-N-phthalimido)amino]uridine (2 g, 2.6 mmol) was dissolved in 20 mL anhydrous $CH_2Cl_2$. To this solution diisopropylaminotetrazolide (0.2 g, 1.16 mmol) and 2.0 mL 2-cyanoethyl-N,N,N',N'-tetraisopropyl phosphoramidite (6.3 mmol) were added and stirred overnight. TLC (1:1 EtOAc/hexane) showed complete disappearance of starting material. The reaction mixture was transferred with $CH_2Cl_2$ and washed with saturated $NaHCO_3$ (100 mL), followed by saturated NaCl solution. The organic layer was dried over anhydrous Na$_2$SO$_4$ and evaporated to yield 3.8 g of a crude product, which was purified in a silica column (200 g) using 1:1 hexane/EtOAc to give 1.9 g (1.95 mmol, 74% yield) of the desired phosphoramidite.

| Sequence(3'→5') | Features of Sequence |
|---|---|
| GAU$_3$*CT | P = O, 2'-5' Linkage |
| GCG TGU$_3$* CTG GG (SEQ ID NO:35) | P = O, 2'-5' Linkage |
| GCG UGU$_3$* CUG CG (SEQ ID NO:36) | P = O, 2'-5' Linkage, Chimera having 2'-OMe flanks |

EXAMPLE 72

NMR and HPLC Analysis of 5'-3' versus 5'-2' Internucleotide Linkages and 2' substituents versus 3' substituents The 400 MHz $^1$H spectrum of oligomer d(GAU$_2$*CT), where U$_2$=2'-O-aminohexyluridine showed 8 signals between 7.5 and 9.0 ppm corresponding to the 8 aromatic protons. In addition, the anomeric proton of U* appears as a doublet at 5.9 ppm with J$_1$',$_2$'=7.5 Hz, indicative of C2'-endo sugar puckering. The corresponding 2'-5' linked isomer shows a similar structure with J$_1$',$_2$'=3.85 Hz at 5.75 ppm, indicating an RNA type sugar puckering at the novel modification site favorable for hybridization to an mRNA target. The proton spectrum of the oligomer d(GACU$_3$*), where U$_3$*=3'-O— hexylamine, showed the expected 7 aromatic proton signals between 7.5 and 9.0 ppm and the anomeric proton doublet at 5.9 ppm with J$_1$',$_2$'=4.4 Hz. This suggests more of a C3'-endo puckering for the 3'-O-alkylamino compounds compared to their 2' analogs. $^{31}$P NMR of these oligonucleotides showed the expected 4 and 3 signals from the internucleotide phosphate linkages for d(GAU*CT) and d(GACU*), respectively. 3'-5' linked vs. 2'-5' linked have different retention times in RP HPLC and hence different lipophilicities, implying potentially different extent of interactions with cell membranes.

EXAMPLE 73

2'-5' Internucleotide Linked Oligonucleotide Conjugation Chemistry

The oligonucleotides 9274 and 9518 (20 ODs each) were dried and re-dissolved in 0.2M NaHCO$_3$ buffer (200 μL) in an eppendorf tube. 5 mg of pyrene butyric acid-N-hydroxy succinimide ester was dissolved in 400 μL anhydrous DMF. 200 μL of this solution was added to each of the eppendorf tubes and vortexed and left to stand overnight. The reaction mixtures were passed through a g-25 column to remove the excess reagent, an then purified by Reverse-Phase HPLC. The retention times of the starting material and the conjugates are summarized below:

| Sequence (3'→5') | Retention Time (min) |
|---|---|
| GAU$_3$CT | 23.85 |
| GCG TGU$_3$* CTG GG (SEQIDNO:107) | 24.99 |
| pyrene conjugate of 9274 | 39.00 |
| pyrene conjugate of 9518 | 40.05 |

HPLC conditions: Waters DeltaPak C-18 Delta Pak reverse-phase15m 300 A column, 3.9×300 mm size equipped with C-18 guard column; Solvent A: 50 mM TEAA, pH 7.0; Solvent B: acetonitrile; Gradient: 0–10 min., 5% acetonitrile; 10–60 min., 5% to 40% acetonitrile linear increase.

EXAMPLE 74

Tm Analysis of 2'–5' v. 3'–5'Connected Oligonucleotides and their Conjugates

Thermal melts were done as per the method of Procedure B(1)(b). Oligonucleotide identity is as follows:

Oligonucleotide 31-A is a normal 3'–5' linked phosphodiester oligodeoxyribonucleotide of the sequence d(GGC TGU* CTG CG) (SEQ ID NO:37) where the * indicates the attachment site of either a 2'-aminolinker or a 2'-aminolinker plus pyrene.

Oligonucleotide 31-B is a normal 3'–5' linked phosphodiester oligoribonucleotide of the sequence d(GGC TGU* CTG CG) where the * indicates the attachment site of either a 2'-aminolinker or a 2'-aminolinker plus pyrene. Each of the ribonucleotides of the oligonucleotide, except the one bearing the * substituent, are 2'-O-methyl ribonucleotides.

Oligonucleotide 31-C is has 2'–5' linkage at the * position in addition to either a 3'-aminolinker or a 3'-aminolinker plus pyrene at this site. The remainder of the oligonucleotide is a phosphodiester oligodeoxyribonucleotide of the sequence d(GGC TGU* CTG CG). The base oligonucleotide (no 2'-aminolinker) was not included in the study.

| OLIGONUCLEOTIDE | MODIFICATION | DNA ΔTm TARGET | | RNA ΔTM TARGET | |
|---|---|---|---|---|---|
| 31-A | none | 52.2 | | 54.1 | |
| | 2'-aminolinker | 50.9 | | 55.5 | |
| | plus pyrene | 55.3 | 4.4 | 55.5 | 0 |
| 31-B | none | 51.5 | | 72.3 | |
| | 2'-aminolinker | 49.8 | | 69.3 | |
| | plus pyrene | 50.3 | 0.4 | 67.7 | -1.6 |
| 31-C | none | NA | | | |
| | 3'-aminolinker | 42.7 | | 51.7 | |
| | plus pyrene | 43.1 | -.3 | 46.3 | -5.4 |

The 2'–5' linkages demonstrated a higher melting temperature against an RNA target compared to a DNA target.

EXAMPLE 75

2'-O-(Propylphthalimide) adenosine and 3'-O-(Propylphthalimide)adenosine

To a solution of adenosine (20.0 g, 75 mmol) in dry dimethylformamide (550 ml) at 5° C. was added sodium hydride (60% oil, 4.5 g, 112 mmol). After one hour, N-(3-bromopropyl)phthalimide (23.6 g, 86 mmol) was added and the temperature was raised to 30° C. and held for 16 hours. Ice is added and the solution evaporated in vacuo to a gum. The gum was partitioned between water and ethyl acetate (4×300 ml). The organic phase was separated, dried, and evaporated in vacuo and the resultant gum chromatographed on silica gel (95/5 CH$_2$Cl$_2$/MeOH) to give a white solid (5.7 g) of the 2'-O-(propylphthalimide)adenosine. Those fractions containing the 3'-O-(propylphthalimide)adenosine were rechromatographed on silica gel using the same solvent system.

Crystallization of the 2'-O-(propylphthalimide) adenosine fractions from methanol gave a crystalline solid, m.p. 123–124° C. $^1$H NMR (400 MHz: DMSO-$d_6$) δ 1.70(m, 2H, CH$_2$), 3.4–3.7 (m, 6H, C$_{5'}$, CH$_2$, OCH$_2$, Phth CH$_2$), 3.95 (q, 1H, C$_4$,H), 4.30 (q, 1H, C$_5$,H), 4.46 (t, 1H, C$_2$,H), 5.15 (d, 1H, C$_3$,OH), 5.41 (t, 1H, C$_5$,OH), 5.95 (d, 1H, C$_1$,H) 7.35 (s, 2H, NH$_2$), 7.8 (brs, 4H, Ar), 8.08 (s, 1H, C$_2$H) and 8.37 (s, 1H, C$_8$H). Anal. Calcd. C$_{21}$H$_{22}$N$_6$O$_6$: C, 55.03; H, 4.88; N, 18.49. Found: C, 55.38; H, 4.85; N, 18.46.

Crystallization of the 3'-O-(propylphthalimide) adenosine fractions from H$_2$O afforded an analytical sample, m.p. 178–179° C. $^1$H NMR (400 MHz: DMSO-$d_6$) δ 5.86 (d, 1H, H-1').

EXAMPLE 76

2'-O-(Propylphthalimide)-N$^6$-benzoyladenosine

2'-O-(Propylphthalimide)adenosine was treated with benzoyl chloride in a manner similar to the procedure of Gaffney, et al., *Tetrahedron Lett.* 1982, 23, 2257. Chromatography on silica gel (ethyl acetate-methanol) gives the title compound. Anal. Calcd. C$_{28}$H$_{26}$N$_6$O$_7$: C, 60.21; H, 4.69; N, 15.05. Found: C, 59.94; H, 4.66; N, 14.76.

EXAMPLE 77

2'-O-(Propylphthalimide)-5'-O-dimethoxytrityl-N-benzoyladenosine

To a solution of 2'-O-(propylphthalimide)-N$^6$-benzoyladenosine (4.0 g) in pyridine (250 ml) was added 4,4'-dimethoxytrityl chloride (3.3 g). The reaction was stirred for 16 hours. The reaction was added to ice/water/ethyl acetate, the organic layer was separated, dried, and concentrated in vacuo and the resultant gum chromatographed on silica gel (ethyl acetate-methanol triethylamine) to give the title compound. Anal. Calcd. C$_{49}$H$_{44}$N$_6$O$_9$: C, 68.36; H, 5.15; N, 9.76. Found: C, 68.16; H, 5.03; N, 9.43.

EXAMPLE 78

N$_6$-Benzoyl-5'-O-dimethoxytrityl-2'-(propylphthalimide)-3'-O-(N,N-diisopropyl-β-cyanoethyl) adenosine Phosphoramidite 2'-O-(Propylphthalimide)-5'-O-dimethoxytrityl-N$^6$-benzoyladenosine was treated with (β-cyanoethoxy)chloro-N,N-diisopropyl)aminophosphane in a manner similar to the procedure of Seela, et al., *Biochemistry* 1987, 26, 2233. Chromatography on silica gel (EtOAc/hexane) gave the title compound as a white foam. $^{31}$P NMR (CD$_3$CN) 150.88, 151.22.

EXAMPLE 79

2'-O-(Propylamino)adenosine

A solution of 2'-O-(propylphthalimide)adenosine (8.8 g, 19 mmol), 95% ethanol (400 ml) and hydrazine (10 ml, 32 mmol) was stirred for 16 hrs at room temperature. The reaction mixture was filtered and filtrate concentrated in vacuo. Water (150 ml) was added and acidified with acetic acid to pH 5.0. The aqueous solution was extracted with EtOAc (2×30 ml) and the aqueous phase was concentrated in vacuo to afford 7.1 g (95%) of the titled compound as a HOAc salt. $^1$H NMR (200 MHz, DMSO-$d_6$) δ 1.70 (m, 2H, CH$_2$), 2.76 (m, 2H, CH$_2$NH$_2$), 3.55–3.67 (m, 4H, C$_5$,CH$_2$, OCH2), 3.00 (q, 1H, C$_4$,H), 4.30 (q, 1H, C$_3$,H), 4.47 (t, 1H, C$_2$,H), 6.0 (d, 1H, C$_1$,H), 7.39 (s, 2H, NH$_2$) and 8.16 (s, 1H, C$_2$H).

EXAMPLE 80

2'-O-[3-(N-trifluoroacetamido)propyl]adenosine

A solution of 2'-O-(propylamino) adenosine in methanol (50 ml) and triethylamine (15 ml, 108 mmol) was treated with ethyl trifluoroacetate (18 ml, 151 mmol). The reaction was stirred for 16 hrs and then concentrated in vacuo and the resultant gum chromatographed on silica gel (9/1, EtOAc/MeOH) to give the title 3.3 g of the compound (54%). m.p. 200–201° C. (CH$_3$CN). $^1$H NMR (200 MHz, DMSO-$d_6$) δ 1.7 (m, 2H, CH$_2$), 3.2 (m, 2H, CH$_2$NHCO), 3.37–3.67 (m, 4H, C$_5$,CH$_2$, OCH$_2$), 4.00 (q, 1H, C$_4$,H), 4.35 (q, 1H, C$_3$,H), 4.49 (t, 1H, C$_2$,H), 5.26 (d, 1H, C$_3$,OH), 5.43 (t, 1H, C$_5$,OH), 6.02 (d, 1H, C$_1$,H), 7.38 (s, 2H, NH$_2$), 8.16 (s, 1H, C$_2$H), 8.40 (s, 1H, C$_8$H), 9.34. (s, 1H, NHCO). $^{19}$F NMR (200 MHz, DMSO) δ –108.76. Anal. Calcd. for C$_{15}$H$_{19}$F$_3$N$_6$O$_5$: C, 42.86; H, 4.56; N, 19.99. Found: C, 43.10; H, 4.52; N, 20.03.

EXAMPLE 81

N$^4$-(Dibenzoyl)-2'-O-[3-(N-trifluoroacetamido)propyl]adenosine

2'-O-[3-(N-trifluoroacetamido)propyl]adenosine is treated as per Example 76 using a Jones modification wherein tetrabutylammonium fluoride is utilized in place of ammonia hydroxide in the work up. The crude product was purified using silica gel chromatography (EtOAc→EtOAc/MeOH 1/1) to give the title compound. $^1$H NMR (200 MHz, DMSO-$d_6$) δ 1.7 (m, 2H, CH$_2$), 3.2 (m, 2H, CH$_2$NHCO), 3.45–3.68 (m, 4H, C$_5$,CH$_2$, OCH$_2$), 4.03 (q, 1H, C$_4$,H), 4.37 (q, 1H, C$_3$,H), 4.53 (t, 1H, C$_2$,H), 5.18 (d, 1H, C$_3$,OH), 5.34 (d, 1H, C$_3$,OH), 6.17 (d, 1H, C$_1$,H), 7.45–7.83 (m, 1H, Ar), 8.73 (s, 1H, C$_2$H), 8.90 (s, 1H, C$_8$H), 9.37. (s, 1H, NHCO). $^{19}$F NMR (200 MHz, DMSO) δ –108.76. Anal. Calcd. for C$_{28}$H$_{27}$F$_3$N$_6$O$_7$: C, 55.41; H, 4.33; N, 13.37. Found: C, 55.16H, 4.24; N, 13.09.

EXAMPLE 82

N$^6$— (Dibenzoyl)-5'-O-(dimethoxytrityl)-2'-O-[3-(N-trifluoroacetamido)propyl]adenosine 4,4'-Dimethoxytrityl chloride (3.6 g, 10.0 mmol.) was added to a solution of N$^6$-(dibenzoyl)-2'-O-[3-(N-trifluoroacetamido)propyl)adenosine in pyridine (100 ml) at room temperature and stirred for 16 hrs. The solution was concentrated in vacuo and chromatographed on silica gel (EtOAc/TEA 99/1) to give the title compound. $^1$H NMR (200 MHz, DMSO-$d_6$) δ 1.74 (m, 2H, CH$_2$), 3.23 (m, 2H, CH$_2$NHCO), 3.60–3.73 (m, 10H, ArOCH$_3$,C$_5$,CH$_2$, OCH$_2$), 4.09 (m, 1H, C$_4$,H), 4.51 (q, 1H, C$_3$,H), 4.66 (t, 1H, C$_2$,H), 5.34 (d, 1H, C$_3$,OH), 6.17 (d, 1H, C$_1$,H), 6.80–7.83 (m, 23H, Ar), 8.64 (s, 1H, C$_2$H), 8.78 (s, 1H, C$_8$H), 9.35. (s, 1H, NHCO). $^{19}$F NMR (200 MHz, DMSO) δ –108.76. Anal. Calcd. for C$_{49}$H$_{45}$F$_3$N$_6$O$_9$: C, 68.36; H, 5.15; N, 9.76. Found: C, 68.16H, 5.03; N, 9.43.

EXAMPLE 83

N$^6$-(Dibenzoyl)-5'-O-(dimethoxytrityl)-2'-O-[3-(N-trifluoroacetamido)propyl]-3'-O-(N,N-diisopropyl-β-cyanoethyl)adenosine Phosphoramidite A solution of N$^6$—(dibenzoyl)-5'-O-(dimethoxytrityl)-2'-O-[3-(N-trifluoroacetamido)propyl]adenosine in dry CH$_2$Cl$_2$ was treated with bis-N,N-diisopropylamino cyanoethyl phosphite (1.1 eqiv) and N,N-diisopropylaminotetrazolide (catalytic amount) at room temperature for 16 hrs. The reaction was concentrated in vacuo and chromatographed on silica gel (EtOAc/hexane/TEA 6/4/1) to give 0.5 g of the title compound. $^{31}$P NMR (200 MHz, CD$_3$CN) 150.87; (200 MHz, CDCL$_3$) 150.55, 150.83. $^{19}$F NMR (200 MHz, CD$_3$CN) 107.14, (200 MHz, CDCl$_3$) 102.67.

EXAMPLE 84

2'-O-(Butylphthalimide) adenosine

The title compound is prepared as per example 75, using N-(4-bromobutyl)phthalimide in place of the 1-bromopropane. Chromatography on silica gel (EtOAC-MeOH) gives the title compound as a white solid. M.P. 199–200° C. Anal. Calcd. C$_{22}$H$_{24}$N$_6$O$_6$: C, 56.42; H, 5.16; N, 17.94. Found: C, 56.31; H, 5.04; N, 17.95.

The 3' compound can be separated from the mother liquors as per Example 75 above. $^1$H NMR (200 MHz, DMSO-d$_6$) δ 5.88 (d, 1H, C$_1$·H).

EXAMPLE 85

2'-O-(Butylphthalimide-N$^6$-benzoyladenosine)

Benzoylation of 2'-O-(butylphthalimide)adenosine as per Example 76 gave the title compound. $^1$H NMR (200 MHz, DMSO-d$_6$) δ 6.18 (d, 1H, C$_1$·H). Anal. Calcd. C$_{29}$H$_2$N$_6$O$_7$: C, 60.83; H, 4.93; N, 14.68. Found: C, 60.48; N, 14.41.

EXAMPLE 86

2'-O-(Butylphthalimide)-5'-O-dimethoxytrityl-N$^6$-benzoyladenosine

The title compound was prepared from 2'-O-(butylphthalimide)-N$^6$-benzoyladenosine as per Example 77. $^1$H NMR (200 MHz, DMSO-d$_6$) δ 6.20 (d, 1H, C$_1$·H). Anal. Calcd. for C$_{50}$H$_{46}$N$_6$O$_9$: C, 68.64; H, 5.29; N, 9.60. Found: C, 68.47; H, 5.12; N, 9.37.

EXAMPLE 87

N$^6$-Benzoyl-5'-O-(dimethoxytrityl)-2'-O-(butylphthalimide)-3'-O-(N,N-diisopropyl-β-cyanoethyl)adenosine Phosphoramidite The title compound was prepared from 2'-O-(butylphthalimide)-5'-O-dimethoxytrityl-N$^6$-benzoyladenosine as per Example 78. $^{31}$P NMR (CD$_3$CN) S 150.88, 151.22.

EXAMPLE 88

2'-O-(Pentylphthalimido)adenosine

The title compound was prepared as per Example 75, using N-(5-bromopentyl)phthalimide. The crude material from the extraction was chromatographed on silica gel using CHCl$_3$/MeOH (95/5) to give a mixture of the 2' and 3' isomers. The 2' isomer was recrystallized from EtOH/MeOH 8/2. The mother liquor was rechromatographed on silica gel to afford the 3' isomer.

2'-O-(Pentylphthalimido)adenosine: M.P. 159–160° C. Anal. Calcd. for C$_{23}$H$_{24}$N$_6$O$_5$: C, 57.26; H, 5.43; N, 17.42. Found: C, 57.03; H, 5.46; N, 17.33.

3'-O-(Pentylphthalimido) adenosine: $^1$H NMR (DMSO-d$_6$) δ 5.87 (d, 1H, H-1').

EXAMPLE 89

2'-O-(Pentylphthalimido)-N$^6$-benzoyladenosine

Benzoylation of 2'-O-(pentylphthalimido) adenosine was achieved as per the procedure of Example 76 to give the title compound. $^1$H NMR (DMSO-d$_6$): 6.10 (d, 1H, C$_1$·H). Anal. Calcd. for C$_{30}$H$_{30}$N$_6$O$_7$: C, 61.43; H, 5.16; N, 14.33. Found: C, 61.51; H, 4.97; N, 14.10.

EXAMPLE 90

2'-O-(Pentylphthalimido)-5'-O-(dimethoxytrityl)-N$^6$-benzoyladenosine

The title compound was prepared from 2'-O-(pentylphthalimide)-N$^6$-benzoyladenosine as per the procedure of Example 77. Chromatography on silica gel (ethylacetate, hexane, triethylamine), gave the title compound. Anal. Calcd. for C$_{51}$H$_{48}$N$_6$O$_9$: C, 68.91; H, 5.44; N, 9.45. Found: C, 68.65; H, 5.45; N, 9.61.

EXAMPLE 91

N$^6$-Benzoyl-5'-O-(dimethoxytrityl)-2'-O-(pentylphthalimido)-3'-(N,N-diisopropyl-β-cyanoethyl) Phosphoramidite The title compound was prepared from 2'-O-(pentylphthalimide)-5'-O-(dimethoxytrityl)-N$^6$-benzoyladenosine as per the procedure of Example 78 to give the compound as a white foam.

EXAMPLE 92

2-Amino-2'-α-(propylphthalimide)adenosine and 2-Amino-3'-O-(propylphthalimide)adenosine To a solution of 2-aminoadenosine (75 g, 281 mmol) in dry dimethylformamide (2000 ml) at room temperature was added sodium hydride 60% (13.0 g, 325 mmol). After one hour N-(3-bromopropane)phthalimide (86.6 g, 3.23 mmol) was added and the temperature was raised to 40° C. and held for 16 hrs. A further aliquot of sodium hydride 60% (6.2 g, 155 mmol) and N-(3-bromopropyl)phthalimide (40 g, 150 mmol) was added and heating was continued for an additional 16 hrs. The reaction mixture was cooled, quenched with MeOH and concentrated in vacuo. The resultant gum was chromatographed on silica gel (CHCl$_3$/MeOH 9/1) to give 53.3 g of the 2' isomer (42%). Those fractions containing the 3' isomer were crystallized from EtOAc/MeOH to yield 20 g of the 3' isomer (16%).

2-Amino-2'-O-(propylphthalimide)adenosine: $^1$H NMR (200 MHz, DMSO-d$_6$) δ 1.82 (m, 2H, CH$_2$), 3.35–3.63 (m, 4H, OCH$_2$, C$_5$·H$_2$), 3.91 (m, 1H, C$_4$·H), 4.26 (m, 1H, c$_3$·H), 4.39 (m, 1H, C$_2$·H), 5.10 (d, 1H, C$_3$·OH), 5.44 (t, 1H, C$_5$,OH), 5.77 (s, 2H, NH$_2$), 5.81 (d, 1H, C$_1$,H), 6.79 (bs, 2H, NH$_2$), 7.85 (bs, 4H, Ar) and 7.97 (s, 1H, C$_8$H). Anal. Calcd. for C$_{21}$H$_{23}$N$_7$O$_6$: C, 53.72; H, 4.94; N, 20.88. Found: C, 53.70; H, 4.48; N, 20.56.

2-Amino-3'-O-(propylphthalimide)adenosine: m.p. 222–224° C., $^1$H NMR (DMSO-d$_6$) δ 5.69 (d, 1H, H-1').

EXAMPLE 93

2'-O-(Propylphthalimide)guanosine

2-Amino-2'-O-(propylphthalimide)adenosine (38.6 g, 82 mmol) was dissolved in dimethylsulfoxide (DMSO, 1000 ml). Sodium phosphate (0.1 M, 63 ml) and Tris buffer (0.5 M, 1200 ml) were added with stirring. The solution was adjusted to pH 7.0 with phosphoric acid. Adenosine deaminase (Sigma, 1.7 g) was added and the temperature raised to 35° C. The solution was stirred for 4 days with an additional aliquot of adenosine deaminase (0.2 g) added every 24 hrs. The solution was maintained at pH 7.0 with the addition of phosphoric acid. The reaction was cooled, filtered and concentrated in vacuo. The resultant gum was crystallized from MeOH to give 31.6 of the title compound (82%6). $^1$H NMR (200 MHz, DMSO-d$_6$) δ 1.82 (m, 2H, CH$_2$), 3.45 (m, 4H, OCH$_2$, C$_5$H$_2$), 3.85 (m, 1H, C$_4$,H) 4.26 (m, 2H, C$_3$,H, C$_2$,H), 5.09 (M, 2H, C$_3$,OH, C$_5$,OH), 5.80 (d, 1H, C$_1$,H), 6.47 (s, 2H, NH$_2$), 7.84 (s, 4H, Ar), 7.97 (s, 1H, C$_8$H) AND 10.65 (s, 1H, ArNH). Anal. Calcd. for C$_{21}$H$_{21}$N$_6$O$_7$: C, 53.72; H, 4.94; N, 20.88. Found: C, 54.02; H, 4.73; N, 20.53.

EXAMPLE 94

2'-O-(Propylamino)guanosine

2'-O-(Propylphthalimide)guanosine was treated as per the procedure of Example 79 in water/methanol as the solvent to give the title compound in 91% yield. $^1$H NMR (200 MHz, DMSO-d$_6$) δ 1.80 (m, 2H, CH$_2$), 3.35–3.70 (m, 4H, OCH$_2$, C$_5$H$_2$), 3.85 (m, 1H, C$_4$,H), 4.27 (m, 2H, C$_3$,H,C$_2$,H), 5.10 (m, 2H, C$_3$,OH,C$_5$,OH), 5.78 (d, 1H, C$_1$,H), 6.49 (s, 2H, NH$_2$) and 7.97 (s, 1H, C$_8$H).

EXAMPLE 95

2'-O-[3-(N-trifluoroacetamido)propyl]guanosine

2'-O-(Propylamino)guanosine was treated as per the procedure of Example 80 to give the title compound.

EXAMPLE 96

N$^2$-(Dibenzoyl)-2'-O-[3-(N-trifluoroacetamido) propyl]guanosine

2'-O-[3-(N-trifluoroacetamido)propyl]guanosine was treated as per the procedure of Example 81 to give the title compound.

EXAMPLE 97

N$^2$-(Dibenzoyl)-5'-O-(dimethoxytrityl)-2'-O-[3-(N-trifluoroacetamido)propyl]guanosine N$^2$-(Dibenzoyl)-2'-O-[3-(N-trifluoroacetamido)propyl]-guanosine was treated as per the procedure of Example 82 to give the title compound.

EXAMPLE 98

N$^2$-(Dibenzoyl)-5'-O-(dimethoxytrityl)-2'-O-[3-(N-trifluoroacetamido)propyl]-3'-O-(N,N-diisopropyl-β-cyanoethyl)guanosine Phosphoramidite N$^2$-(Dibenzoyl)-5'-O-(dimethoxytrityl)-2'-O-[3-(N-trifluoroacetamido)propyl]guanosine was treated as per the procedure of Example 83 to give the title compound. $^{31}$P NMR (CDCl$_3$) 150.49, 150.91. $^{19}$F NMR (CDCl$_3$) 102.71, 102.75.

EXAMPLE 99

2'-O-(Propylphthalimide)uridine and 3'-O-(Propylphthalimide)uridine

A solution of uridine-tin complex (prepared as per Example 3) (48.2 g, 115 mmol) in dry DMF (150 ml) and N-(3-bromopropyl)phthalimide (46 g, 172 mmol) was heated at 130° C. for 6 hrs. The crude product was chromatographed directly on silica gel CHCl$_3$/MeOH 95/5. The isomer ration of the purified mixture was 2'/3' 81/19. The 2' isomer was recovered by crystallization from MeOH. The filtrate was rechromatographed on silica gel using CHCl$_3$→CHCl$_3$/MeOH (95/5) gave the 3' isomer as a foam.

2'-O-(Propylphthalimide)uridine: Analytical sample recrystallized from MeOH, m.p. 165.5–166.5° C., $^1$H NMR (200 MHz, DMSO-d$_6$) δ 1.87 (m, 2H, CH$_2$), 3.49–3.65 (m, 4H, C$_2$,H), 3.80– 3.90 (m, 2H, C$_3$,H$_1$C$_4$,H), 4.09(m, 1H, C$_2$,H), 5.07 (d, 1 h, C$_3$,OH), 5.16 (m, 1H, C$_5$,OH), 5.64 (d, 1H, CH=), 7.84 (d, 1H, C$_1$,H), 7.92 (bs, 4H, Ar), 7.95 (d, 1H, CH=) and 11.33 (s, 1H, ArNH). Anal. C$_{20}$H$_{21}$N$_3$H$_8$, Calcd. C, 55.69; H, 4.91; N, 9.74. Found, C, 55.75; H, 5.12; N, 10.01.

3'-O-(Propylphthalimide)uridine: $^1$H NMR (DMSO-d$_6$) δ 5.74 (d, 1H, H-1').

EXAMPLE 100

2'-O-(Propylamino)uridine

The title compound was prepared as per the procedure of Example 79 (90% yield). $^1$H NMR (200 MHz, DMSO-d$_6$) δ 1.80 (m, 2H, CH$_2$), 3.57–3.66 (m, 4H, OCH$_2$,C$_5$,H$_2$), 3.88 (m, 2H, C$_3$,H,C$_4$,H), 4.15 (m, 1H, C$_2$,H), 5.64 (d, 1H, CH=), 5.82 (d, 1H, C$_1$,H), 7.02 (bs, 2H, NH$_2$) and 8.00 (d, 1H, C$_8$H).

EXAMPLE 101

2'-O-[3-(N-trifluoroacetamido)propyl]uridine

2'-O-(Propylamino)uridine was treated as per the procedure of Example 80 to give the title compound. $^1$H NMR (200 MHz, DMSO-d$_6$) δ 1.75 (m, 2H, CH$_2$), 3.22–3.35 (m, 2H, CH$_2$NH), 3.38–3.67 (m, 4H, OCH$_2$,C$_5$,H$_2$), 5.16 (m, 2H, C$_3$,OH,C$_5$,OH), 5.67 (d, 1H, CH=), 7.95 (d, 1H, CH=), 9.34 (bs, 1H, NHCO) and 11.36 (s, 1H, ArNH). $^{19}$F NMR (200 MHz, DMSO) 108.76. Anal. Calcd. for C$_{14}$H$_{18}$F$_3$N$_3$O$_7$: C, 42.31; H, 4.56; N, 10.60. Found: 42.56; H, 4.61; N, 10.25.

EXAMPLE 102

5'-O-(dimethoxytrityl)-2'-O-[3-(N-trifluoroacetamido)propyl]-uridine

2'-O-[3-(N-trifluoroacetamido)propyl]uridine was treated as per the procedure of Example 82 to give the title compound. $^1$H NMR (200 MHz, DMSO-$d_6$) δ 1.95 (m, 2H, CH$_2$), 3.42–3.80 (m, 12H, ArOCH$_3$,OCH$_2$,C$_5$.H$_2$), 4.03 (m, 2H, C$_2$.H), 4.45 (m, 1H, C$_3$.OH), 5.30 (d, 1H, CH=), 5.91 (s, 1H, C$_1$.H), 6.83–7.43 (m, 13H, ArH), 7.90 (bs, 1H, NHCO), 8.10 (d, 1H, CH=) and 10.3 (s, 1H, ArNH). $^{19}$F NMR (200 MHz, DMSO) 102.75.

EXAMPLE 103

5'-O-(Dimethoxytrityl)-2'-O-[3-(N-trifluoroacetamido)propyl]-3'-O-(N,N-diisopropyl-β-cyanoethyl) uridine Phosphoramidite 5'-O-(Dimethoxytrityl)-2'-O-[3-(N-trifluoroacetamido)propyl]uridine was treated as per the procedure of Example 83 to give the title compound. $^{31}$P NMR (200 MHz, CD$_3$CN) 154.87, 155.62. $^{19}$F NMR (200 MHz, CD$_3$CN) 107.19.

EXAMPLE 104

2'-O-(Propylphthalimide) cytidine and 3'-O-(Propylphthalimide)-cytidine

The title compounds were prepared as per the procedure of Example 75.

2'-O-(propylphthalimide)cytidine: $^1$H NMR (200 MHz, DMSO-$d_6$) δ 5.82 (d, 1H, C$_1$.H).

3'-O-(propylphthalimide)cytidine: $^1$H NMR (200 MHz, DMSO-$d_6$) δ 5.72 (d, 1H, C$_1$.H).

EXAMPLE 105

2'-O-(Propylamino)cytidine

2'-O-(Propylphthalimide)cytidine was treated as per the procedure of Example 79 to give the title compound. $^1$H NMR (200 MHz, DMSO-$d_6$) δ 5.82 (d, 1H, C$_1$.H).

EXAMPLE 106

2'-O-[3-(N-trifluoroacetamido)propyl]cytidine

2'-O-(Propylamino)cytidine was treated as per the procedure of Example 80 to give the title compound. $^{19}$F NMR (DMSO-$d_6$) 108.73.

EXAMPLE 107

N$^4$-(Benzoyl)-2'-O-[3-(N-trifluoroacetamido)propyl] cytidine

2'-O-[3-(N-trifluoroacetamido)propyl]cytidine was treated as per the procedure of Example 81 to give the title compound. $^{19}$F NMR (DMSO-$d_6$) 108.79.

EXAMPLE 108

N$^4$-(Benzoyl)-5'-O-(dimethoxytrityl)-2'-O-[3-(N-trifluoroacetamido)propyl]cytidine N$^4$— (Benzoyl)-2'-O-[3-(N-trifluoroacetamido)propyl]cytidine was treated as per the procedure of Example 82 to give the title compound.

EXAMPLE 109

N$^4$-(Benzoyl)-5'-O-(dimethoxytrityl)-2'-O-[3-(N-trifluoroacetamido)propyl]-3'-O-(N,N-diisopropyl-β-cyanoethyl)cytidine Phosphoramidite N$^4$-(Benzoyl)-5'-O-(dimethoxytrityl)-2'-0[3-(N-trifluoroacetamido)propyl]cytidine was treated as per the procedure of Example 83 to give the title compound. $^{31}$P NMR (CDCl$_3$) 150.03, 151.36. $^{19}$F NMR (CDCl$_3$) 102.76.

EXAMPLE 110

2'-O-[3-(Imidizo-1-yl)propyl]adenosine

The title 2'-O-substituted compound was prepared as per the procedure of Example 75 using 1-(4-bromopropyl)imidazole. $^1$H NMR (200 MHz, DMSO-$d_6$) δ 6.02 (d, 1H, C$_1$.H).

The corresponding 3'-O— substituted compound can be separated from the mother liquors as per Example 75. $^1$H NMR (200 MHz, DMSO-$d_6$) δ 5.91 (d, 1H, C$_1$.H).

EXAMPLE 111

2'-O-[4-(Imidizo-1-yl)butyl)]adenosine and 3'-O-[4-(Imidizo-1-yl)butyl]adenosine A solution of adenosine (6.97 g, 26 mmol) in dry DMF (250 ml) was treated with NaH 60% (3.9 g, 97 mmol) for 15 minutes. N-(4-Bromobutyl)imidazoline acetate salt (9.4 g, 2.1 equiv. HOAc, 29 mmol) was added and the reaction mixture stirred at room temperature for 2 days. The reaction was quenched (MeOH) and concentrated in vacuo to a semi-solid. The solid was dissolved in water (250 ml) and extracted with EtOAc (2×100 ml). The aqueous phase was concentrated in vacuo and chromatographed on silica gel using EtOAc/MeOH (6/4) to give a mixture of 2' and 3' isomers (70/30, 62%). Crystallization of this solid from EtOAc/MeOH 8/2 gave the 2' isomer. Concentration of the mother liquors and subsequent crystallization from MeOH afforded the 3' isomer in 12% yield.

2'-O-[4-(Imidizo-1-yl)butyl]adenosine: $^1$H NMR (200 MHz, DMSO-$d_6$) δ 6.01 (d, 1H, C$_1$.H).

3'-O-[4-(Imidizo-1-yl)butyl]adenosine: m.p. 183–184° C. $^1$H NMR (DMSO-$d_6$) δ 5.89 (d, 1H, H-1').

EXAMPLE 112

2'-O-[4-(Imidizo-1-yl)butyl]-N$^6$-benzoyladenosine

The title compound was prepared 2'-O-[4-(imidizo-1-yl) butyl]adenosine as per Example 76.

EXAMPLE 113

2'-O-[4-(Imidizo-1-yl)butyl]-5'-O-dimethoxytrityl-$N^6$-benzoyladenosine

The title compound was prepared from $N^6$-benzoyl-2'-O-[4-(imidizo-1-yl)butyl]adenosine as per Example 77.

EXAMPLE 114

$N^6$-Benzoyl-5'-O-(dimethoxytrityl)-2'-O-[4-(imidizo-1-yl)(butyl]-3'-O-(N,N-diisopropyl-1-cyanoethyl) adenosine Phosphoramidite The title compound was prepared from 2'-O-[4-(imidizo-1-yl)butyl]-5'-O-dimethoxytrityl-$N^6$-benzoyladenosine as per Example 78. $^{31}$P NMR (CDCl$_3$) 150.48, 151.06.

EXAMPLE 115

2-Amino-2'-O-[4-(imidizo-1-yl)butyl]adenosine and 2-Amino-3'-O-[4-(imidizo-1-yl)butyl]adenosine The title compounds are prepared as per Example 111 with the substitution of 2-aminoadenosine for adenosine. The isomer ratio of 2'/3' was 74/26.

2-Amino-2'-O-[4-(imidizo-1-yl)butyl]guanosine: $^1$H NMR (200 MHz, DMSO-d$_6$) δ 5.84 (d, 1H, $C_1$.H).

2-Amino-3'-O-[4-(imidizo-1-yl)butyl]guanosine: $^1$H NMR (200 MHz, DMSO-d$_6$) δ 5.68 (d, 1H, $C_1$.H)

EXAMPLE 116

2'-O-[4-(Imidazo-1-yl)butyl]guanosine

In the manner described in Example 93, 2-amino-2'-O-[4-(imidazo-1-yl)butyl]adenosine in sodium phosphate (0.1 M) and Tris buffer (0.5 M) at pH 7.0 is deaminated with adenosine deaminase (Sigma) at 35° C. to give the title compound.

EXAMPLE 117

$N^2$-(Dibenzoyl)-2'-O-[4-(imidazo-1-yl)butyl]guanosine

2'-O-[4-(Imidazo-1-yl)butyl]guanosine was treated as per the procedure of Example 81 to give the title compound.

EXAMPLE 118

$N^2$-(Dibenzoyl)-5'-O-(dimethoxytrityl)-2'-O-[4-(imidazo-1-yl)butyl]guanosine $N^2$— (Dibenzoyl)-2'-O-[4-(imidizo-1-yl)butyl]guanosine was treated as per the procedure of Example 82 to give the title compound.

EXAMPLE 119

$N^2$-(Dibenzoyl)-5'-O-(dimethoxytrityl)-2'-O-[4-(imidazo-1-yl)butyl]-3'-O-(N,N-diisopropyl-β-cyanoethyl)guanosine Phosphoramidite $N^2$-(Dibenzoyl)-5'-O-(dimethoxytrityl)-2'-O-[4-(imidazo-1-yl)butyl]guanosine was treated as per the procedure of Example 83 to give the title compound. $^{31}$P NMR (CDCl$_3$) 150.67, 150.80.

EXAMPLE 120

2'-O-[4-(Imidizo-1-yl)butyl]cytidine and 3'-O-[4-(imidizo-1-yl)-butyl]cytidine

The title compounds were prepared as per the procedure of Example 111 with the substitution of cytidine for adenosine. The crude product was chromatographed on silica gel using EtOAc/MeOH/HOAc. The isomer ratio of 2'/3' was 60/40.

2'-O-[4-(Imidizo-1-yl)butyl]cytidine: $^1$H NMR (200 MHz, DMSO-d$_6$) δ 5.88 (d, 1H, $C_1$.H).

3'-O-[4-(Imidizo-1-yl)butyl]cytidine: $^1$H NMR (DMSO-d$_6$) δ 5.78 (d, 1H, H'1').

EXAMPLE 121

2'-O-[4-(Imidizo-1-yl)butyl]-$N^4$-benzoylcytidine

The title compound was prepared 2'-O-[4-(imidizo-1-yl)butyl]cytidine as per Example 76.

EXAMPLE 122

2'-O-[4-(Imidizo-1-yl)butyl]-5'-O-dimethoxytrityl-$N^4$-benzoylcytidine

The title compound was prepared from $N^4$-benzoyl-2'-O-[4-(imidizo-1-yl)butyl]cytidine as per Example 77.

EXAMPLE 123

$N^4$-Benzoyl-5'-O-(dimethoxytrityl)-2'-O-[4-(imidizo-1-yl)-(butyl]-3'-O-(N,N-diisopropyl-β-cyanoethyl)cytidine Phosphoramidite The title compound was prepared from 2'-O-[4-(imidizo-1-yl)butyl]-5'-O-dimethoxytrityl-$N^4$-benzoylcytidine as per Example 78. $^{31}$P NMR (CDCl$_3$) 150.39, 150.92.

EXAMPLE 124

3-Benzyloxymethyl-5-methyluridine

A solution of 5-methyluridine (51.6, 200 mmol) in DMF (100 ml) was treated with sodium hydride (60% oil, 9.9 g, 24.8 mmol). After 1 hr at room temperature, benzylchloromethyl ether (34.4 g, 220 mmol) was added dropwise and the reaction mixture heated to 35° C. for 4 hrs. The reaction mixture was cooled, quenched with MeOH (5 ml), filtered and concentrated in vacuo. The resultant gum was partitioned between EtOAc/sat. NaCl, separated, dried and the organic phase concentrated whereupon the title compound crystallized. $^1$H NMR (DMSO-d$_6$) δ 5.83 (d, 1H, $C_1$.—H).

EXAMPLE 125

3-Benzyloxymethyl-5-methyl-2'-O-(4-chlorobutyl) uridine

A solution of 3-benzyloxymethyl-5-methyluridine (25.9 g, 68 mmol) was treated with NaH (60% oil, 7.9 g, 200 mmol) for 1 hr at room temp. 1-Bromo-4-chlorobutane (19.7 g, 115 mmol) was added slowly and the reaction stirred at room temp. for 16 hrs. The reaction was then quenched (MeOH), concentrated in vacuo and the residue chromatographed on silica gel CHCl$_3$/MeOH 95/5 to give the title compound in 41% yield. $^1$H NMR (DMSO-d$_6$) δ 5.87 (d, 1H, C$_1$,H).

EXAMPLE 126

3-Benzyloxymethyl-5-methyl-2'-O-[4-(imidazo-1-yl) butyl]uridine

To a solution of imidazole (6.8 g, 100 mmol) in DMF (150 ml) was added NaH (60% in oil, 4 g, 100 mmol). After 4 hrs, this suspension was added to a suspension of 3-benzyloxymethyl-5-methyl-2'-O-(4-chlorobutyl)uridine (8.7 g, 18 mmol), NaI (2.6 g) and DMF (200 ml). The reaction was stirred 16 hrs at room temp., quenched with MeOH, concentrated in vacuo and the residue chromatographed on silica gel CHCl$_3$/MeOH 85/15→50/50 to give the title compound in 31% yield. $^1$H NMR (DMSO-d$_6$) δ 5.87 (d, 1H, C$_1$,H).

EXAMPLE 127

2'-O-[4-(Imidazo-1-yl)butyl]-5-methyluridine

A solution of 3-benzyloxymethyl-5-methyl-2'-O-[4-(imidazo-1-yl)butyl]uridine (5.4 g, 10 mmol) in MeOH (200 ml) was hydrogenated with 20% palladium hydroxide (9.0 g) at 1 atmosphere H$_2$ for 16 hrs. The reaction was filtered through celite and the mother liquor concentrated to afford the product in 83% yield. $^1$H NMR (DMSO-d$_6$) δ 5.86 (d, 1H, C$_1$,H).

EXAMPLE 128

5'-O-(Dimethoxytrityl)-2'-O-[4-(imidazo-1-yl)butyl]-5-methyluridine

5-Methyl-2'-O-[4-(imidazo-1-yl)butyl]uridine was treated as per the procedure of Example 77 to give the title compound in 91% yield. $^1$H NMR (DMSO-d$_6$) δ 5.86 (d, 1H, C$_1$,H).

EXAMPLE 129

5'-O-(Dimethoxytrityl)-2'-O-[4-(imidazo-1-yl)butyl]-3'-O-(N,N-diisopropyl-β-cyanoethyl)-5-methyluridine Phosphoramidite 5'-O-(Dimethoxytrityl)-5-methyl-2'-O-[4-(imidazo-1-yl) butyl]uridine was treated as per the procedure of Example 78 to give the title compound in 83% yield. $^1$H NMR (DMSO-d$_6$) δ 5.85 (d, 1H, C$_1$,H). $^{31}$P NMR (DMSO-d$_6$) 153.99, 154.45.

EXAMPLE 130

Effect Of Derivatization On Melting Temperature

Melting temperatures (Tm) for a variety of modified oligonucleotides according to the invention were determined according the method set forth in Procedure B(1) (b). The resulting data is shown in Tables 5–8, wherein all listed oligonucleotides contain 2'-deoxy sugars and phosphodiester backbones unless otherwise indicated.

Table 5 shows changes in T$_m$ that result by modifying the 2'-position of adenosine nucleotides to include a variety of substituent groups. For example, the first entry shows that the introduction of 2'-O-aminopropyl adenosine substituents at two adenosine nucleotides resulted in a heteroduplex having a T$_m$ that is 1.13° C. greater than the heteroduplex formed by an unmodified oligonucleotide having the same sequence.

Table 6 shows changes in T$_m$ that result by modifying one or more 2'- and 3'-positions of the indicated parent oligonucleotides to include linkers and pyrene conjugates. These modifications were made to terminal and internal (i.e., non-terminal) positions within the oligonucleotide. The notation "PS" indicates the presence of a phosphorothioate backbone, and the notation "2'–5' linkage" indicates 2'–5' intersugar linkages. As can be seen from the first entry, the introduction of a 2'-aminopentoxy linker to a single, internal adenosine nucleotide of the parent oligonucleotide resulted in a Tm decrease of 3.1° C. whereas the introduction of a 2'-pyrenyl-aminopentoxy conjugate resulted in a Tm increase of 3.3° C.

Tables 7a–c show changes in Tm that result by modifying one or more positions of the indicated parent oligonucleotides to include linkers and cholate or cholesterol conjugates. As can be seen from the first entry, the introduction of an aminolink linker at the 3'-position of a single terminal nucleotide of the parent phosphorothioate oligonucleotide resulted in a Tm increase of 1.3° C. and the addition of a cholate group to the linker resulted in a further Tm increase of 1.1° C.

Table 8 shows changes in T$_m$ that result by modifying one or more 3'-positions of the indicated parent oligonucleotides to include linkers and PEG conjugates. The entries under the heading "PEG vs Unmodified" represent preliminary findings. As can be seen, the first entry indicates that introduction of an aminolink linker at the 3'-position of a single terminal nucleotide of the parent phosphodiester oligonucleotide resulted in a Tm increase of 0.9° C. and that the addition of a PEG 550 group to the linker did not change the Tm of the resulting product.

TABLE 5

THE INFLUENCE OF THE 2'-O-dA MODIFICATIONS ON THE HETERODUPLEX STABILITY

| | Tm/Modification | | | | | |
|---|---|---|---|---|---|---|
| TARGETS | 2'O-propyl-dA | 2'O-aminopropyl-dA | 2'O-butyl-dA | 2'O-pentyl-dA | 2'O-aminopentyl-dA | 2'O-butyl-imidazole-dA |
| GAGCTCCCAGGC (SEQ ID NO:38) (2 mod.) | | +1.13 | −0.55 | −0.95 | +0.60 | −0.1 |
| CGACTATGCAAGTAC (SEQ ID NO:39) (1 mod.) | −1.08 | −1.01 | −1.50 | 00.36 | | +0.14 |
| CGACTATGCAAAAAC (SEQ ID NO:40) (3 mod.) | +0.98 | +0.51 | +0.07 | +0.85 | | — |

TABLE 5-continued

THE INFLUENCE OF THE 2'-O-dA MODIFICATIONS ON THE HETERODUPLEX STABILITY

| TARGETS | Tm/Modification | | | | | |
|---|---|---|---|---|---|---|
| | 2'O-propyl-dA | 2'O-amino propyl-dA | 2'O-butyl-dA | 2'O-pentyl-dA | 2'O-amino pentyl-dA | 2'O-butyl-imidazole-dA |
| ACCGAGGATCATGTCGTACGC (SEQ ID NO:41) (5 mod.) | −0.36 | −0.40 | −0.56 | −0.92 | −1.11 | −0.45 |
| Average | −0.2 + −0.7 | −0.15 + −1.15 | −0.4 + −1.0 | −0.9 + −0.6 | −0.35 + −1.1 | −0.31 + −0.6 |

TABLE 6

EFFECT OF PYRENE AND LINKERS ON $T_M$ VS DNA

| Pyrene Conjugate | Linker Only | Unmodified Parent | # Mods | Pos. of Mods. | Pyrene vs Linker Only | | Linker Only vs Unmodified | | Pyrene vs Unmodified | |
|---|---|---|---|---|---|---|---|---|---|---|
| | | | | | dTm | dTm/Mod. | dTm | dTm/Mod. | dTm | dTm/Mod. |
| 2'-pyrenyl-amino-pentoxy-dA | 2'-amino-pentoxy dA | wild type DNA | 1 | internal | +6.5 | +6.5 | −3.1 | −3.1 | +3.3 | +3.3 |
| 2'-pyrenyl-amino-hexoxy-dU | 2'-amino-hexoxy dU | wild type DNA | 1 | internal | +4.4 | +4.4 | −1.2 | −1.2 | +3.1 | +3.1 |
| 2'-pyrenyl-amino-hexoxy dU in 2'-O-methyl backgggrounde | 2'-amino-hexoxy dU in 2'-O-methyl background | fully 2'-O-methyl with U | 1 | internal | +0.5 | +0.5 | −1.7 | −1.7 | −1.2 | −1.2 |
| 2'-pyrenyl-amino-pentoxy-dA | 2'-amino-pentoxy dA | wild type DNA | 1 | internal | +4.5 | +4.5 | −2.4 | −2.4 | +2.0 | +2.0 |
| 2'-pyrenyl-amino-pentoxy-dA | 2'-amino-pentoxy dA | wild type DNA | 2 | internal | +8.3 | +4.2 | −3.7 | −1.8 | +4.6 | +2.3 |
| 3'-pyrenyl-amino-hexoxy-dU | 3'-amino-hexoxy dU | wild type DNA | 1 | 3'-term. | +2.8 | +2.8 | −0.7 | −0.7 | +2.2 | +2.2 |
| 3'-amino-linked pyrene (PS) | 3'-aminolink (PS) | fully PS DNA | 1 | 3'-term. | +0.7 | +0.7 | +0.6 | +0.6 | +1.2 | +1.2 |
| 3'-pyrenyl-amino-hexoxy-dU (2'-5' linkage) | 3'-amino-hexoxy-dU (2'-5' linkage) | DNA with dU replacing 3'-amino-hexoxy-dU | 1 | internal | +0.4 | +0.4 | −8.9 | −8.9 | −8.5 | −8.5 |

TABLE 7a

EFFECT OF CHOLATE OR CHOLESTEROL AND LINKERS ON $T_M$ VS RNA

| Cholate Conjugate | Linker Only | Unmodified Parent | # Mods | Pos. of Mods. | Cholate/cholesterol vs Linker Only | | Linker Only vs Unmodified | | Cholate/cholesterol vs Unmodified | |
|---|---|---|---|---|---|---|---|---|---|---|
| | | | | | dTm | dTm/Mod. | dTm | dTm/Mod. | dTm | dTm/Mod. |
| 3'amino-linked cholate (PS) | 3'-aminolink (PS) | fully PS DNA | 1 | 3'-term. | +1.1 | +1.1 | +1.3 | +1.3 | +2.5 | +2.5 |
| 3'-amino-linked cholesterol (PS) | 3'-aminolink (PS) | fully PS DNA | 1 | 3'-term. | ? | | +1.3 | +1.3 | ? | |
| 3'-amino-linked cholate | 3'-amino-link | wild type DNA | 1 | 3'-term. | +2.0 | +2.0 | −0.3 | −0.3 | +1.7 | +1.7 |
| 5'-amino-linked cholate | 5'-aminolink | wild type DNA | 1 | 5'-term. | +0.4 | +0.4 | +0.2 | +0.2 | +0.6 | +0.6 |
| 5'-amino-linked cholate | 5'-aminolink | wild type DNA | 1 | 5' term. | — | — | — | — | +0.1 | +0.1 |
| 5'-amino-linked cholate (PS) | 5'-aminolink (PS) | fully PS DNA | 1 | 5'-term. | — | — | — | — | +0.9 | +0.9 |
| 2'cholesterol-amino-hexoxy dU[1] | — | DNA with dU in position 1 | 1 | 5-term. | — | — | — | — | −1.3 | |
| 2'cholesterol-amino-hexoxy dU[1] | — | DNA with dU in position 10 | 1 | internal | — | — | — | — | −4.5 | |
| 2'cholesterol-amino-hexoxy dU (PS)[1] | — | fully PS DNA with dU in position 1 | 1 | 5'-term. | — | — | — | — | −3.7 | |
| 2'-adamantane-amino-hexoxy dU (PS)[1] | — | fully PS DNA with dU in position 1 | 1 | 5'-term. | — | — | — | — | 0.2 | |

TABLE 7b

EFFECT OF CHOLATE OR CHOLESTEROL AND LINKERS ON $T_M$ VS RNA

| Cholate Conjugate | Linker Only | Unmodified Parent | # Mods | Pos. of Mods. | Cholate/cholesterol vs Linker Only dTm | Cholate/cholesterol vs Linker Only dTm/Mod. | Linker Only vs Unmodified dTm | Linker Only vs Unmodified dTm/Mod. | Cholate/cholesterol vs Unmodified dTm | Cholate/cholesterol vs Unmodified dTm/Mod. |
|---|---|---|---|---|---|---|---|---|---|---|
| 2'-eiconsenic-amino-hexoxy dU (PS)[1] | — | fully PS DNA with dU in position 1 | 1 | 5'-term. | — | — | — | — | −1.3 | |
| 3'-cholesterol-amino-hexoxy dU (PS)[1] | — | fully PS DNA with dU in position 20 | 1 | 3'-term. | — | — | — | — | −0.5 | |
| 2'cholesterol-amino-hexoxy dU in position 1 3'-cholesterol-amino-hexoxy dU position 20 (PS)[1] | — | fully PS DNA with dU in positions 1 and 20 | 2 | both ends | — | — | — | — | −5.7 | |
| 2'-cholesterol-amino-hexoxy dU in position 1 3'-PEG-amino-hexoxy dU position 20 (PS)[1] | — | fully PS DNA with dU in positions 1 and 20 | 2 | both ends | — | — | — | — | −5.2 | −2.6 |
| 3'-cholesterol-amino-hexoxy dU[1] | — | DNA with dU in position 20 | 1 | 3'-term. | — | — | — | — | +0.6 | |
| 2'-cholesterol-amino-hexoxy dU in position 1 3'-cholesterol-amino-hexoxy dU position 20[1] | — | DNA with dU in positions 1 and 20 | 2 | both ends | — | — | — | — | −3.9 | |

[1]Synthesis via cholesterol amidite.

TABLE 7c

EFFECT OF CHOLATE OR CHOLESTEROL AND LINKERS ON $T_M$ VS DNA

| Cholate Conjugate | Linker Only | Unmodified Parent | # Mods | Pos. of Mods. | Cholate/cholesterol vs Linker Only dTm | Cholate/cholesterol vs Linker Only dTm/Mod. | Linker Only vs Unmodified dTm | Linker Only vs Unmodified dTm/Mod. | Cholate/cholesterol vs Unmodified dTm | Cholate/cholesterol vs Unmodified dTm/Mod. |
|---|---|---|---|---|---|---|---|---|---|---|
| 2'-cholate-amino-pentoxy dA | 2'-amino-pentoxy dA | wild type DNA | 1 | internal | −2.6 | −2.6 | −2.4 | −2.4 | −5.1 | −5.1 |
| 2'-cholate-amino-pentoxy dA | 2'-amino-pentoxy dA | wild type DNA | 2 | internal | −2.5 | −1.2 | −3.7 | −1.8 | −6.2 | −3.1 |
| 3'-amino-linked cholate (PS) | 3'-aminolink (PS) | fully PS DNA | 1 | 3'-term. | +0.4 | +0.4 | +0.6 | +0.6 | +1.0 | +1.0 |
| 3'-amino-linked cholesterol (PS) | 3'-aminolink (PS) | fully PS DNA | 1 | 3'-term. | | | +0.6 | +0.6 | | |
| 3'-amino-linked cholate | 3'-amino-link | wild type DNA | 1 | 3'-term. | +1.4 | +1.4 | −0.5 | −0.5 | +0.9 | +0.9 |
| 5'-amino-linked cholate | 5'-aminolink | wild type DNA | 1 | 5'-term. | +0.9 | +0.9 | +0.1 | +0.1 | +0.9 | +0.9 |
| 5'-amino-linked cholate | 5'-aminolink | wild type DNA | 1 | 5'-term. | — | — | — | — | +0.9 | +0.9 |
| 5'-amino-linked cholate (PS) | 5'-aminolink (PS) | fully PS DNA | 1 | 5'-term. | — | — | — | — | +1.0 | +1.1 |

TABLE 8

EFFECT OF PEG AND LINKERS ON $T_M$ VS RNA

| PEG Conjugate | Linker only | Unmodified Parent | # Mods | Pos. of Mods. | PEG vs Linker only dTm | PEG vs Linker only dTm/Mod. | Linker only vs Unmodified dTm | Linker only vs Unmodified dTm/Mod. | PEG vs Unmodified dTm | PEG vs Unmodified dTm/Mod. |
|---|---|---|---|---|---|---|---|---|---|---|
| 3'-aminolinked PEG 550 | 3'-aminolink | wild type DNA | 1 | 3'-term. | +0.0 | +0.0 | +0.9 | +0.9 | +0.9 | +0.9 |
| 3'-aminolinked PEG 2000 | 3'-aminolink | wild type DNA | 1 | 3'-term. | −0.4 | −0.4 | +0.9 | +0.9 | +0.5 | +0.5 |

TABLE 8-continued

EFFECT OF PEG AND LINKERS ON $T_M$ VS RNA

| PEG Conjugate | Linker only | Unmodified Parent | # Mods | Pos. of Mods. | PEG vs Linker only | | Linker only vs Unmodified | | PEG vs Unmodified | |
|---|---|---|---|---|---|---|---|---|---|---|
| | | | | | dTm | dTm/Mod. | dTm | dTm/Mod. | dTm | dTm/Mod. |
| 3'-aminolinked PEG 5000 | 3'-aminolink | wild type DNA | 1 | 3'-term. | −0.3 | −0.3 | +0.9 | +0.9 | +0.6 | +0.6 |
| 3'-aminolinked PEG 550 (PS) | 3'-aminolink (PS) | fully PS DNA | 1 | 3'-term. | +0.2 | +0.2 | +1.4 +0.3 | +1.4 +0.3 | +1.0 | +1.0 |
| 3'aminolinked PEG 2000 (PS) | 3'-aminolink (PS) | fully PS DNA | 1 | 3'-term. | +0.6 | +0.6 | +1.4 +0.3 | +1.4 +1.4 | +1.4 | +1.4 |
| 3'-aminolinked PEG 5000 (PS) | 3'-aminolink (PS) | fully PS DNA | 1 | 3'-term. | −0.0 | −0.0 | +1.4 +0.3 | +1.4 +0.3 | +0.8 | +0.8 |
| 2'-cholesterol-amino-hexoxy dU in position 1 3'-PEG-amino-hexoxy dU position 20 (PS)[1] | — | fully PS DNA with dU in positions 1 and 20 | 2 | both ends | — | — | — | — | −5.2 | −2.6 |

[1]Synthesis via cholesterol amidite.

What is claimed is:

1. A method for detecting the presence or absence of an RNA in a biological sample suspected of containing said RNA comprising selecting a compound capable of hybridizing with said RNA, contacting said sample with said compound, and identifying any hybrid of said compound and an RNA wherein said compound comprises a plurality of linked nucleosides, wherein:

each nucleoside includes a ribofuranosyl sugar portion and a base portion; and at least one of said nucleosides bears at a 2'-O-position, a 3'-O-position, or a 5'-O-position a substituent having formula:

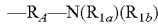

where:

each $R_A$, independently, is a straight chain or branched hydrocarbon alkylene group including from 1 to about 10 carbon atoms or $(CH_2-CH_2-Q)_x$;

$R_{1a}$ and $R_{1b}$, independently, are H, $R_2$, or have formula $C(X)-R_2$, $C(X)-R_A-R_2$, $C(X)-Q-R_A-R_2$, or $C(X)-Q-R_2$, provided $R_{1a}$ and $R_{1b}$ are not both H;

$R_2$ is a folate, a steroid molecule, a reporter molecule, a lipophilic molecule, a reporter enzyme, a peptide, a protein, or has formula $-Q-(CH_2CH_2-Q-)_x-R_3$;

X is O or S;

each Q is, independently, is NH, O, or S;

x is 1 to about 200;

$R_3$ is H, $R_A$, C(O)OH, C(O)OR$_A$, C(O)R$_A$, $R_A-N3$, or $R_A-NH_2$;

$R_4$ is Cl, Br, I, SO$_2$R$_5$ or has structure:

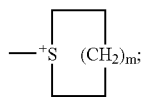

m is 2 to 7; and $R_5$ is alkyl having 1 to about 10 carbon atoms.

2. A method for detecting the presence or absence of an RNA in a biological sample suspected of containing said RNA comprising selecting an oligonucleoside capable of hybridizing with said RNA, contacting said sample with said oligonucleoside, and identifying any hybrid of said oligonucleoside and an RNA wherein said oligonucleoside comprises a ribofuranosyl sugar portion and a base portion, wherein said oligonucleoside bears at a 3'-O-position or a 5'-O-position a substituent having formula:

where:

each $R_A$, independently, is a straight chain or branched hydrocarbon alkylene group including from 1 to about 10 carbon atoms;

$R_{1a}$ and $R_{1b}$, independently, are H, $R_2$, or have formula $C(X)-R_2$, $C(X)-R_A-R_2$, $C(X)-Q-R_A-R_2$, or $C(X)-Q-R_2$, provided $R_{1a}$ and $R_{1b}$ are not both H;

$R_2$ is a folate, a steroid molecule, a reporter molecule, a lipophilic molecule, a reporter enzyme, a peptide, a protein, or has formula $-Q-(CH_2CH_2-Q-)_x-R_3$;

X is O or S;

each Q is, independently, is NH, O, or S;

x is 1 to about 200;

$R_3$ is H, $R_A$, C(O)OH, C(O)OR$_A$, C(O)R$_A$, $R_A-N3$, or $R_A-NH_2$; $R_4$ is Cl, Br, I, SO$_2$R$_5$ or has structure:

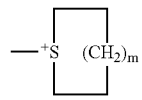

m is 2 to 7; and $R_5$ is alkyl having 1 to about 10 carbon atoms.

3. The method of claim 1 wherein more than one of said nucleosides bear said substituent at a 2'-O-position, a 3'-O-position, or a 5'-O-position.

4. The method of claim 1 wherein $R_A$ is $(CH_2)_n$ where n is an integer from 1 to about 10.

5. The method of claim 1 wherein $R_{1a}$ is H and $R_{1b}$ is $C(O)-(CH_2)_n-R_2$ where n is an integer from 1 to about 10.

6. The method of claim 1 wherein $R_{1a}$ is H and $R_{1b}$ is $R_2$.

7. The method of claim 1 wherein $R_{1a}$ is H and $R_{1b}$ is $C(O)-O-R_2$.

8. The method of claim 1 wherein $R_{1a}$ and $R_{1b}$ both are a straight chain or branched hydrocarbon alkylene group including from 1 to about 10 carbon atoms.

9. The method of claim 1 wherein $R_{1a}$ is H and $R_{1b}$ is $C(O)-(CH_2)_n-R_2$ where n is an integer from 1 to about 10.

10. The method of claim 1 wherein $R_{1a}$ is H and $R_A$ is $(CH_2)_5$.

11. The method of claim 1 wherein $R_{1a}$ is H and $R_{1b}$ is $C(S)-NH-R_2$.

12. The method of claim 1 wherein $R_2$ includes pyrene, fluorescein, dinitrophenyl, cholesterol, or acridine.

13. The method of claim 1 wherein $R_{1a}$ is H and $R_{1b}$ is $C(O)-R_2$.

14. The method of claim 1 wherein $R_2$ has formula $-O-(CH_2CH_2-O-)_x-R_3$.

15. The method of claim 1 wherein a 3'-position of at least one of said nucleosides is linked to a 5'-position of an adjacent nucleoside.

16. The method of claim 1 wherein a 2'-position of at least one of said nucleosides is linked to a 5'-position of an adjacent nucleoside.

17. The method of claim 2 wherein $R_A$ is $(CH_2)_n$ where n is an integer from 1 to about 10.

18. The method of claim 2 wherein $R_{1a}$ is H and $R_{1b}$ is $C(O)-(CH_2)_n-R_2$ where n is an integer from 1 to about 10.

19. The method of claim 2 wherein $R_{1a}$ is H and $R_{1b}$ is $R_2$.

20. The method of claim 2 wherein $R_{1a}$ is H and $R_{1b}$ is $C(O)-O-R_2$.

21. The method of claim 2 wherein $R_{1a}$ and $R_{1b}$ both are a straight chain or branched hydrocarbon alkylene group including from 1 to about 10 carbon atoms.

22. The method of claim 2 wherein $R_{1a}$ is H and $R_{1b}$ is $C(O)-(CH_2)_n-R_2$ where n is an integer from 1 to about 10.

23. The method of claim 22 wherein $R_A$ is $(CH_2)_5$.

24. The method of claim 2 wherein $R_{1a}$ is H and $R_{1b}$ is $C(S)-NH-R_2$.

25. The method of claim 2 wherein $R_2$ includes pyrene, fluorescein, dinitrophenyl, cholesterol, or acridine.

26. The method of claim 2 wherein $R_{1a}$ is H and $R_{1b}$ is $C(O)-R_2$.

27. The method of claim 26 wherein $R_2$ has formula $-O-(CH_2CH_2-O-)_n-R_3$.

* * * * *

UNITED STATES PATENT AND TRADEMARK OFFICE
CERTIFICATE OF CORRECTION

PATENT NO. : 7,037,646 B1  Page 1 of 2
APPLICATION NO. : 08/602862
DATED : May 2, 2006
INVENTOR(S) : Phillip Dan Cook et al.

It is certified that error appears in the above-identified patent and that said Letters Patent is hereby corrected as shown below:

Title page:
Item [63], Related U.S. Application Data, please delete

"Continuation-in-part of application No. 08/117,363, filed on Sep. 3, 1994, now Pat. No. 6,783,931, and a continuation-in-part of application No. PCT/US91/00243, filed on Jan. 11, 1991, said application No. 08/117,363 is a continuation-in-part of No. PCT/US92/09196, filed on Oct. 23, 1992, which is a continuation-in-part of application No. 07/782,374, filed on Oct. 24, 1991, said application No. 07/782,374 is a continuation-in-part of application No. 07/463,358, filed on Jan. 11, 1990, and a continuation-in-part of application No. 07/566,977, filed on Aug. 13, 1990"

and insert therefore

--Continuation-in-part of application No. 08/117,363, filed on Sept. 3, 1993, now Pat. No. 6,783,931, and a continuation-in-part of application No. 07/782,374, filed on Oct. 24, 1991, said application No. 07/782,374 is a continuation-in-part of application No. 07/463,358, filed on Jan. 11, 1990, and a continuation-in-part of application No. 07/566,977, filed on Aug. 13, 1990, said application No. PCT/US91/00243 is a continuation-in-part of application No. 07/463,358, filed on Jan. 11, 1990, and a continuation-in-part of application No. 07/566,977, filed on Aug. 13, 1990--;

Column 119, Claim 1, line 29, please delete "$R_A$-N3" and insert therefore --$R_A$-$N_3$--;

Column 119, Claim 2, line 65, please delete "$R_A$-N3," and insert therefore --$R_A$-$N_3$--;

UNITED STATES PATENT AND TRADEMARK OFFICE
CERTIFICATE OF CORRECTION

PATENT NO. : 7,037,646 B1
APPLICATION NO. : 08/602862
DATED : May 2, 2006
INVENTOR(S) : Phillip Dan Cook et al.

It is certified that error appears in the above-identified patent and that said Letters Patent is hereby corrected as shown below:

Column 120, Claim 27, line 63, please delete "-O-$(CH_2CH_2$-O-$)_n$-$R_3$" and insert therefore -- -O-$(CH_2CH_2$-O-$)_x$-$R_3$ --.

Signed and Sealed this

Twenty-second Day of August, 2006

JON W. DUDAS
*Director of the United States Patent and Trademark Office*

```
                         SEQUENCE LISTING

<160> NUMBER OF SEQ ID NOS: 107

<210> SEQ ID NO 1
<211> LENGTH: 11
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: functionalized to incorporate a pentyl-N-
      phthalimido functionality

<400> SEQUENCE: 1
ggctgactgc g                                                         11

<210> SEQ ID NO 2
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a pentyl-N-
      phthalimido functionality

<400> SEQUENCE: 2
ctgtctccat cctcttcact                                                20

<210> SEQ ID NO 3
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(19)
<223> OTHER INFORMATION: phosphorothioate inter-nucleotide backbone
      linkage
<220> FEATURE:
```

```
<221> NAME/KEY: misc_feature
<222> LOCATION: (9)..(9)
<223> OTHER INFORMATION: functionalized to incorporate a pentyl-N-
      phthalimido functionality

<400> SEQUENCE: 3
ttgcttccat cttcctcgtc                                                  20

<210> SEQ ID NO 4
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(17)
<223> OTHER INFORMATION: phosphorothioate inter-nucleotide backbone
      linkage
<220> FEATURE:
<221> NAME/KEY: misc_feature
<222> LOCATION: (15)..(15)
<223> OTHER INFORMATION: functionalized to incorporate a pentyl-N-
      phthalimido functionality

<400> SEQUENCE: 4
tgggagccat agcgaggc                                                    18

<210> SEQ ID NO 5
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a biotin
      functionality linked via a 2'-O-pentyl-amino linking group to the
      2' position

<400> SEQUENCE: 5
ctgtctccat cctcttcact                                                  20

<210> SEQ ID NO 6
<211> LENGTH: 16
<212> TYPE: DNA
<213> ORGANISM: Artificial
<220> FEATURE:
<223> OTHER INFORMATION: Oligonucleotide

<400> SEQUENCE: 6
tccaggtgtc cgcatc                                                      16

<210> SEQ ID NO 7
<211> LENGTH: 17
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: functionalized to incorporate a pentylamino
      functionaly at its 2'-position
<220> FEATURE:
<221> NAME/KEY: misc_feature
<222> LOCATION: (8)..(9)
<223> OTHER INFORMATION: functionalized to incorporate a pentylamino
      functionaly at its 2'-position
<220> FEATURE:
```

```
<221> NAME/KEY: misc_feature
<222> LOCATION: (13)..(13)
<223> OTHER INFORMATION: functionalized to incorporate a pentylamino
      functionaly at its 2'-position
<220> FEATURE:
<221> NAME/KEY: misc_feature
<222> LOCATION: (16)..(16)
<223> OTHER INFORMATION: functionalized to incorporate a pentylamino
      functionaly at its 2'-position

<400> SEQUENCE: 7
ggaccggaag gtacgag                                                   17

<210> SEQ ID NO 8
<211> LENGTH: 17
<212> TYPE: DNA
<213> ORGANISM: Artificial
<220> FEATURE:
<223> OTHER INFORMATION: Oligonucleotide

<400> SEQUENCE: 8
cctggccttc catgctc                                                   17

<210> SEQ ID NO 9
<211> LENGTH: 17
<212> TYPE: RNA
<213> ORGANISM: Artificial
<220> FEATURE:
<223> OTHER INFORMATION: Oligonucleotide

<400> SEQUENCE: 9
ccuggccuuc caugcuc                                                   17

<210> SEQ ID NO 10
<211> LENGTH: 12
<212> TYPE: RNA
<213> ORGANISM: Artificial
<220> FEATURE:
<223> OTHER INFORMATION: Oligonucleotide

<400> SEQUENCE: 10
cccaggcuca ga                                                        12

<210> SEQ ID NO 11
<211> LENGTH: 12
<212> TYPE: RNA
<213> ORGANISM: Artificial
<220> FEATURE:
<223> OTHER INFORMATION: Oligonucleotide

<400> SEQUENCE: 11
gagcucccag gc                                                        12

<210> SEQ ID NO 12
<211> LENGTH: 12
<212> TYPE: RNA
<213> ORGANISM: Artificial
<220> FEATURE:
<223> OTHER INFORMATION: Oligonucleotide

<400> SEQUENCE: 12
caugcugcag cc                                                        12

<210> SEQ ID NO 13
<211> LENGTH: 20
<212> TYPE: DNA
<213> ORGANISM: Artificial
```

```
<220> FEATURE:
<223> OTHER INFORMATION: Oligonucleotide
<220> FEATURE:
<221> NAME/KEY: misc_feature
<222> LOCATION: (20)..(20)
<223> OTHER INFORMATION: derivatized nucleotide in an ABI 380B DNA
      synthesizer using phosphoramidite chemistry standard conditions

<400> SEQUENCE: 13
gcctttcgcg acccaacacu                                                    20

<210> SEQ ID NO 14
<211> LENGTH: 11
<212> TYPE: DNA
<213> ORGANISM: Artificial
<220> FEATURE:
<223> OTHER INFORMATION: Oligonucleotide

<400> SEQUENCE: 14
gcgtguctgc g                                                             11

<210> SEQ ID NO 15
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-hexylamino (dinitrophenyl) uridine
      phosphoramidite
<220> FEATURE:
<221> NAME/KEY: misc_feature
<222> LOCATION: (1)..(18)
<223> OTHER INFORMATION: P=S
<220> FEATURE:
<221> NAME/KEY: misc_feature
<222> LOCATION: (18)..(18)
<223> OTHER INFORMATION: non-nucleoside 6-carbon amino linker

<400> SEQUENCE: 15
ugggagccat agcgaggc                                                      18

<210> SEQ ID NO 16
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: P=O
<220> FEATURE:
<221> NAME/KEY: misc_feature
<222> LOCATION: (10)..(10)
<223> OTHER INFORMATION: 2'-O-hexylamino (dinitrophenyl) uridine
      phosphoramidite

<400> SEQUENCE: 16
tgggagccau agcgaggc                                                      18

<210> SEQ ID NO 17
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (1)..(1)
<223> OTHER INFORMATION: 2'-O-hexylamino (dinitrophenyl) uridine
      phosphoramidite
<220> FEATURE:
<221> NAME/KEY: misc_feature
<222> LOCATION: (1)..(20)
<223> OTHER INFORMATION: P=O
<220> FEATURE:
<221> NAME/KEY: misc_feature
<222> LOCATION: (20)..(20)
<223> OTHER INFORMATION: non-nucleoside 6-carbon amino linker

<400> SEQUENCE: 17
uctgagtagc agaggagctc                                                20

<210> SEQ ID NO 18
<211> LENGTH: 21
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(21)
<223> OTHER INFORMATION: P=S
<220> FEATURE:
<221> NAME/KEY: misc_feature
<222> LOCATION: (1)..(1)
<223> OTHER INFORMATION: 2'-O-[hexylamino-(cholesterol)] uridine
      phosphoramidite

<400> SEQUENCE: 18
ugcccaagct ggcatccgtc a                                              21

<210> SEQ ID NO 19
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(22)
<223> OTHER INFORMATION: P=S
<220> FEATURE:
<221> NAME/KEY: misc_feature
<222> LOCATION: (1)..(1)
<223> OTHER INFORMATION: 2'-O-[hexylamino-(cholesterol)] uridine
      phosphoramidite

<400> SEQUENCE: 19
ugcgtttgct cttcttcttg cg                                             22

<210> SEQ ID NO 20
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-[hexylamino-(cholesterol)] uridine
      phosphoramidite
<220> FEATURE:
<221> NAME/KEY: misc_feature
<222> LOCATION: (1)..(20)
<223> OTHER INFORMATION: P=S

<400> SEQUENCE: 20
ugcatccccc aggccaccat                                                20
```

```
<210> SEQ ID NO 21
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-[hexylamino-(cholesterol)] uridine
      phosphoramidite
<220> FEATURE:
<221> NAME/KEY: misc_feature
<222> LOCATION: (1)..(20)
<223> OTHER INFORMATION: P=S

<400> SEQUENCE: 21
ucccgcctgt gacatgcatt                                              20

<210> SEQ ID NO 22
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (2)..(2)
<223> OTHER INFORMATION: 2'-O-[hexylamino-(cholesterol)] uridine
      phosphoramidite

<400> SEQUENCE: 22
gutctcgctg gtgagtttca                                              20

<210> SEQ ID NO 23
<211> LENGTH: 19
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-modified with fluorescein
<220> FEATURE:
<221> NAME/KEY: misc_feature
<222> LOCATION: (1)..(19)
<223> OTHER INFORMATION: P=S
<220> FEATURE:
<221> NAME/KEY: misc_feature
<222> LOCATION: (2)..(2)
<223> OTHER INFORMATION: 2'-O-[hexylamino-(cholesterol)] uridine
      phosphoramidite

<400> SEQUENCE: 23
uugggagcca tagcgaggc                                               19

<210> SEQ ID NO 24
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: functionalized to incorporate a pentyl-N-
      phthalmido functionality
```

```
<400> SEQUENCE: 24
ccaagccuca ga                                                         12

<210> SEQ ID NO 25
<211> LENGTH: 12
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (11)..(11)
<223> OTHER INFORMATION: functionalized to incorporate a pentyl-N-
      phthalimido functionality

<400> SEQUENCE: 25
ccaggcucag at                                                         12

<210> SEQ ID NO 26
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: modified with fluorescein
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (20)..(20)
<223> OTHER INFORMATION: 2'-O-hexylphthalimido U 6

<400> SEQUENCE: 26
ugcatccccc aggccaccau                                                 20

<210> SEQ ID NO 27
<211> LENGTH: 21
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: incorporation of 2'-O-(CH2)6-NHCO-O-
      adamantylmethyl uridine using amidite
<220> FEATURE:
<221> NAME/KEY: misc_feature
<222> LOCATION: (1)..(21)
<223> OTHER INFORMATION: P=S

<400> SEQUENCE: 27
ucagtgcctg cgccgcgctc g                                               21

<210> SEQ ID NO 28
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: incorporation of 2'-O-(CH2)6-NHCO-O-
      adamantylmethyl uridine using amidite
```

-continued

```
<220> FEATURE:
<221> NAME/KEY: misc_feature
<222> LOCATION: (1)..(20)
<223> OTHER INFORMATION: P=S

<400> SEQUENCE: 28
uccgtcatcg ctcctcaggg                                          20

<210> SEQ ID NO 29
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (1)..(1)
<223> OTHER INFORMATION: incorporation of 2'-O-(CH2)6-NHCO-
      cholesterol uridine

<400> SEQUENCE: 29
uttaggattc gtgctcatgg                                          20

<210> SEQ ID NO 30
<211> LENGTH: 21
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(21)
<223> OTHER INFORMATION: P=S
<220> FEATURE:
<221> NAME/KEY: misc_feature
<222> LOCATION: (1)..(1)
<223> OTHER INFORMATION: incorporation of 2'-O-(CH2)6-NHCO-
      cholesterol uridine

<400> SEQUENCE: 30
ugttctcgct ggtgagtttc a                                        21

<210> SEQ ID NO 31
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (1)..(20)
<223> OTHER INFORMATION: 3'-O-(CH2)6-NHCO-cholesterol uridine

<400> SEQUENCE: 31
tgcatccccc aggccaccau                                          20

<210> SEQ ID NO 32
<211> LENGTH: 20
<212> TYPE: DNA
<213> ORGANISM: Artificial
<220> FEATURE:
<223> OTHER INFORMATION: Oligonucleotide
<220> FEATURE:
```

```
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (20)..(20)
<223> OTHER INFORMATION: 3'-O-(CH2)6-NHCO-cholesterol uridine

<400> SEQUENCE: 32
gtgctcatgg tgcacggtcu                                              20

<210> SEQ ID NO 33
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: (2'-O-(CH2)6-NHCO-cholesterol uridine
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (20)..(20)
<223> OTHER INFORMATION: 3'-O-(CH2)6-NHCO-cholesterol uridine

<400> SEQUENCE: 33
ugcatccccc aggccaccau                                              20

<210> SEQ ID NO 34
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (8)..(15)
<223> OTHER INFORMATION: 2'-deoxy-2'-fluoro

<400> SEQUENCE: 34
uguucucgct ggtgaguuuc au                                           22

<210> SEQ ID NO 35
<211> LENGTH: 11
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(11)
<223> OTHER INFORMATION: P=O, 2'-5' linkage
<220> FEATURE:
<221> NAME/KEY: misc_feature
<222> LOCATION: (6)..(6)
<223> OTHER INFORMATION: 2'-O-(CH2)6-NHCO-cholesterol U

<400> SEQUENCE: 35
gcgtguctgg g                                                       11

<210> SEQ ID NO 36
<211> LENGTH: 11
<212> TYPE: DNA
<213> ORGANISM: Artificial
<220> FEATURE:
<223> OTHER INFORMATION: Oligonucleotide
```

```
<220> FEATURE:
<221> NAME/KEY: misc_feature
<222> LOCATION: (1)..(11)
<223> OTHER INFORMATION: P=O, 2'-5' Linkage, Chimera having 2'-OMe
      flanks
<220> FEATURE:
<221> NAME/KEY: misc_feature
<222> LOCATION: (6)..(6)
<223> OTHER INFORMATION: 2'-O-(CH2)6-NHCO-cholesterol U

<400> SEQUENCE: 36
gcgugucugc g                                                          11

<210> SEQ ID NO 37
<211> LENGTH: 11
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: 2'-aminolinker or 2'-aminolinker plus pyrene

<400> SEQUENCE: 37
ggctguctgc g                                                          11

<210> SEQ ID NO 38
<211> LENGTH: 12
<212> TYPE: DNA
<213> ORGANISM: Artificial
<220> FEATURE:
<223> OTHER INFORMATION: Oligonucleotide

<400> SEQUENCE: 38
gagctcccag gc                                                         12

<210> SEQ ID NO 39
<211> LENGTH: 15
<212> TYPE: DNA
<213> ORGANISM: Artificial
<220> FEATURE:
<223> OTHER INFORMATION: Oligonucleotide

<400> SEQUENCE: 39
cgactatgca agtac                                                      15

<210> SEQ ID NO 40
<211> LENGTH: 15
<212> TYPE: DNA
<213> ORGANISM: Artificial
<220> FEATURE:
<223> OTHER INFORMATION: Oligonucleotide

<400> SEQUENCE: 40
cgactatgca aaaac                                                      15

<210> SEQ ID NO 41
<211> LENGTH: 21
<212> TYPE: DNA
<213> ORGANISM: Artificial
<220> FEATURE:
<223> OTHER INFORMATION: Oligonucleotide

<400> SEQUENCE: 41
accgaggatc atgtcgtacg c                                               21
```

<210> SEQ ID NO 42
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a pentyl-N-
      phthalimido functionality
<220> FEATURE:
<221> NAME/KEY: misc_feature
<222> LOCATION: (18)..(18)
<223> OTHER INFORMATION: functionalized to incorporate a pentyl-N-
      phthalimido functionality

<400> SEQUENCE: 42
ctgtctccat cctcttcact                                              20

<210> SEQ ID NO 43
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(17)
<223> OTHER INFORMATION: phosphorothioate inter-nucleotide backbone
      linkage
<220> FEATURE:
<221> NAME/KEY: misc_feature
<222> LOCATION: (5)..(5)
<223> OTHER INFORMATION: functionalized to incorporate a pentyl-N-
      phthalimido functionality
<220> FEATURE:
<221> NAME/KEY: misc_feature
<222> LOCATION: (9)..(9)
<223> OTHER INFORMATION: functionalized to incorporate a pentyl-N-
      phthalimido functionality
<220> FEATURE:
<221> NAME/KEY: misc_feature
<222> LOCATION: (11)..(11)
<223> OTHER INFORMATION: functionalized to incorporate a pentyl-N-
      phthalimido functionality
<220> FEATURE:
<221> NAME/KEY: misc_feature
<222> LOCATION: (15)..(15)
<223> OTHER INFORMATION: functionalized to incorporate a pentyl-N-
      phthalimido functionality

<400> SEQUENCE: 43
tgggagccat agcgaggc                                                18

<210> SEQ ID NO 44
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a biotin
      functionality
<220> FEATURE:
<221> NAME/KEY: misc_feature
<222> LOCATION: (18)..(18)
<223> OTHER INFORMATION: functionalized to incorporate a biotin
      functionality

<400> SEQUENCE: 44
ctgtctccat cctcttcact                                              20

```
<210> SEQ ID NO 45
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a fluorescein
      functionality

<400> SEQUENCE: 45
ctgtctccat cctcttcact                                             20

<210> SEQ ID NO 46
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a fluorescein
      functionality
<220> FEATURE:
<221> NAME/KEY: misc_feature
<222> LOCATION: (18)..(18)
<223> OTHER INFORMATION: functionalized to incorporate a fluorescein
      functionality

<400> SEQUENCE: 46
ctgtctccat cctcttcact                                             20

<210> SEQ ID NO 47
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a cholic acid
      functionality

<400> SEQUENCE: 47
ctgtctccat cctcttcact                                             20

<210> SEQ ID NO 48
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a cholic acid
      funtionality
<220> FEATURE:
<221> NAME/KEY: misc_feature
<222> LOCATION: (18)..(18)
<223> OTHER INFORMATION: functionalized to incorporate a cholic acid
      funtionality

<400> SEQUENCE: 48
ctgtctccat cctcttcact                                             20
```

```
<210> SEQ ID NO 49
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: functionalized to incorporate a digoxigenin
      functionality

<400> SEQUENCE: 49
ctgtctccat cctcttcact                                              20

<210> SEQ ID NO 50
<211> LENGTH: 20
<212> TYPE: DNA
<213> ORGANISM: Artificial
<220> FEATURE:
<223> OTHER INFORMATION: Oligonucleotide

<400> SEQUENCE: 50
ctgtctccat cctcttcact                                              20

<210> SEQ ID NO 51
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: cholic acid

<400> SEQUENCE: 51
cccaggcuca ga                                                      12

<210> SEQ ID NO 52
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (12)..(12)
<223> OTHER INFORMATION: cholic acid

<400> SEQUENCE: 52
cccaggcuca ga                                                      12

<210> SEQ ID NO 53
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: cholic acid

<400> SEQUENCE: 53
gagcucccag gc                                                      12

<210> SEQ ID NO 54
```

```
<211> LENGTH: 20
<212> TYPE: DNA
<213> ORGANISM: Artificial
<220> FEATURE:
<223> OTHER INFORMATION: Oligonucleotide

<400> SEQUENCE: 54
gcctttcgcg acccaacacu                                          20

<210> SEQ ID NO 55
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (20)..(20)
<223> OTHER INFORMATION: 3'-O hexylamino-modified nucleoside

<400> SEQUENCE: 55
gcctttcgcg acccaacacu                                          20

<210> SEQ ID NO 56
<211> LENGTH: 12
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: 2'-O-[hexyl-N-(1-pyrene-proply-carbonyl) amino
      uridine

<400> SEQUENCE: 56
gcgtgtuctg cg                                                  12

<210> SEQ ID NO 57
<211> LENGTH: 12
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: 2'-O-[6-bromoacetamido-hex-lyl]-uridine

<400> SEQUENCE: 57
gcgtgtuctg cg                                                  12

<210> SEQ ID NO 58
<211> LENGTH: 12
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: 2'-O-[hexyl-N-(polyethylene glycol)-
      propionoyl]amino uridine

<400> SEQUENCE: 58
gcgtgtuctg cg                                                  12

<210> SEQ ID NO 59
<211> LENGTH: 18
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-hexylamino (dinitrophenyl) uridine
      phosphoramidite
<220> FEATURE:
<221> NAME/KEY: misc_feature
<222> LOCATION: (1)..(18)
<223> OTHER INFORMATION: P=S

<400> SEQUENCE: 59
ugggagccat agcgaggc                                                 18

<210> SEQ ID NO 60
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: P=O

<400> SEQUENCE: 60
ugggagccat agcgaggc                                                 18

<210> SEQ ID NO 61
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-hexylamino (dinitrophenyl) uridine
      phosphoramidite
<220> FEATURE:
<221> NAME/KEY: misc_feature
<222> LOCATION: (1)..(18)
<223> OTHER INFORMATION: P=O
<220> FEATURE:
<221> NAME/KEY: misc_feature
<222> LOCATION: (10)..(10)
<223> OTHER INFORMATION: 2'-O-hexylamino (dinitrophenyl) uridine
      phosphoramidite

<400> SEQUENCE: 61
ugggagccau agcgaggc                                                 18

<210> SEQ ID NO 62
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-hexylamino (dinitrophenyl) uridine
      phosphoramidite
<220> FEATURE:
<221> NAME/KEY: misc_feature
<222> LOCATION: (1)..(18)
<223> OTHER INFORMATION: P=S
<220> FEATURE:
<221> NAME/KEY: misc_feature
<222> LOCATION: (10)..(10)
```

```
<223> OTHER INFORMATION: 2'-O-hexylamino (dinitrophenyl) uridine
      phosphoramidite
<220> FEATURE:
<221> NAME/KEY: misc_feature
<222> LOCATION: (18)..(18)
<223> OTHER INFORMATION: non-nucleoside 6-carbon amino linker

<400> SEQUENCE: 62
ugggagccau agcgaggc                                                       18

<210> SEQ ID NO 63
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-[hexylamino-(cholesterol)] uridine
      phosphoramidite
<220> FEATURE:
<221> NAME/KEY: misc_feature
<222> LOCATION: (1)..(18)
<223> OTHER INFORMATION: P=O

<400> SEQUENCE: 63
ugggagccat agcgaggc                                                       18

<210> SEQ ID NO 64
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: modified with fluorescein
<220> FEATURE:
<221> NAME/KEY: misc_feature
<222> LOCATION: (1)..(18)
<223> OTHER INFORMATION: P=O

<400> SEQUENCE: 64
ugggagccat agcgaggc                                                       18

<210> SEQ ID NO 65
<211> LENGTH: 21
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: modified with fluorescein
<220> FEATURE:
<221> NAME/KEY: misc_feature
<222> LOCATION: (1)..(21)
<223> OTHER INFORMATION: P=S

<400> SEQUENCE: 65
ugcccaagct ggcatccgtc a                                                   21

<210> SEQ ID NO 66
<211> LENGTH: 21
<212> TYPE: DNA
<213> ORGANISM: Artificial
<220> FEATURE:
<223> OTHER INFORMATION: Oligonucleotide
```

```
<220> FEATURE:
<221> NAME/KEY: misc_feature
<222> LOCATION: (1)..(1)
<223> OTHER INFORMATION: modified with fluorescein
<220> FEATURE:
<221> NAME/KEY: misc_feature
<222> LOCATION: (1)..(21)
<223> OTHER INFORMATION: P=S
<220> FEATURE:
<221> NAME/KEY: misc_feature
<222> LOCATION: (21)..(21)
<223> OTHER INFORMATION: non-nucleoside 6-carbon amino linker

<400> SEQUENCE: 66
ugcccaagct ggcatccgtc a                                          21

<210> SEQ ID NO 67
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: modified with fluorescein

<400> SEQUENCE: 67
ugcgtttgct cttcttcttg cg                                         22

<210> SEQ ID NO 68
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: modified with fluorescein
<220> FEATURE:
<221> NAME/KEY: misc_feature
<222> LOCATION: (1)..(20)
<223> OTHER INFORMATION: P=S

<400> SEQUENCE: 68
ugcatccccc aggccaccat                                            20

<210> SEQ ID NO 69
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (2)..(2)
<223> OTHER INFORMATION: modified with fluorescein

<400> SEQUENCE: 69
gutctcgctg gtgagtttca                                            20

<210> SEQ ID NO 70
<211> LENGTH: 18
<212> TYPE: DNA
<213> ORGANISM: Artificial
<220> FEATURE:
```

```
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-O-adamantylmethyl Uridine
      using amidite
<220> FEATURE:
<221> NAME/KEY: misc_feature
<222> LOCATION: (1)..(18)
<223> OTHER INFORMATION: P=O

<400> SEQUENCE: 70
ugggagccat agcgaggc                                                 18

<210> SEQ ID NO 71
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: P=O
<220> FEATURE:
<221> NAME/KEY: misc_feature
<222> LOCATION: (10)..(10)
<223> OTHER INFORMATION: 2'-O-(CH2)6-NHCO-O-adamantylmethyl Uridine
      using amidite

<400> SEQUENCE: 71
tgggagccau agcgaggc                                                 18

<210> SEQ ID NO 72
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-O-adamantylmethyl Uridine
      using amidite
<220> FEATURE:
<221> NAME/KEY: misc_feature
<222> LOCATION: (1)..(20)
<223> OTHER INFORMATION: P=S

<400> SEQUENCE: 72
ugcatccccc aggccaccat                                               20

<210> SEQ ID NO 73
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-O-adamantylmethyl Uridine
      using amidite
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (20)..(20)
<223> OTHER INFORMATION: 2'-modified with fluorescein

<400> SEQUENCE: 73
```
ugcatccccc aggccaccat                                              20

<210> SEQ ID NO 74
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-O-adamantylmethyl Uridine
      using amidite
<220> FEATURE:
<221> NAME/KEY: misc_feature
<222> LOCATION: (1)..(20)
<223> OTHER INFORMATION: P=S

<400> SEQUENCE: 74
ucccgcctgt gacatgcatt                                              20

<210> SEQ ID NO 75
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CN2)6-NHCO-Cis-11-Eicosenoic Uridine
      using amidite
<220> FEATURE:
<221> NAME/KEY: misc_feature
<222> LOCATION: (1)..(18)
<223> OTHER INFORMATION: P=O

<400> SEQUENCE: 75
ugggagccat agcgaggc                                                18

<210> SEQ ID NO 76
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: P=O

<400> SEQUENCE: 76
tgggagccau agcgaggc                                                18

<210> SEQ ID NO 77
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CN2)6-NHCO-Cis-11-Eicosenoic Uridine
      using amidite
<220> FEATURE:
<221> NAME/KEY: misc_feature
<222> LOCATION: (1)..(18)
<223> OTHER INFORMATION: P=S

<400> SEQUENCE: 77

```
ugcatccccc aggccacc                                              18
```

<210> SEQ ID NO 78
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CN2)6-NHCO-Cis-11-Eicosenoic Uridine
      using amidite
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (20)..(20)
<223> OTHER INFORMATION: 2'-modified with fluorescein

<400> SEQUENCE: 78

```
ugcatccccc aggccaccat                                            20
```

<210> SEQ ID NO 79
<211> LENGTH: 21
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CN2)6-NHCO-Cis-11-Eicosenoic Uridine
      using amidite
<220> FEATURE:
<221> NAME/KEY: misc_feature
<222> LOCATION: (1)..(21)
<223> OTHER INFORMATION: P=S

<400> SEQUENCE: 79

```
ucagtgcctg cgccgcgctc g                                          21
```

<210> SEQ ID NO 80
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CN2)6-NHCO-Cis-11-Eicosenoic Uridine
      using amidite
<220> FEATURE:
<221> NAME/KEY: misc_feature
<222> LOCATION: (1)..(20)
<223> OTHER INFORMATION: P=S

<400> SEQUENCE: 80

```
uccgtcatcg ctcctcaggg                                            20
```

<210> SEQ ID NO 81
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature

```
<222> LOCATION: (1)..(1)
<223> OTHER INFORMATION: 2'-O-(CN2)6-NHCO-Cis-11-Eicosenoic Uridine
      using amidite
<220> FEATURE:
<221> NAME/KEY: misc_feature
<222> LOCATION: (1)..(20)
<223> OTHER INFORMATION: P=S

<400> SEQUENCE: 81
ucccgcctgt gacatgcatt                                                    20

<210> SEQ ID NO 82
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-butyryl pyrene Uridine
      using amidite
<220> FEATURE:
<221> NAME/KEY: misc_feature
<222> LOCATION: (1)..(18)
<223> OTHER INFORMATION: P=O

<400> SEQUENCE: 82
ugggagccat agcgaggc                                                      18

<210> SEQ ID NO 83
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: P=O
<220> FEATURE:
<221> NAME/KEY: misc_feature
<222> LOCATION: (10)..(10)
<223> OTHER INFORMATION: 2'-O-(CH2)6-NHCO-butyryl pyrene Uridine
      using amidite

<400> SEQUENCE: 83
tgggagccau agcgaggc                                                      18

<210> SEQ ID NO 84
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-butyryl pyrene Uridine using
      amidite
<220> FEATURE:
<221> NAME/KEY: misc_feature
<222> LOCATION: (1)..(20)
<223> OTHER INFORMATION: P=S

<400> SEQUENCE: 84
ugcatccccc aggccaccat                                                    20

<210> SEQ ID NO 85
<211> LENGTH: 20
<212> TYPE: DNA
```

```
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (20)..(20)
<223> OTHER INFORMATION: 3'-aminolink

<400> SEQUENCE: 85
ugcatccccc aggccaccat                                               20

<210> SEQ ID NO 86
<211> LENGTH: 21
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-butyryl pyrene Uridine using
      amidite
<220> FEATURE:
<221> NAME/KEY: misc_feature
<222> LOCATION: (1)..(21)
<223> OTHER INFORMATION: P=S

<400> SEQUENCE: 86
ucagtgcctg cgccgcgctc g                                             21

<210> SEQ ID NO 87
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-butyryl pyrene Uridine using
      amidite
<220> FEATURE:
<221> NAME/KEY: misc_feature
<222> LOCATION: (1)..(20)
<223> OTHER INFORMATION: P=S

<400> SEQUENCE: 87
uccgtcatcg ctcctcaggg                                               20

<210> SEQ ID NO 88
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-butyryl pyrene Uridine using
      amidite
<220> FEATURE:
<221> NAME/KEY: misc_feature
<222> LOCATION: (1)..(20)
<223> OTHER INFORMATION: P=S

<400> SEQUENCE: 88
ucccgcctgt gacatgcatt                                               20
```

<210> SEQ ID NO 89
<211> LENGTH: 21
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-butyryl pyrene Uridine using
    amidite
<220> FEATURE:
<221> NAME/KEY: misc_feature
<222> LOCATION: (1)..(21)
<223> OTHER INFORMATION: P=S

<400> SEQUENCE: 89
ugttctcgct ggtgagtttc a                                              21

<210> SEQ ID NO 90
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesterol Uridine at 5' End
    using amidites

<400> SEQUENCE: 90
ugggagccat agcgaggc                                                  18

<210> SEQ ID NO 91
<211> LENGTH: 21
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesterol Uridine at 5' End
    using amidites
<220> FEATURE:
<221> NAME/KEY: misc_feature
<222> LOCATION: (1)..(21)
<223> OTHER INFORMATION: P=S

<400> SEQUENCE: 91
ugcccaagct ggcatccgtc a                                              21

<210> SEQ ID NO 92
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesterol Uridine at 5' End
    using amidites
<220> FEATURE:
<221> NAME/KEY: misc_feature
<222> LOCATION: (1)..(22)
<223> OTHER INFORMATION: P=S

<400> SEQUENCE: 92
ugcgtttgct cttcttcttg cg                                             22

<210> SEQ ID NO 93
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesterol Uridine at 5' End using amidites
<220> FEATURE:
<221> NAME/KEY: misc_feature
<222> LOCATION: (1)..(20)
<223> OTHER INFORMATION: P=S

<400> SEQUENCE: 93
ugcatccccc aggccaccat            20

<210> SEQ ID NO 94
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesterol Uridine at 5' End using amidites
<220> FEATURE:
<221> NAME/KEY: misc_feature
<222> LOCATION: (1)..(20)
<223> OTHER INFORMATION: P=S

<400> SEQUENCE: 94
ucccgcctgt gacatgcatt            20

<210> SEQ ID NO 95
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesterol Uridine at 5' End using amidites
<220> FEATURE:
<221> NAME/KEY: misc_feature
<222> LOCATION: (1)..(18)
<223> OTHER INFORMATION: P=S

<400> SEQUENCE: 95
ugggagccat agcgaggc            18

<210> SEQ ID NO 96
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(18)
<223> OTHER INFORMATION: P=O
<220> FEATURE:
<221> NAME/KEY: misc_feature
<222> LOCATION: (10)..(10)
<223> OTHER INFORMATION: 2'-O-(CH2)6-NHCO-cholesterol Uridine at

```
                        nonterminal positions using amidite

<400> SEQUENCE: 96
tgggagccau agcgaggc                                               18

<210> SEQ ID NO 97
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (2)..(2)
<223> OTHER INFORMATION: 2'-O-(CH2)6-NHCO-cholesterol Uridine at
      nonterminal positions using amidite

<400> SEQUENCE: 97
gutctcgctg gtgagtttca                                             20

<210> SEQ ID NO 98
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=S
<220> FEATURE:
<221> NAME/KEY: misc_feature
<222> LOCATION: (20)..(20)
<223> OTHER INFORMATION: 3'-O-(CH2)6-NHCO-cholesterol Uridine at 3' end
      using modified CPG

<400> SEQUENCE: 98
gcctttcgcg acccaacacu                                             20

<210> SEQ ID NO 99
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=O
<220> FEATURE:
<221> NAME/KEY: misc_feature
<222> LOCATION: (20)..(20)
<223> OTHER INFORMATION: 3'-O-(CH2)6-NHCO-cholesterol Uridine at 3' end
      using modified CPG

<400> SEQUENCE: 99
gcctttcgcg acccaacacu                                             20

<210> SEQ ID NO 100
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
```

```
<223> OTHER INFORMATION: P=S
<220> FEATURE:
<221> NAME/KEY: misc_feature
<222> LOCATION: (20)..(20)
<223> OTHER INFORMATION: 3'-O-(CH2)6-NHCO-cholesterol Uridine at 3' end
      using modified CPG

<400> SEQUENCE: 100
tgcatccccc aggccaccau                                                 20

<210> SEQ ID NO 101
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(20)
<223> OTHER INFORMATION: P=O
<220> FEATURE:
<221> NAME/KEY: misc_feature
<222> LOCATION: (20)..(20)
<223> OTHER INFORMATION: 2'-O-(CH2)6-NHCO-cholesterol Uridine at 3' end
      using modified CPG

<400> SEQUENCE: 101
tgcatccccc aggccaccau                                                 20

<210> SEQ ID NO 102
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesteral Uridine
<220> FEATURE:
<221> NAME/KEY: misc_feature
<222> LOCATION: (1)..(20)
<223> OTHER INFORMATION: P=O
<220> FEATURE:
<221> NAME/KEY: misc_feature
<222> LOCATION: (20)..(20)
<223> OTHER INFORMATION: 3'-O-(CH2)6-NHCO-cholesterol Uridine

<400> SEQUENCE: 102
ugcatccccc aggccaccau                                                 20

<210> SEQ ID NO 103
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (8)..(15)
<223> OTHER INFORMATION: 2'-deoxy-2'-fluoro
<220> FEATURE:
<221> NAME/KEY: misc_feature
<222> LOCATION: (22)..(22)
<223> OTHER INFORMATION: 3'-O-(CH2)6-NH2 U

<400> SEQUENCE: 103
uguucucgct ggtgaguuuc au                                              22

<210> SEQ ID NO 104
<211> LENGTH: 22
```

```
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (8)..(15)
<223> OTHER INFORMATION: 2'-deoxy-2'-fluoro
<220> FEATURE:
<221> NAME/KEY: misc_feature
<222> LOCATION: (22)..(22)
<223> OTHER INFORMATION: 3'-O-(CH2)6-NHCO-cholesterol U

<400> SEQUENCE: 104
uguucucgct ggtgaguuuc au                                            22

<210> SEQ ID NO 105
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesterol U
<220> FEATURE:
<221> NAME/KEY: misc_feature
<222> LOCATION: (8)..(15)
<223> OTHER INFORMATION: 2'-deoxy-2'-fluoro
<220> FEATURE:
<221> NAME/KEY: misc_feature
<222> LOCATION: (22)..(22)
<223> OTHER INFORMATION: 3'-O-(CH2)6-NHCO-cholesterol U

<400> SEQUENCE: 105
uguucucgct ggtgaguuuc au                                            22

<210> SEQ ID NO 106
<211> LENGTH: 22
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: 2'-O-(CH2)6-NHCO-cholesterol U
<220> FEATURE:
<221> NAME/KEY: misc_feature
<222> LOCATION: (8)..(15)
<223> OTHER INFORMATION: 2'-deoxy-2'-fluoro

<400> SEQUENCE: 106
uguucucgct ggtgaguuuc au                                            22

<210> SEQ ID NO 107
<211> LENGTH: 11
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: 2'-O-(CH2)6-NHCO-cholesterol U

<400> SEQUENCE: 107
gcgtguctgg g                                                        11
```